US012544427B2

(12) United States Patent
Ellison et al.

(10) Patent No.: US 12,544,427 B2
(45) Date of Patent: Feb. 10, 2026

(54) USE OF GDF15 FOR TREATING CARDIOMETABOLIC SYNDROME AND OTHER CONDITIONS

(71) Applicant: Amgen Inc., Thousand Oaks, CA (US)

(72) Inventors: Murielle Marie V. Ellison, Thousand Oaks, CA (US); Clarence H. Hale, Camarillo, CA (US); Xin Luo, San Francisco, CA (US); Marina Stolina, Beverly Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 784 days.

(21) Appl. No.: 17/765,883

(22) PCT Filed: Oct. 2, 2020

(86) PCT No.: PCT/US2020/053884
§ 371 (c)(1),
(2) Date: Apr. 1, 2022

(87) PCT Pub. No.: WO2021/067655
PCT Pub. Date: Apr. 8, 2021

(65) Prior Publication Data

US 2023/0210950 A1 Jul. 6, 2023

Related U.S. Application Data

(60) Provisional application No. 62/910,661, filed on Oct. 4, 2019.

(51) Int. Cl.
*A61K 38/18* (2006.01)

(52) U.S. Cl.
CPC .......... *A61K 38/18* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 5,288,931 | A | 2/1994 | Chang et al. |
| 6,737,056 | B1 | 5/2004 | Presta |
| 7,112,660 | B1 | 9/2006 | Domingues et al. |
| 7,271,149 | B2 | 9/2007 | Glaesner et al. |
| 8,338,569 | B2 | 12/2012 | Marshall et al. |
| 8,362,210 | B2 | 1/2013 | Lazar et al. |
| 8,372,952 | B2 | 2/2013 | Smith et al. |
| 8,629,244 | B2 | 1/2014 | Kolkman et al. |
| 9,161,966 | B2 | 10/2015 | Matern et al. |
| 9,248,181 | B2 | 2/2016 | De Kruif |
| 9,272,019 | B2 | 3/2016 | Shaw et al. |
| 9,550,819 | B2 | 1/2017 | Lindhout |
| 9,714,276 | B2 | 7/2017 | Xiong et al. |
| 9,827,291 | B2 | 11/2017 | Matern et al. |
| 9,828,415 | B2 | 11/2017 | Matern et al. |
| 9,834,586 | B2 | 12/2017 | Lindhout et al. |
| 9,862,752 | B2 | 1/2018 | Xiong et al. |
| 9,920,118 | B2 | 3/2018 | Shen et al. |
| 10,195,250 | B2 | 2/2019 | Lindhout et al. |
| 10,336,812 | B2 | 7/2019 | Armstrong et al. |
| 10,752,664 | B2 | 8/2020 | Xiong et al. |
| 11,161,889 | B2 | 11/2021 | Xiong et al. |
| 2003/0045474 | A1 | 3/2003 | Sailer et al. |
| 2004/0053366 | A1 | 3/2004 | Lo et al. |
| 2006/0275283 | A1 | 12/2006 | Van Vlijmen et al. |
| 2007/0003546 | A1 | 1/2007 | Lazar et al. |
| 2007/0054853 | A1 | 3/2007 | Fujise et al. |
| 2007/0161081 | A1 | 7/2007 | Jin et al. |
| 2009/0004181 | A1 | 1/2009 | Breit |
| 2009/0042780 | A1 | 2/2009 | Knopf et al. |
| 2010/0087627 | A1 | 4/2010 | Marshall et al. |
| 2010/0278843 | A1 | 11/2010 | Breit et al. |
| 2011/0150901 | A1 | 6/2011 | Smith et al. |
| 2011/0195067 | A1 | 8/2011 | Arnason et al. |
| 2011/0229472 | A1 | 9/2011 | Min et al. |
| 2011/0236375 | A1 | 9/2011 | Lazar et al. |
| 2013/0336981 | A1 | 12/2013 | De Kruif et al. |
| 2014/0213511 | A1 | 7/2014 | Matern et al. |
| 2015/0023960 | A1 | 1/2015 | Lindhout et al. |
| 2015/0139996 | A1 | 5/2015 | De Kruif et al. |
| 2016/0030585 | A1 | 2/2016 | Barnes et al. |
| 2016/0031960 | A1 | 2/2016 | Lindhout et al. |
| 2016/0120999 | A1 | 5/2016 | Shen et al. |
| 2016/0129082 | A1 | 5/2016 | Matern et al. |

(Continued)

FOREIGN PATENT DOCUMENTS

| | | | |
|---|---|---|---|
| CN | 1723220 | A | 1/2006 |
| CN | 1974601 | A | 6/2007 |

(Continued)

OTHER PUBLICATIONS

Erik Kirk and Samuel Klein, J Clin Hypertens 2009; 11: 761-765 (Year: 2009).*
Eaton et al., Circ Heart Fail. 2016;9:e002883 (Year: 2016).*
Mendez Fernandez, European Journal of Heart Failure, (May 2018) vol. 20, Supp. Supplement 1, pp. 245-246. Abstract No. P1013 (Year: 2018).*
Abma (Blood Sugar Monitoring: When to Check and Why, 2009).
Alain et al., Therapeutic Fc-fusion proteins and peptides as successful alternatives to antibodies, MABS, 2011, 3:5, 415-416.

(Continued)

*Primary Examiner* — Christina M Borgeest
(74) *Attorney, Agent, or Firm* — Amy C. Madl

(57) ABSTRACT

The present disclosure provides a method of treating cardiometabolic syndrome (CMS) with a GDF15 molecule. Also provided herein is a method of treating a cardiac or heart condition. In some embodiments, the GDF15 molecule is a GDF15-Fc fusion, in which a GDF15 region is fused to an Fc region, optionally via a linker.

10 Claims, 31 Drawing Sheets

Specification includes a Sequence Listing.

(56) References Cited

U.S. PATENT DOCUMENTS

2016/0200787 A1 7/2016 Matern et al.
2017/0107248 A1 4/2017 Lou et al.
2017/0204149 A1 7/2017 Chopra et al.
2017/0299608 A1 10/2017 Hsu et al.
2017/0327560 A1* 11/2017 Armstrong ............ C07K 14/51
2018/0079790 A1 3/2018 Xiong et al.
2019/0000923 A1 1/2019 Chutkow et al.
2019/0248852 A1 8/2019 Zhang et al.
2019/0292241 A1 9/2019 Armstrong et al.
2019/0309033 A1 10/2019 Gonciarz et al.
2022/0152154 A1 5/2022 Xiong et al.

FOREIGN PATENT DOCUMENTS

EP 0036676 A1 9/1981
EP 0036776 A2 9/1981
EP 0058481 A1 8/1982
EP 0088046 A2 9/1983
EP 0133988 A2 3/1985
EP 0143949 B1 10/1988
EP 2098244 A1 9/2009
EP 2330197 A2 6/2011
EP 2439535 A1 4/2012
EP 2694092 B1 1/2017
JP 2003081831 A 3/2003
JP 2007532586 A 11/2007
JP 2010536717 A 12/2010
WO 199315722 A1 8/1993
WO 199906445 A1 8/2005
WO 2005077981 A2 8/2005
WO 2005099746 A1 10/2005
WO 2006000448 A2 1/2006
WO 2007041635 A2 4/2007
WO 2009021293 A8 2/2009
WO 2009089004 A1 7/2009
WO 2009141357 A1 11/2009
WO 2010017198 A2 2/2010
WO 2010048670 A1 5/2010
WO 2011/063348 A1 5/2011
WO 2011064758 A2 6/2011
WO 2012138919 A1 10/2011
WO 2012007868 A2 1/2012
WO 2012007869 A2 1/2012
WO 2012007877 A2 1/2012
WO 2012025355 A1 3/2012
WO 2012058768 A1 5/2012
WO 2012125850 A1 9/2012
WO 2012146628 A1 11/2012
WO 2013/096291 A2 6/2013
WO 2013113008 A1 8/2013
WO 2013148117 A1 10/2013
WO 2013157953 A1 10/2013
WO 2013157954 A1 10/2013
WO 2014100689 A1 6/2014
WO 2014120619 A2 8/2014
WO 2015198199 A1 12/2015
WO 2017/112824 A2 6/2017
WO 2017/121865 A1 7/2017
WO 2017/147742 A1 9/2017
WO 2019/048660 A1 3/2019
WO 2019/199685 A1 10/2019

OTHER PUBLICATIONS

American Diabetes Association Standards of Medical Care in Diabetes Care-2011.
Ansel et al., Pharmaceutical Dosage Forms & Drug Delivery Systems, 7th ed. 2000.
Aulton, Pharmaceutics: the Science of Dosage Form Design, Churchill Livingstone, New York, 1988.
Ausubel et al., eds., Current Protocols in Molecular Biology, Green Publishers Inc. and Wiley and Sons, 1994.
Aronne, Treating Obesity: A New Target for Prevention of Coronary Heart Disease (Prog Cardiovasc Nurs. 2001 ; 16(3)).
Baek Sj, J. Biol Chemistry, 2001, 276:33384-33392.
Baek Sj, Gastroenterology, 2006, 131:1553-1560.
Bauskin Ar, Embo J., 2000, 19:2212-2220; NCBI.
Beck et al., "Therapeutic Fc-fusion proteins and peptides as successful alternatives to antibodies," MABS, 3(5):415-416 (2011).
Berge et al., "Pharmaceutical Salts", J. Pharm. Science, 1977, 6661, 1-19.
Biotek (Determination of Insulin Levels in Human Serum, 2009).
Bootcov Mr, 1997, Proc Natl Acad Sci 94:11514-11519.
Bottner M , Gene, 1999, 237:105-11.
Carrillo et al., Siam J. Applied Math., 1988, 48:1073.
Cekanova M, "Nonsteroidal anti-inflammatory drug-activated gene-1 expression inhibits urethane-induced pulmonary tumorigenesis in transgenic mice", 2009, Cancer Prev Res 2:5, 450-458.
Computational Molecular Biology, Lesk, A. M., ed., 1988, New York: Oxford University Press; Biocomputing Informatics and Genome Projects, Smith, D. W., ed., 1993, New York: Academic Press.
Creative BioMart, Recombinant Human Growth Differentiation Factor 15. Fe Chimera; Oct. 23, 2010 (according to document properties for posted document); (Retrieved from the Internet Apr. 9, 2013 http://img.creativebiomart.netlpdf/GDF15-204H.GDF15 ,Fc%20Chimera. pdf>.
Czajkowsky, et al., EMBO Mol Med, Epub, 2012 4(10), 1015-1028.
Czajkowsky, et al., "Fc-fusion proteins: new developments and future perspectrives". EMBO Mol Med, Epub, 2012 4(10), 1015-1028.
Dayhoff et al., Atlas of Protein Sequence and Structure, 1978, 5:345-352.
Devereux et al., Nucl. Acid Res. 1984, 12:387.
Diabetes self-management (downloaded online from URL:<http://www.diabetesselfmanagement.com/diabetesresources/definitions/prediabetes/>, 2006).
Dinsmoor (downloaded online from URL :<http://www.diabetesselfmanagement.com/managing-diabetes/complicationsprevention/protecting-your-kidneys/, 2009).
Dostalova, et al.: Increased serum concentrations of macrophage inhibitory cytokine-1 in patients with obesity and type 2 diabetes mellitus: the influence of very low calorie diet.: European Journal of Endocrinology /European Federation of Endocrine Societies Sep. 2009, vol. 161 No. 3, (Sep. 2009), pp. 397-404.
Epstein et al., Proc. Natl. Acad. Sci. US, 1985, 82: 3688-3692.
Fairlie Wd, Gene, 2000, 254: 67-76.
Freiberg & Zhu, Int. J. Pharm., 2004, 282:1-18.
GenBank: AF003934.1 (*Homo sapiens* prostate differentiation factor mRNA, complete cds, 1997).
Gribskov, M. and Devereux, J., eds., Sequence Analysis Primer, 1991, New York: M. Stockton Press.
Griffin, A. M., and Griffin, H. G., eds., Computer Analysis of Sequence Data, Part I, 1994, New Jersey: Humana Press.
Henikoff et al., Proc. Natl. Acad. Sci. USA 1992, 89:10915-10919.
Hromas R., Biochim Biophys Acta. 1997, 1354:40-44.
Inoue et al., Nat Med. Feb. 2004; 10(2):168-74.
Jenson, et al. "A novel Fc gamma receptor ligand augments humoral responses by targeting antigen to Fc gamma receptors", Eur. J. Immunol, 2007, 37:4, 1139-1148.
Johnen H, Nat Med., 2007, 11:1333-1340.
Katoh M, Int J Mol Med, 2006. 17:951-955.
Kempf T, "The Transforming Growth Factor-{szligbeta} Superfamily Member Growth-Differentiation Factor-15 Protects the Heart From Ischemia/Reperfusion Injury", Circ Res., 2006, 98:351-360.
Lajer Maria, et al.: "Plasma growth differentiation factor-15 independently predicts all-cause and cardiovascular mortality as well as deterioration of kidney function in type 1 diabetic patients with nephropathy.", Diabetes Care, vol. 33, No. 7, Jul. 2010 (Jul. 2010), pp. 1567-1572.
Langer et al., J. Biomed. Mater. Res., 1981, 15:167-277.
Langer, Chem. Tech., 1982, 12: 98-105.
Lawton Ln, "Identification of a novel member of the TGF-beta superfamily highly expressed in human placenta", Gene, 1997, 203:17-26.

(56) References Cited

OTHER PUBLICATIONS

Lind et al.: "Growth-differentiation factor-15 is an independent marker of cardiovascular dysfunction and disease in the elderly; results from the Prospective Investigation of the Vasculature in Uppsala Seniors (PIVUS) Study", European Heart Journal (Online), Oxford University Press, GB, US, NI., vol. 30, No. 19, Oct. 1, 2009 (Oct. 1, 2009), pp. 2346-2353.
Lo et al. (2005, Protein Engineering, Design & Selection 18:1-10).
Macia L. et al., PLoS One., Apr. 13, 2012, vol. 7, No. 4, pp. e34868.
Mekhaiel, et al. "Polymeric human Fc-fusion proteins with modified effector functions", 2011, Sci Rep. 1:124.
Moore A.G., "The transforming growth factor-ss superfamily cytokine macrophage inhibitory cytokine-1 is present in high concentrations in the serum of pregnant women", J Clin Endocrinol Metab, 2006, 85: 4781-4788.
NCBI Reference Sequence: NP 004855.2 (Jan. 13, 2011).
Needleman et al., J. Mol. Biol., 1970, 48:443-453.
Paralkar Vm, "Cloning and characterization of a novel member of the transforming growth factor-beta/bone morphogenetic protein family", J. Biol. Chemistry, 1998, 273:13760-13767.
Remington: the Science and Practice of Pharmacy, 19th edition, 1995.
Rose-John et al., "The IL-6/sIL-6R complex as a novel target for therapeutic approaches," Expert Opinion on Therapeutic Targets, 11:5, 613-624 (2007).
Sambrook, J., Fritsh, E. F., and Maniatis, T. Molecular Cloning: A Laboratory Manual 2nd, ed., Cold Spring Harbor Laboratory, Cold Spring Harbor Laboratory Press, Cold Spring Harbor, N. Y., 1989.
Sidman et al., Biopolymers 1983, 22: 547-56.
Sino Biological Inc. (http://www.sinobiological.com/GDF-15-Protein-g-570.html; available May 1, 2010).
Smith, D. W., ed, Biocomputing Informatics and Genome Projects, 1993, New York: Academic Press.
Strelau J, "Progressive Postnatal Motoneuron Loss in Mice Lacking GDF-15", J Neuroscience, 2009, 29:13640-13648.
Tamary H, Blood, 2008, 112:5241-5244.
Tanno T, "High levels of GDF15 in thalassemia suppress expression of the iron regulatory protein hepcidin", Nat Med, 2007, 13:1096-1101.
Van Heeke & Schuster, "Expression of human asparagine synthetase in *Escherichia coli*", J. Biol. Chem., 1989, 264: 5503-5509.
Von Heinje, G., Sequence Analysis in Molecular Biology, 1987, New York: Academic Press.
White, "Design and expression of polymeric immunoglobulin fusion proteins: a strategy for target in low-affinity Fogamma receptors", Protein Expr, Purif, 2001, 21:3, 446-455.
White et al., "Rapid Immune Responses to a Botulinum Neurotoxin Hc Subunit Vaccine through in Vivo Targeting to Antigen-Presenting Cells," *Infect. Immun*., Epub, 79(8):3388-3396 (2011).
Wilson and Gisvolds' Textbook of Organic Medicinal and Pharmaceutical Chemistry, Delgado and Remers, Eds., 10th ed., 1998.
Wischke & Schwendeman, Int. J. Pharm., 2008, 364: 298-327.
Xu J, "GDF15/MIC-1 Functions as a Protective and Antihypertrophic Factor Released From the Myocardium in Association With SMAD Protein Activation", Circ Res., 2006, 98:342-350.
Zimmermann Mb, "Iron metabolism in heterozygotes for hemoglobin E (HbE),—thalassemia 1, or -thalassemia and in compound heterozygotes for HbE/-thalassemia", Am J Clin Nutr, 2008, 88:1026-1031.
K. Gunasekaran et al: "Enhancing Antibody 2-24 Fc Heterodimer Formation through Electrostatic Steering Effects: Applications to Bispecific Molecules and Monovalent IgG", Journal of Biological Chemistry, vol. 285, No. 25, Jun. 18, 2010 (Jun. 18, 2010), pp. 19637-19646.
International Search Report and Written Opinion for PCT Application No. PCT/US2020/053884, mailed on Feb. 4, 2021.
Arnold, The Impact of Glycosylation on the Biological Function and Structure of Human Immunoglobulins, Annual Rev. Immunol; 25: 21-50, 2007.
Wang, IgG Fc engineering to modulate antibody effector functions; Protein Cell, 9(1): 63-73, 2018.
Nguyen, et al., Both male and female obese ZSF1 rats develop cardiac dysfunction in obesity induced heart failure with preserved ejection fraction, Plos One; 1-16; 2020.
Stolina, et al., The evolving systemic biomarker milieu in obese ZSF1 rat model of human cardiometabolic syndrome: Characterization of the model and cardioprotective effect of GDF15, Plos One; 1-25; 2020.
Reddy et al., "Cilostazol ameliorates heart failure with preserved ejection fraction and diastolic dysfunction in obese and nonobese hypertensive mice", Journal of Molecular and Cellular Cardiology, vol. 123, pp. 46-57 (2018).
"Metabolic Disease," Encyclopedia Britannica, https://www.britannica.com/science/metabolic-disease; (Accessed Jul. 21, 2023).
Alaoui-Ismalli and Falb (2009), "Design of second generation therapeutic recombinant bone morphogenetic proteins", Cytokine & Growth Factors Rev., 20:501-507.
American Diabetes Association, "Standards of medical care in diabetes—2010", Diabetes Care, vol. 33 (Suppl 1), pp. S11-S61 (2010).
Bernier et al., "Pharmacological chaperone action on G-protein-coupled receptors," Current Opinion in Pharmacology, vol. 4: pp. 528-533 (2004).
Bhattacharya et al., "Impact of genetic variation on three dimensional structure and function of proteins," PLoS One, vol. 12 (3): e0171355, pp. 1-22 (2017).
Blau et al., "Phenylketonuria," Lancet., vol. 376(9750): 1417-27 (2010).
Brodkin et al., "Prediction of distal residue participation in enzyme catalysis," Protein Science, 24:762-778 (2015).
Butt et al., "Diabetic Nephropathy," Cleveland Clinic Center for Continuing Education (2010).
Catalog No. GDF15-362H, "Recombinant Human Growth and Differentiation Factor-15", Creative BioMart, Specification sheet Rev 092708A, 1 page (2010).
Coleman et al., "The Influence of Genetic Background on the Expression of the Obese (ob) Gene in the Mouse," Diabetologia, 9(4):287-293 (1973).
Dinsmoor, R. S., "Proteinuria," Diabetes Self-Management (2006).
Emmerson et al., "The metabolic effects of GDF15 are mediated by the orphan receptor GFRAL," Nature Medicine, 23(10):1215-1219 (2017).
Etzweiler, D., "Type II, or non-insulin-dependent Diabetes Mellitus Results from an Inability of Insulin Target Tissues to Respond to the Hormone," Diabetes Mellitus, 459 (1966).
Foggensteiner et al., "Management of diabetic nephropathy," Journal of the Royal Society of Medicine, 94 (5):210-217 (2001).
Foo et al., "Mutation of outer-shell residues modulates metal ion co-ordination strength in a metalloenzyme," Biochemical Journal, 429:313-321 (2010).
Frikke-Schmidt et al., "GDF15 acts synergistically with liraglutide but is not necessary for weight loss induced by bariatric surgery in mice," Molecular Metabolism, vol. 21: pp. 13-21 (2019).
Gennaro et al., "Remington's Pharmaceutical Sciences", 18th Edition, Mack Publishing Company, Easton, Pennsylvania, 13 pages (1990).
Golay et al., "Link between obesity and type 2 diabetes," Best Practice & Research Clinical Endocrinology & Metabolism, 19(4):649-663 (2005).
Goodman and Gilman, Eds., The Pharmacological Basis of Therapeutics, 9th ed., 1996.
Guo et al., "Protein tolerance to random amino acid change", Proc. Natl. Acad, Sci., vol. 101 (25), pp. 9205-9210 (2004).
Heymsfield et al. "Effects of weight loss with orlistat on glucose tolerance and progression to type 2 diabetes in obese adults." Archives of Internal Medicine, vol. 160(9), pp. 1321-1326 (2000).
Hossain et al., "Obesity and Diabetes in the Developing World—A Growing Challenge," The New England Journal ofMedicine, 356(3):213-215 (2007).
Howard et al., "Obesity and dyslipidemia," Endocrinology and Metabolism Clinics of North America, 32:855-867 (2003).

(56) References Cited

OTHER PUBLICATIONS

Hsu et al., "Non-homeostatic body weight regulation through a brainstem-restricted receptor for GDF15," Nature, 550 (7675):255-259 (2017).
Inoue et al., "Paclitaxel Enhances the Effects of the Anti-Epidermal Growth Factor Receptor Monoclonal Antibody ImClone C225 in Mice with Metastatic Human Bladder Transitional Cell Carcinoma", Clin Cancer Res., vol. 6 (12), pp. 4874-4884 (2000).
International Search Report and Written Opinion for PCT Application No. PCT/US2020/021314, mailed on Jun. 5, 2020.
International Search Report and Written Opinion mailed on Jun. 13, 2019 for PCT Application No. PCT/ US2019/026369 filed Apr. 8, 2019 (13 pages).
International Search Report dated Dec. 10, 2014 in PCT Application No. PCT/US2014/049254.
Kikkawa, R., "Guidelines for the Treatment of Diabetic Nephropathy," Asian Medical Journal, 44(2): 71-75 (2001).
Killion et al., "Anti-obesity effects of GIPR antagonists alone and in combination with GLP-1R agonists in preclinical models," Sci. Transl. Med., vol. 10(472): pp. 3392 (2018).
Leite et al., "Arterial Remodeling and Dysfunction in the ZSF1 Rat Model of Heart Failure With Preserved Ejection Fraction", Circulation. Heart Failure (Print), vol. 12, No. 7, Jul. 1, 2019, XP055766389.
Lieberman et al., Pharmaceutical Dosage Forms-Disperse Systems, 1998, 2nd Ed., V3.
Maric et al., "Obesity, metabolic syndrome and diabetic nephropathy," Contrib Nephrol., 170: 28-35(2011).
Massague, J., "TGF-Beta in Cancer," Cell, 134, 215-230 (2008).
Mooradian, A., "Dyslipidemia in type 2 diabetes mellitus," Nature Clinical Practice, Endocrinology & Metabolism, 5 (3): 150-159 (2009).
Mullican et al., "GFRAL is the receptor for GDF15 and the ligand promotes weight loss in mice and nonhuman primates," Nature Medicine, 23(10): 1150-1157 (2017).
Mullican et al., "Uniting GDF15 and GFRAL: Therapeutic Opportunities in Obesity and Beyond," Trends in Endocrinology and Metabolism, vol. 29(8): 560-570 (2018).
Muraoka et al., "Blockade of TGF-Beta inhibits mammary tumor cell viability, migration, and metastases," J. Clin. Invest., vol. 109(12): pp. 1551-1559 (2002).
Patel et al., "GDF15 Provides an Endocrine Signal of Nutritional Stress in Mice and Humans," Cell Metabolism, vol. 29(3): pp. 707-718 (2019).
Pontiroli et al. "Body weight and glucose metabolism have a different effect on circulating levels of ICAM-1, E-selectin, and endothelin-1 in humans," European Journal of Endocrinology, vol. 150(2), pp. 195-200 (2004).
Rao et al., "Impaired Glucose Tolerance and Impaired Fasting Glucose," American Family Physician, vol. 69(8), pp. 1961-1968 (2004).
Sainsbury et al., "Y2 Receptor Deletion Attenuates the Type 2 Diabetic Syndrome of ob/ob Mice," Diabetes, 51:3420-3427 (2002).
Styer, "Metabolic Derangements in Diabetes Result from Relative Insulin Insufficiency and Glucagon Excess," Biochemistry, 4th Edition, 779-780 (1995).
Tallarida, R. J., "Quantitative methods for assessing drug synergism" Genes Cancer, vol. 2(11), pp. 1003-1008 (2011).
Tokuriki et al., "Stability effects of mutations and protein evolvability", Curr. Opin. Struct. Biol., vol. 19, pp. 596-604 (2009).
Ulloa-Aguirre, "Pharmacologic Rescue of Conformationally-Defective Proteins: Implications for the Treatment of Human Disease," Traffic, vol. 5: pp. 821-837 (2004).
Who, "Fight childhood obesity to help prevent diabetes, say WHO & IDF," World Health Organization (2004).
Wollert et al., "Growth Differentiation Factor 15 in Heart Failure: An Update", Current Heart Failure Reports, vol. 9, No. 4, Sep. 9, 2012, pp. 337-345.
Yang et al., "GFRAL is the receptor for GDF15 and is required for the anti-obesity effects of the ligand," Nature Medicine, 23(10):1158-1166 (2017).
Yang et al., "Lifetime exposure to a soluble TGF-Beta antagonist protects mice against metastasis without adverse side effects," J. Clin. Invest., vol. 109(12): pp. 1607-1615 (2002).

* cited by examiner

OPN sE-Selectin

SEQUENCE LISTING

```
<160> NUMBER OF SEQ ID NOS: 58

<210> SEQ ID NO 1
<211> LENGTH: 927
<212> TYPE: DNA
<213> ORGANISM: Homo sapiens

<400> SEQUENCE: 1

atgcccgggc aagaactcag gacggtgaat ggctctcaga tgctcctggt gttgctggtg     60

ctctcgtggc tgccgcatgg gggcgccctg tctctggccg aggcgagccg cgcaagtttc    120

ccgggaccct cagagttgca ctccgaagac tccagattcc gagagttgcg gaaacgctac    180

gaggacctgc taaccaggct gcgggccaac cagagctggg aagattcgaa caccgacctc    240

gtcccggccc ctgcagtccg gatactcacg ccagaagtgc ggctgggatc cggcggccac    300

ctgcacctgc gtatctctcg ggccgccctt cccgaggggc tccccgaggc ctcccgcctt    360

caccgggctc tgttccggct gtccccgacg gcgtcaaggt cgtgggacgt gacacgaccg    420
```

-continued

```
ctgcggcgtc agctcagcct tgcaagaccc caggcgcccg cgctgcacct gcgactgtcg    480

ccgccgccgt cgcagtcgga ccaactgctg gcagaatctt cgtccgcacg gccccagctg    540

gagttgcact tgcggccgca agccgccagg gggcgccgca gagcgcgtgc gcgcaacggg    600

gaccactgtc cgctcgggcc cgggcgttgc tgccgtctgc acacggtccg cgcgtcgctg    660

gaagacctgg gctgggccga ttgggtgctg tcgccacggg aggtgcaagt gaccatgtgc    720

atcggcgcgt gcccgagcca gttccgggcg gcaaacatgc acgcgcagat caagacgagc    780

ctgcaccgcc tgaagcccga cacggtgcca gcgccctgct gcgtgcccgc cagctacaat    840

cccatggtgc tcattcaaaa gaccgacacc ggggtgtcgc tccagaccta tgatgacttg    900

ttagccaaag actgccactg catatga                                        927
```

<210> SEQ ID NO 2
<211> LENGTH: 308
<212> TYPE: PRT
<213> ORGANISM: Homo sapiens

<400> SEQUENCE: 2

```
Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
            20                  25                  30

Ala Glu Ala Ser Arg Ala Ser Phe Pro Gly Pro Ser Glu Leu His Ser
        35                  40                  45

Glu Asp Ser Arg Phe Arg Glu Leu Arg Lys Arg Tyr Glu Asp Leu Leu
    50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
        195                 200                 205

Arg Cys Cys Arg Leu His Thr Val Arg Ala Ser Leu Glu Asp Leu Gly
    210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
                245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
        275                 280                 285
```

```
Asp Thr Gly Val Ser Leu Gln Thr Tyr Asp Asp Leu Leu Ala Lys Asp
    290                 295                 300

Cys His Cys Ile
305


<210> SEQ ID NO 3
<211> LENGTH: 840
<212> TYPE: DNA
<213> ORGANISM: Homo sapiens

<400> SEQUENCE: 3

ctgtctctgg ccgaggcgag ccgcgcaagt ttcccgggac cctcagagtt gcactccgaa     60

gactccagat tccgagagtt gcggaaacgc tacgaggacc tgctaaccag gctgcgggcc    120

aaccagagct gggaagattc gaacaccgac ctcgtcccgg cccctgcagt ccggatactc    180

acgccagaag tgcggctggg atccggcggc cacctgcacc tgcgtatctc tcgggccgcc    240

cttcccgagg ggctccccga ggcctcccgc cttcaccggg ctctgttccg gctgtccccg    300

acggcgtcaa ggtcgtggga cgtgacacga ccgctgcggc gtcagctcag ccttgcaaga    360

ccccaggcgc ccgcgctgca cctgcgactg tcgccgccgc cgtcgcagtc ggaccaactg    420

ctggcagaat cttcgtccgc acggccccag ctggagttgc acttgcggcc gcaagccgcc    480

agggggcgcc gcagagcgcg tgcgcgcaac ggggaccact gtccgctcgg gcccgggcgt    540

tgctgccgtc tgcacacggt ccgcgcgtcg ctggaagacc tgggctgggc cgattgggtg    600

ctgtcgccac gggaggtgca agtgaccatg tgcatcggcg cgtgcccgag ccagttccgg    660

gcggcaaaca tgcacgcgca gatcaagacg agcctgcacc gcctgaagcc cgacacggtg    720

ccagcgccct gctgcgtgcc cgccagctac aatcccatgg tgctcattca aaagaccgac    780

accggggtgt cgctccagac ctatgatgac ttgttagcca aagactgcca ctgcatatga    840


<210> SEQ ID NO 4
<211> LENGTH: 279
<212> TYPE: PRT
<213> ORGANISM: Homo sapiens

<400> SEQUENCE: 4

Leu Ser Leu Ala Glu Ala Ser Arg Ala Ser Phe Pro Gly Pro Ser Glu
1               5                   10                  15

Leu His Ser Glu Asp Ser Arg Phe Arg Glu Leu Arg Lys Arg Tyr Glu
            20                  25                  30

Asp Leu Leu Thr Arg Leu Arg Ala Asn Gln Ser Trp Glu Asp Ser Asn
        35                  40                  45

Thr Asp Leu Val Pro Ala Pro Ala Val Arg Ile Leu Thr Pro Glu Val
    50                  55                  60

Arg Leu Gly Ser Gly Gly His Leu His Leu Arg Ile Ser Arg Ala Ala
65                  70                  75                  80

Leu Pro Glu Gly Leu Pro Glu Ala Ser Arg Leu His Arg Ala Leu Phe
                85                  90                  95

Arg Leu Ser Pro Thr Ala Ser Arg Ser Trp Asp Val Thr Arg Pro Leu
            100                 105                 110

Arg Arg Gln Leu Ser Leu Ala Arg Pro Gln Ala Pro Ala Leu His Leu
        115                 120                 125

Arg Leu Ser Pro Pro Pro Ser Gln Ser Asp Gln Leu Leu Ala Glu Ser
    130                 135                 140

Ser Ser Ala Arg Pro Gln Leu Glu Leu His Leu Arg Pro Gln Ala Ala
```

```
145                 150                 155                 160

Arg Gly Arg Arg Arg Ala Arg Ala Arg Asn Gly Asp His Cys Pro Leu
                165                 170                 175

Gly Pro Gly Arg Cys Cys Arg Leu His Thr Val Arg Ala Ser Leu Glu
            180                 185                 190

Asp Leu Gly Trp Ala Asp Trp Val Leu Ser Pro Arg Glu Val Gln Val
        195                 200                 205

Thr Met Cys Ile Gly Ala Cys Pro Ser Gln Phe Arg Ala Ala Asn Met
    210                 215                 220

His Ala Gln Ile Lys Thr Ser Leu His Arg Leu Lys Pro Asp Thr Val
225                 230                 235                 240

Pro Ala Pro Cys Cys Val Pro Ala Ser Tyr Asn Pro Met Val Leu Ile
                245                 250                 255

Gln Lys Thr Asp Thr Gly Val Ser Leu Gln Thr Tyr Asp Asp Leu Leu
            260                 265                 270

Ala Lys Asp Cys His Cys Ile
        275


<210> SEQ ID NO 5
<211> LENGTH: 339
<212> TYPE: DNA
<213> ORGANISM: Homo sapiens

<400> SEQUENCE: 5

gcgcgcaacg ggaccactg tccgctcggg cccgggcgtt gctgccgtct gcacacggtc      60

cgcgcgtcgc tggaagacct gggctgggcc gattgggtgc tgtcgccacg ggaggtgcaa    120

gtgaccatgt gcatcggcgc gtgcccgagc cagttccggg cggcaaacat gcacgcgcag    180

atcaagacga gcctgcaccg cctgaagccc gacacggtgc cagcgccctg ctgcgtgccc    240

gccagctaca atcccatggt gctcattcaa aagaccgaca ccggggtgtc gctccagacc    300

tatgatgact tgttagccaa agactgccac tgcatatga                           339


<210> SEQ ID NO 6
<211> LENGTH: 112
<212> TYPE: PRT
<213> ORGANISM: Homo sapiens

<400> SEQUENCE: 6

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 7
<211> LENGTH: 912
<212> TYPE: DNA
```

<213> ORGANISM: Mus musculus

<400> SEQUENCE: 7

```
atggccccgc ccgcgctcca ggcccagcct ccaggcggct ctcaactgag gttcctgctg     60

ttcctgctgc tgttgctgct gctgctgtca tggccatcgc agggggacgc cctggcaatg    120

cctgaacagc gaccctccgg ccctgagtcc caactcaacg ccgacgagct acggggtcgc    180

ttccaggacc tgctgagccg gctgcatgcc aaccagagcc gagaggactc gaactcagaa    240

ccaagtcctg acccagctgt ccggatactc agtccagagg tgagattggg gtcccacggc    300

cagctgctac tccgcgtcaa ccgggcgtcg ctgagtcagg gtctccccga agcctaccgc    360

gtgcaccgag cgctgctcct gctgacgccg acggcccgcc cctgggacat cactaggccc    420

ctgaagcgtg cgctcagcct ccggggaccc cgtgctcccg cattacgcct gcgcctgacg    480

ccgcctccgg acctggctat gctgccctct ggcggcacgc agctggaact gcgcttacgg    540

gtagccgccg gcagggggcg ccgaagcgcg catgcgcacc caagagactc gtgcccactg    600

ggtccggggc gctgctgtca cttggagact gtgcaggcaa ctcttgaaga cttgggctgg    660

agcgactggg tgctgtcccc gcgccagctg cagctgagca tgtgcgtggg cgagtgtccc    720

cacctgtatc gctccgcgaa cacgcatgcg cagatcaaag cacgcctgca tggcctgcag    780

cctgacaagg tgcctgcccc gtgctgtgtc ccctccagct acaccccggt ggttcttatg    840

cacaggacag acagtggtgt gtcactgcag acttatgatg acctggtggc ccggggctgc    900

cactgcgctt ga                                                        912
```

<210> SEQ ID NO 8
<211> LENGTH: 303
<212> TYPE: PRT
<213> ORGANISM: Mus musculus

<400> SEQUENCE: 8

```
Met Ala Pro Pro Ala Leu Gln Ala Gln Pro Pro Gly Gly Ser Gln Leu
1               5                   10                  15

Arg Phe Leu Leu Phe Leu Leu Leu Leu Leu Leu Leu Leu Ser Trp Pro
            20                  25                  30

Ser Gln Gly Asp Ala Leu Ala Met Pro Glu Gln Arg Pro Ser Gly Pro
        35                  40                  45

Glu Ser Gln Leu Asn Ala Asp Glu Leu Arg Gly Arg Phe Gln Asp Leu
    50                  55                  60

Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                85                  90                  95

Gly Ser His Gly Gln Leu Leu Leu Arg Val Asn Arg Ala Ser Leu Ser
            100                 105                 110

Gln Gly Leu Pro Glu Ala Tyr Arg Val His Arg Ala Leu Leu Leu Leu
        115                 120                 125

Thr Pro Thr Ala Arg Pro Trp Asp Ile Thr Arg Pro Leu Lys Arg Ala
    130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190
```

```
His Pro Arg Asp Ser Cys Pro Leu Gly Pro Gly Arg Cys Cys His Leu
        195                 200                 205

Glu Thr Val Gln Ala Thr Leu Glu Asp Leu Gly Trp Ser Asp Trp Val
    210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
        275                 280                 285

Leu Gln Thr Tyr Asp Asp Leu Val Ala Arg Gly Cys His Cys Ala
    290                 295                 300


<210> SEQ ID NO 9
<211> LENGTH: 816
<212> TYPE: DNA
<213> ORGANISM: Mus musculus

<400> SEQUENCE: 9

tcgcaggggg acgccctggc aatgcctgaa cagcgaccct ccggccctga gtcccaactc      60

aacgccgacg agctacgggg tcgcttccag gacctgctga gccggctgca tgccaaccag     120

agccgagagg actcgaactc agaaccaagt cctgacccag ctgtccggat actcagtcca     180

gaggtgagat tggggtccca cggccagctg ctactccgcg tcaaccgggc gtcgctgagt     240

cagggtctcc ccgaagccta ccgcgtgcac cgagcgctgc tcctgctgac gccgacggcc     300

cgcccctggg acatcactag gcccctgaag cgtgcgctca gcctccgggg accccgtgct     360

cccgcattac gcctgcgcct gacgccgcct ccggacctgg ctatgctgcc ctctggcggc     420

acgcagctgg aactgcgctt acgggtagcc gccggcaggg ggcgccgaag cgcgcatgcg     480

cacccaagag actcgtgccc actgggtccg ggcgctgct gtcacttgga gactgtgcag      540

gcaactcttg aagacttggg ctggagcgac tgggtgctgt ccccgcgcca gctgcagctg     600

agcatgtgcg tgggcgagtg tccccacctg tatcgctccg cgaacacgca tgcgcagatc     660

aaagcacgcc tgcatggcct gcagcctgac aaggtgcctg ccccgtgctg tgtcccctcc     720

agctacaccc cggtggttct tatgcacagg acagacagtg gtgtgtcact gcagacttat     780

gatgacctgg tggcccgggg ctgccactgc gcttga                               816


<210> SEQ ID NO 10
<211> LENGTH: 271
<212> TYPE: PRT
<213> ORGANISM: Mus musculus

<400> SEQUENCE: 10

Ser Gln Gly Asp Ala Leu Ala Met Pro Glu Gln Arg Pro Ser Gly Pro
1               5                   10                  15

Glu Ser Gln Leu Asn Ala Asp Glu Leu Arg Gly Arg Phe Gln Asp Leu
            20                  25                  30

Leu Ser Arg Leu His Ala Asn Gln Ser Arg Glu Asp Ser Asn Ser Glu
        35                  40                  45

Pro Ser Pro Asp Pro Ala Val Arg Ile Leu Ser Pro Glu Val Arg Leu
    50                  55                  60

Gly Ser His Gly Gln Leu Leu Leu Arg Val Asn Arg Ala Ser Leu Ser
```

65 70 75 80

Gln Gly Leu Pro Glu Ala Tyr Arg Val His Arg Ala Leu Leu Leu Leu
85 90 95

Thr Pro Thr Ala Arg Pro Trp Asp Ile Thr Arg Pro Leu Lys Arg Ala
100 105 110

Leu Ser Leu Arg Gly Pro Arg Ala Pro Ala Leu Arg Leu Arg Leu Thr
115 120 125

Pro Pro Pro Asp Leu Ala Met Leu Pro Ser Gly Gly Thr Gln Leu Glu
130 135 140

Leu Arg Leu Arg Val Ala Ala Gly Arg Gly Arg Arg Ser Ala His Ala
145 150 155 160

His Pro Arg Asp Ser Cys Pro Leu Gly Pro Gly Arg Cys Cys His Leu
165 170 175

Glu Thr Val Gln Ala Thr Leu Glu Asp Leu Gly Trp Ser Asp Trp Val
180 185 190

Leu Ser Pro Arg Gln Leu Gln Leu Ser Met Cys Val Gly Glu Cys Pro
195 200 205

His Leu Tyr Arg Ser Ala Asn Thr His Ala Gln Ile Lys Ala Arg Leu
210 215 220

His Gly Leu Gln Pro Asp Lys Val Pro Ala Pro Cys Cys Val Pro Ser
225 230 235 240

Ser Tyr Thr Pro Val Val Leu Met His Arg Thr Asp Ser Gly Val Ser
245 250 255

Leu Gln Thr Tyr Asp Asp Leu Val Ala Arg Gly Cys His Cys Ala
260 265 270

<210> SEQ ID NO 11
<211> LENGTH: 348
<212> TYPE: DNA
<213> ORGANISM: Mus musculus

<400> SEQUENCE: 11
agcgcgcatg cgcacccaag agactcgtgc ccactgggtc cggggcgctg ctgtcacttg 60
gagactgtgc aggcaactct tgaagacttg ggctggagcg actgggtgct gtccccgcgc 120
cagctgcagc tgagcatgtg cgtgggcgag tgtccccacc tgtatcgctc cgcgaacacg 180
catgcgcaga tcaaagcacg cctgcatggc ctgcagcctg acaaggtgcc tgccccgtgc 240
tgtgtcccct ccagctacac cccggtggtt cttatgcaca ggacagacag tggtgtgtca 300
ctgcagactt atgatgacct ggtggcccgg ggctgccact gcgcttga 348

<210> SEQ ID NO 12
<211> LENGTH: 115
<212> TYPE: PRT
<213> ORGANISM: Mus musculus

<400> SEQUENCE: 12

Ser Ala His Ala His Pro Arg Asp Ser Cys Pro Leu Gly Pro Gly Arg
1 5 10 15

Cys Cys His Leu Glu Thr Val Gln Ala Thr Leu Glu Asp Leu Gly Trp
20 25 30

Ser Asp Trp Val Leu Ser Pro Arg Gln Leu Gln Leu Ser Met Cys Val
35 40 45

Gly Glu Cys Pro His Leu Tyr Arg Ser Ala Asn Thr His Ala Gln Ile
50 55 60

Lys Ala Arg Leu His Gly Leu Gln Pro Asp Lys Val Pro Ala Pro Cys

```
65                  70                  75                  80

Cys Val Pro Ser Ser Tyr Thr Pro Val Val Leu Met His Arg Thr Asp
                85                  90                  95

Ser Gly Val Ser Leu Gln Thr Tyr Asp Asp Leu Val Ala Arg Gly Cys
            100                 105                 110

His Cys Ala
        115


<210> SEQ ID NO 13
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 13

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Met His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105


<210> SEQ ID NO 14
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 14

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110


<210> SEQ ID NO 15
<211> LENGTH: 112
<212> TYPE: PRT
<213> ORGANISM: Artificial Sequence
<220> FEATURE:
```

<223> OTHER INFORMATION: Synthetic Polypeptide

<400> SEQUENCE: 15

Ala Arg Asp Gly Asp His Cys Pro Leu Gly Pro Gly Arg Cys Cys Arg
1 5 10 15

Leu His Thr Val Arg Ala Ser Leu Glu Asp Leu Gly Trp Ala Asp Trp
20 25 30

Val Leu Ser Pro Arg Glu Val Gln Val Thr Met Cys Ile Gly Ala Cys
35 40 45

Pro Ser Gln Phe Arg Ala Ala Asn Met His Ala Gln Ile Lys Thr Ser
50 55 60

Leu His Arg Leu Lys Pro Asp Thr Val Pro Ala Pro Cys Cys Val Pro
65 70 75 80

Ala Ser Tyr Asn Pro Met Val Leu Ile Gln Lys Thr Asp Thr Gly Val
85 90 95

Ser Leu Gln Thr Tyr Asp Asp Leu Leu Ala Lys Asp Cys His Cys Ile
100 105 110

<210> SEQ ID NO 16
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 16

Ala Arg Asn Gly Glu His Cys Pro Leu Gly Pro Gly Arg Cys Cys Arg
1 5 10 15

Leu His Thr Val Arg Ala Ser Leu Glu Asp Leu Gly Trp Ala Asp Trp
20 25 30

Val Leu Ser Pro Arg Glu Val Gln Val Thr Met Cys Ile Gly Ala Cys
35 40 45

Pro Ser Gln Phe Arg Ala Ala Asn Met His Ala Gln Ile Lys Thr Ser
50 55 60

Leu His Arg Leu Lys Pro Asp Thr Val Pro Ala Pro Cys Cys Val Pro
65 70 75 80

Ala Ser Tyr Asn Pro Met Val Leu Ile Gln Lys Thr Asp Thr Gly Val
85 90 95

Ser Leu Gln Thr Tyr Asp Asp Leu Leu Ala Lys Asp Cys His Cys Ile
100 105 110

<210> SEQ ID NO 17
<211> LENGTH: 109
<212> TYPE: PRT
<213> ORGANISM: Artificial Sequence
<220> FEATURE:
<223> OTHER INFORMATION: Synthetic Polypeptide

<400> SEQUENCE: 17

Gly Glu His Cys Pro Leu Gly Pro Gly Arg Cys Cys Arg Leu His Thr
1 5 10 15

Val Arg Ala Ser Leu Glu Asp Leu Gly Trp Ala Asp Trp Val Leu Ser
20 25 30

Pro Arg Glu Val Gln Val Thr Met Cys Ile Gly Ala Cys Pro Ser Gln
35 40 45

Phe Arg Ala Ala Asn Met His Ala Gln Ile Lys Thr Ser Leu His Arg
50 55 60

Leu Lys Pro Asp Thr Val Pro Ala Pro Cys Cys Val Pro Ala Ser Tyr 65 70 75 80

Asn Pro Met Val Leu Ile Gln Lys Thr Asp Thr Gly Val Ser Leu Gln
85 90 95

Thr Tyr Asp Asp Leu Leu Ala Lys Asp Cys His Cys Ile
100 105

<210> SEQ ID NO 18
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 18

Ala Arg Gln Gly Glu His Cys Pro Leu Gly Pro Gly Arg Cys Cys Arg
1 5 10 15

Leu His Thr Val Arg Ala Ser Leu Glu Asp Leu Gly Trp Ala Asp Trp
20 25 30

Val Leu Ser Pro Arg Glu Val Gln Val Thr Met Cys Ile Gly Ala Cys
35 40 45

Pro Ser Gln Phe Arg Ala Ala Asn Met His Ala Gln Ile Lys Thr Ser
50 55 60

Leu His Arg Leu Lys Pro Asp Thr Val Pro Ala Pro Cys Cys Val Pro
65 70 75 80

Ala Ser Tyr Asn Pro Met Val Leu Ile Gln Lys Thr Asp Thr Gly Val
85 90 95

Ser Leu Gln Thr Tyr Asp Asp Leu Leu Ala Lys Asp Cys His Cys Ile
100 105 110

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Gly Gly Gly Gly Ser
1 5

<210> SEQ ID NO 20
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 20

Gly Gly Gly Gly Ser Gly Gly Gly Gly Ser
1 5 10

<210> SEQ ID NO 21
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 21

Gly Gly Gly Gly Ser Gly Gly Gly Gly Ser Gly Gly Gly Gly Ser Gly
1 5 10 15

Gly Gly Gly Ser

```
            20


<210> SEQ ID NO 22
<211> LENGTH: 40
<212> TYPE: PRT
<213> ORGANISM: Artificial Sequence
<220> FEATURE:
<223> OTHER INFORMATION: Synthetic Polypeptide

<400> SEQUENCE: 22

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40


<210> SEQ ID NO 23
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 23

Gly Gly Gly Gly
1


<210> SEQ ID NO 24
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 24

Gly Gly Gly Gly Gln
1               5


<210> SEQ ID NO 25
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 25

Gly Gly Gly Gly Gln Gly Gly Gly Gly Gln Gly Gly Gly Gly Gln Gly
1               5                   10                  15

Gly Gly Gly Gln
            20


<210> SEQ ID NO 26
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 26

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30
```

```
Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215
```

<210> SEQ ID NO 27
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 27

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175
```

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly
210 215

<210> SEQ ID NO 28
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 28

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Cys Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Asp Thr Thr Pro Pro Val Leu Asp Ser Asp Gly Ser Phe Phe Leu
165 170 175

Tyr Ser Asp Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly
210 215

<210> SEQ ID NO 29
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 29

Gly Pro Ser Val Phe Leu Phe Pro Pro Lys Pro Lys Asp Thr Leu Met
1 5 10 15

Ile Ser Arg Thr Pro Glu Val Thr Cys Val Val Val Asp Val Ser His
20 25 30

Glu Asp Pro Glu Val Lys Phe Asn Trp Tyr Val Asp Gly Val Glu Val
35 40 45

```
His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly
    210


<210> SEQ ID NO 30
<211> LENGTH: 210
<212> TYPE: PRT
<213> ORGANISM: Artificial Sequence
<220> FEATURE:
<223> OTHER INFORMATION: Synthetic Polypeptide

<400> SEQUENCE: 30

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190
```

```
His Glu Ala Leu His Asn His Tyr Thr Gln Lys Ser Leu Ser Leu Ser
        195                 200                 205

Pro Gly
    210


<210> SEQ ID NO 31
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 31

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215


<210> SEQ ID NO 32
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 32

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
```

```
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 33
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 33

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
```

```
        195                 200                 205

Lys Ser Leu Ser Leu Ser Pro Gly Lys
    210                 215


<210> SEQ ID NO 34
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 34

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Cys Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 35
<211> LENGTH: 211
<212> TYPE: PRT
<213> ORGANISM: Artificial Sequence
<220> FEATURE:
<223> OTHER INFORMATION: Synthetic Polypeptide

<400> SEQUENCE: 35

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60
```

Arg Val Val Ser Val Leu Thr Val Leu His Gln Asp Trp Leu Asn Gly
65 70 75 80

Lys Glu Tyr Lys Cys Lys Val Ser Asn Lys Ala Leu Pro Ala Pro Ile
85 90 95

Glu Lys Thr Ile Ser Lys Ala Lys Gly Gln Pro Arg Glu Pro Gln Val
100 105 110

Tyr Thr Leu Pro Pro Cys Arg Lys Glu Met Thr Lys Asn Gln Val Ser
115 120 125

Leu Thr Cys Leu Val Lys Gly Phe Tyr Pro Ser Asp Ile Ala Val Glu
130 135 140

Trp Glu Ser Asn Gly Gln Pro Glu Asn Asn Tyr Lys Thr Thr Pro Pro
145 150 155 160

Val Leu Lys Ser Asp Gly Ser Phe Phe Leu Tyr Ser Lys Leu Thr Val
165 170 175

Asp Lys Ser Arg Trp Gln Gln Gly Asn Val Phe Ser Cys Ser Val Met
180 185 190

His Glu Ala Leu His Asn His Tyr Thr Gln Lys Ser Leu Ser Leu Ser
195 200 205

Pro Gly Lys
210

<210> SEQ ID NO 36
<211> LENGTH: 211
<212> TYPE: PRT
<213> ORGANISM: Artificial Sequence
<220> FEATURE:
<223> OTHER INFORMATION: Synthetic Polypeptide

<400> SEQUENCE: 36

Gly Pro Ser Val Phe Leu Phe Pro Pro Lys Pro Lys Asp Thr Leu Met
1 5 10 15

Ile Ser Arg Thr Pro Glu Val Thr Cys Val Val Val Asp Val Ser His
20 25 30

Glu Asp Pro Glu Val Lys Phe Asn Trp Tyr Val Asp Gly Val Glu Val
35 40 45

His Asn Ala Lys Thr Lys Pro Arg Glu Glu Gln Tyr Asn Ser Thr Tyr
50 55 60

Arg Val Val Ser Val Leu Thr Val Leu His Gln Asp Trp Leu Asn Gly
65 70 75 80

Lys Glu Tyr Lys Cys Lys Val Ser Asn Lys Ala Leu Pro Ala Pro Ile
85 90 95

Glu Lys Thr Ile Ser Lys Ala Lys Gly Gln Pro Arg Glu Pro Gln Val
100 105 110

Tyr Thr Leu Pro Pro Ser Arg Lys Glu Met Thr Lys Asn Gln Val Ser
115 120 125

Leu Thr Cys Leu Val Lys Gly Phe Tyr Pro Ser Asp Ile Ala Val Glu
130 135 140

Trp Glu Ser Asn Gly Gln Pro Glu Asn Asn Tyr Lys Thr Thr Pro Pro
145 150 155 160

Val Leu Lys Ser Asp Gly Ser Phe Phe Leu Tyr Ser Lys Leu Thr Val
165 170 175

Asp Lys Ser Arg Trp Gln Gln Gly Asn Val Phe Ser Cys Ser Val Met
180 185 190

His Glu Ala Leu His Asn His Tyr Thr Gln Lys Ser Leu Ser Leu Ser
195 200 205

Pro Gly Lys
210

<210> SEQ ID NO 37
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 37

Ala Pro Glu Ala Ala Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Lys Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Lys Thr Thr Pro Pro Val Leu Lys Ser Asp Gly Ser Phe Phe Leu
165 170 175

Tyr Ser Lys Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Lys
210 215

<210> SEQ ID NO 38
<211> LENGTH: 630
<212> TYPE: PRT
<213> ORGANISM: Artificial Sequence
<220> FEATURE:
<223> OTHER INFORMATION: Fusion Protein

<400> SEQUENCE: 38

Gly Gly Gly Glu Arg Lys Ser Ser Val Glu Cys Pro Pro Cys Pro Ala
1 5 10 15

Pro Pro Val Ala Gly Pro Ser Val Phe Leu Phe Pro Pro Lys Pro Lys
20 25 30

Asp Thr Leu Met Ile Ser Arg Thr Pro Glu Val Thr Cys Val Val Val
35 40 45

Asp Val Ser His Glu Asp Pro Glu Val Gln Phe Asn Trp Tyr Val Asp
50 55 60

Gly Val Glu Val His Asn Ala Lys Thr Lys Pro Arg Glu Glu Gln Phe
65 70 75 80

```
Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Gly Gly Gly Gly Ser Gly Gly Gly Gly Ser
225                 230                 235                 240

Gly Gly Gly Gly Ser Gly Gly Gly Gly Ser Gly Gly Gly Gly Ser Gly
                245                 250                 255

Gly Gly Gly Ser Gly Gly Gly Gly Ser Gly Gly Gly Gly Ser Glu Arg
            260                 265                 270

Lys Ser Ser Val Glu Cys Pro Pro Cys Pro Ala Pro Pro Val Ala Gly
        275                 280                 285

Pro Ser Val Phe Leu Phe Pro Pro Lys Pro Lys Asp Thr Leu Met Ile
    290                 295                 300

Ser Arg Thr Pro Glu Val Thr Cys Val Val Val Asp Val Ser His Glu
305                 310                 315                 320

Asp Pro Glu Val Gln Phe Asn Trp Tyr Val Asp Gly Val Glu Val His
                325                 330                 335

Asn Ala Lys Thr Lys Pro Arg Glu Glu Gln Phe Asn Ser Thr Phe Arg
            340                 345                 350

Val Val Ser Val Leu Thr Val Val His Gln Asp Trp Leu Asn Gly Lys
        355                 360                 365

Glu Tyr Lys Cys Lys Val Ser Asn Lys Gly Leu Pro Ala Pro Ile Glu
    370                 375                 380

Lys Thr Ile Ser Lys Thr Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Met
        435                 440                 445

Leu Asp Ser Asp Gly Ser Phe Phe Leu Tyr Ser Lys Leu Thr Val Asp
    450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495
```

Gly Ser Gly Gly Gly Gly Ser Gly Gly Gly Gly Ser Gly Gly Gly Gly
500 505 510

Ser Gly Gly Gly Gly Ser Ala Arg Asn Gly Asp His Cys Pro Leu Gly
515 520 525

Pro Gly Arg Cys Cys Arg Leu His Thr Val Arg Ala Ser Leu Glu Asp
530 535 540

Leu Gly Trp Ala Asp Trp Val Leu Ser Pro Arg Glu Val Gln Val Thr
545 550 555 560

Met Cys Ile Gly Ala Cys Pro Ser Gln Phe Arg Ala Ala Asn Met His
565 570 575

Ala Gln Ile Lys Thr Ser Leu His Arg Leu Lys Pro Asp Thr Val Pro
580 585 590

Ala Pro Cys Cys Val Pro Ala Ser Tyr Asn Pro Met Val Leu Ile Gln
595 600 605

Lys Thr Asp Thr Gly Val Ser Leu Gln Thr Tyr Asp Asp Leu Leu Ala
610 615 620

Lys Asp Cys His Cys Ile
625 630

<210> SEQ ID NO 39
<211> LENGTH: 348
<212> TYPE: PRT
<213> ORGANISM: Artificial Sequence
<220> FEATURE:
<223> OTHER INFORMATION: Fusion Protein

<400> SEQUENCE: 39

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Asp Thr Thr Pro Pro Val Leu Asp Ser Asp Gly Ser Phe Phe Leu
165 170 175

Tyr Ser Asp Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Gly Gly Gly Gly Ser Gly Gly Gly
210 215 220

```
Gly Ser Gly Gly Gly Gly Ser Gly Gly Gly Gly Ser Ala Arg Asn Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345


<210> SEQ ID NO 40
<211> LENGTH: 332
<212> TYPE: PRT
<213> ORGANISM: Artificial Sequence
<220> FEATURE:
<223> OTHER INFORMATION: Fusion Protein

<400> SEQUENCE: 40

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Lys Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Lys Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Gly Ala Arg Asn Gly
    210                 215                 220

Asp His Cys Pro Leu Gly Pro Gly Arg Cys Cys Arg Leu His Thr Val
225                 230                 235                 240
```

```
Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330


<210> SEQ ID NO 41
<211> LENGTH: 325
<212> TYPE: PRT
<213> ORGANISM: Artificial Sequence
<220> FEATURE:
<223> OTHER INFORMATION: Fusion Protein

<400> SEQUENCE: 41

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Asp His Cys Pro Leu Gly Pro
    210                 215                 220

Gly Arg Cys Cys Arg Leu His Thr Val Arg Ala Ser Leu Glu Asp Leu
225                 230                 235                 240

Gly Trp Ala Asp Trp Val Leu Ser Pro Arg Glu Val Gln Val Thr Met
                245                 250                 255

Cys Ile Gly Ala Cys Pro Ser Gln Phe Arg Ala Ala Asn Met His Ala
            260                 265                 270
```

Gln Ile Lys Thr Ser Leu His Arg Leu Lys Pro Asp Thr Val Pro Ala
275 280 285

Pro Cys Cys Val Pro Ala Ser Tyr Asn Pro Met Val Leu Ile Gln Lys
290 295 300

Thr Asp Thr Gly Val Ser Leu Gln Thr Tyr Asp Asp Leu Leu Ala Lys
305 310 315 320

Asp Cys His Cys Ile
325

<210> SEQ ID NO 42
<211> LENGTH: 328
<212> TYPE: PRT
<213> ORGANISM: Artificial Sequence
<220> FEATURE:
<223> OTHER INFORMATION: Fusion Protein

<400> SEQUENCE: 42

Ala Pro Glu Leu Leu Gly Gly Pro Ser Val Phe Leu Phe Pro Pro Lys
1 5 10 15

Pro Lys Asp Thr Leu Met Ile Ser Arg Thr Pro Glu Val Thr Cys Val
20 25 30

Val Val Asp Val Ser His Glu Asp Pro Glu Val Lys Phe Asn Trp Tyr
35 40 45

Val Asp Gly Val Glu Val His Asn Ala Lys Thr Lys Pro Arg Glu Glu
50 55 60

Gln Tyr Asn Ser Thr Tyr Arg Val Val Ser Val Leu Thr Val Leu His
65 70 75 80

Gln Asp Trp Leu Asn Gly Lys Glu Tyr Lys Cys Lys Val Ser Asn Lys
85 90 95

Ala Leu Pro Ala Pro Ile Glu Lys Thr Ile Ser Lys Ala Lys Gly Gln
100 105 110

Pro Arg Glu Pro Gln Val Tyr Thr Leu Pro Pro Ser Arg Glu Glu Met
115 120 125

Thr Lys Asn Gln Val Ser Leu Thr Cys Leu Val Lys Gly Phe Tyr Pro
130 135 140

Ser Asp Ile Ala Val Glu Trp Glu Ser Asn Gly Gln Pro Glu Asn Asn
145 150 155 160

Tyr Asp Thr Thr Pro Pro Val Leu Asp Ser Asp Gly Ser Phe Phe Leu
165 170 175

Tyr Ser Asp Leu Thr Val Asp Lys Ser Arg Trp Gln Gln Gly Asn Val
180 185 190

Phe Ser Cys Ser Val Met His Glu Ala Leu His Asn His Tyr Thr Gln
195 200 205

Lys Ser Leu Ser Leu Ser Pro Gly Ala Arg Asp Gly Asp His Cys Pro
210 215 220

Leu Gly Pro Gly Arg Cys Cys Arg Leu His Thr Val Arg Ala Ser Leu
225 230 235 240

Glu Asp Leu Gly Trp Ala Asp Trp Val Leu Ser Pro Arg Glu Val Gln
245 250 255

Val Thr Met Cys Ile Gly Ala Cys Pro Ser Gln Phe Arg Ala Ala Asn
260 265 270

Met His Ala Gln Ile Lys Thr Ser Leu His Arg Leu Lys Pro Asp Thr
275 280 285

Val Pro Ala Pro Cys Cys Val Pro Ala Ser Tyr Asn Pro Met Val Leu
290 295 300

```
Ile Gln Lys Thr Asp Thr Gly Val Ser Leu Gln Thr Tyr Asp Asp Leu
305                 310                 315                 320

Leu Ala Lys Asp Cys His Cys Ile
                325


<210> SEQ ID NO 43
<211> LENGTH: 325
<212> TYPE: PRT
<213> ORGANISM: Artificial Sequence
<220> FEATURE:
<223> OTHER INFORMATION: Fusion Protein

<400> SEQUENCE: 43

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Asp His Cys Pro Leu Gly Pro
    210                 215                 220

Gly Arg Cys Cys Arg Leu His Thr Val Arg Ala Ser Leu Glu Asp Leu
225                 230                 235                 240

Gly Trp Ala Asp Trp Val Leu Ser Pro Arg Glu Val Gln Val Thr Met
                245                 250                 255

Cys Ile Gly Ala Cys Pro Ser Gln Phe Arg Ala Ala Asn Met His Ala
            260                 265                 270

Gln Ile Lys Thr Ser Leu His Arg Leu Lys Pro Asp Thr Val Pro Ala
        275                 280                 285

Pro Cys Cys Val Pro Ala Ser Tyr Asn Pro Met Val Leu Ile Gln Lys
    290                 295                 300

Thr Asp Thr Gly Val Ser Leu Gln Thr Tyr Asp Asp Leu Leu Ala Lys
305                 310                 315                 320

Asp Cys His Cys Ile
                325
```

```
<210> SEQ ID NO 44
<211> LENGTH: 328
<212> TYPE: PRT
<213> ORGANISM: Artificial Sequence
<220> FEATURE:
<223> OTHER INFORMATION: Fusion Protein

<400> SEQUENCE: 44

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Cys Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Ala Arg Asp Gly Asp His Cys Pro
    210                 215                 220

Leu Gly Pro Gly Arg Cys Cys Arg Leu His Thr Val Arg Ala Ser Leu
225                 230                 235                 240

Glu Asp Leu Gly Trp Ala Asp Trp Val Leu Ser Pro Arg Glu Val Gln
                245                 250                 255

Val Thr Met Cys Ile Gly Ala Cys Pro Ser Gln Phe Arg Ala Ala Asn
            260                 265                 270

Met His Ala Gln Ile Lys Thr Ser Leu His Arg Leu Lys Pro Asp Thr
        275                 280                 285

Val Pro Ala Pro Cys Cys Val Pro Ala Ser Tyr Asn Pro Met Val Leu
    290                 295                 300

Ile Gln Lys Thr Asp Thr Gly Val Ser Leu Gln Thr Tyr Asp Asp Leu
305                 310                 315                 320

Leu Ala Lys Asp Cys His Cys Ile
                325


<210> SEQ ID NO 45
<211> LENGTH: 319
<212> TYPE: PRT
<213> ORGANISM: Artificial Sequence
<220> FEATURE:
```

<223> OTHER INFORMATION: Fusion Protein

<400> SEQUENCE: 45

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Glu His Cys Pro Leu Gly Pro Gly Arg Cys Cys Arg Leu
    210                 215                 220

His Thr Val Arg Ala Ser Leu Glu Asp Leu Gly Trp Ala Asp Trp Val
225                 230                 235                 240

Leu Ser Pro Arg Glu Val Gln Val Thr Met Cys Ile Gly Ala Cys Pro
                245                 250                 255

Ser Gln Phe Arg Ala Ala Asn Met His Ala Gln Ile Lys Thr Ser Leu
            260                 265                 270

His Arg Leu Lys Pro Asp Thr Val Pro Ala Pro Cys Cys Val Pro Ala
        275                 280                 285

Ser Tyr Asn Pro Met Val Leu Ile Gln Lys Thr Asp Thr Gly Val Ser
    290                 295                 300

Leu Gln Thr Tyr Asp Asp Leu Leu Ala Lys Asp Cys His Cys Ile
305                 310                 315
```

<210> SEQ ID NO 46
<211> LENGTH: 322
<212> TYPE: PRT
<213> ORGANISM: Artificial Sequence
<220> FEATURE:
<223> OTHER INFORMATION: Fusion Protein

<400> SEQUENCE: 46

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30
```

```
Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Cys Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Glu His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile
```

<210> SEQ ID NO 47
<211> LENGTH: 322
<212> TYPE: PRT
<213> ORGANISM: Artificial Sequence
<220> FEATURE:
<223> OTHER INFORMATION: Fusion Protein

<400> SEQUENCE: 47

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60
```

```
Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Glu His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile
```

<210> SEQ ID NO 48
<211> LENGTH: 342
<212> TYPE: PRT
<213> ORGANISM: Artificial Sequence
<220> FEATURE:
<223> OTHER INFORMATION: Fusion Protein

<400> SEQUENCE: 48

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
```

```
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Gln Gly Gly Gly Gly Gln Gly Gly Gly Gly
    210                 215                 220

Gln Gly Gly Gly Gly Gln Ala Arg Asn Gly Asp His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340


<210> SEQ ID NO 49
<211> LENGTH: 342
<212> TYPE: PRT
<213> ORGANISM: Artificial Sequence
<220> FEATURE:
<223> OTHER INFORMATION: Fusion Protein

<400> SEQUENCE: 49

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
```

```
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Gln Gly Gly Gly Gly Gln Gly Gly Gly Gly
    210                 215                 220

Gln Gly Gly Gly Gly Gln Ala Arg Gln Gly Asp His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340
```

<210> SEQ ID NO 50
<211> LENGTH: 342
<212> TYPE: PRT
<213> ORGANISM: Artificial Sequence
<220> FEATURE:
<223> OTHER INFORMATION: Fusion Protein

<400> SEQUENCE: 50

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
```

```
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Gln Gly Gly Gly Gly Gln Gly Gly Gly Gly
    210                 215                 220

Gln Gly Gly Gly Gly Gln Ala Arg Gln Gly Glu His Cys Pro Leu Gly
225                 230                 235                 240

Pro Gly Arg Cys Cys Arg Leu His Thr Val Arg Ala Ser Leu Glu Asp
                245                 250                 255

Leu Gly Trp Ala Asp Trp Val Leu Ser Pro Arg Glu Val Gln Val Thr
            260                 265                 270

Met Cys Ile Gly Ala Cys Pro Ser Gln Phe Arg Ala Ala Asn Met His
        275                 280                 285

Ala Gln Ile Lys Thr Ser Leu His Arg Leu Lys Pro Asp Thr Val Pro
    290                 295                 300

Ala Pro Cys Cys Val Pro Ala Ser Tyr Asn Pro Met Val Leu Ile Gln
305                 310                 315                 320

Lys Thr Asp Thr Gly Val Ser Leu Gln Thr Tyr Asp Asp Leu Leu Ala
                325                 330                 335

Lys Asp Cys His Cys Ile
            340


<210> SEQ ID NO 51
<211> LENGTH: 332
<212> TYPE: PRT
<213> ORGANISM: Artificial Sequence
<220> FEATURE:
<223> OTHER INFORMATION: Fusion Protein

<400> SEQUENCE: 51

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
```

```
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Gly Gly Gly Gly Ser Ala Arg Gln Gly
    210                 215                 220

Asp His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330


<210> SEQ ID NO 52
<211> LENGTH: 332
<212> TYPE: PRT
<213> ORGANISM: Artificial Sequence
<220> FEATURE:
<223> OTHER INFORMATION: Fusion Protein

<400> SEQUENCE: 52

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
```

```
            180                 185                 190

His Glu Ala Leu His Asn His Tyr Thr Gln Lys Ser Leu Ser Leu Ser
        195                 200                 205

Pro Gly Gly Gly Gly Gly Ser Gly Gly Gly Gly Ser Ala Arg Gln Gly
    210                 215                 220

Glu His Cys Pro Leu Gly Pro Gly Arg Cys Cys Arg Leu His Thr Val
225                 230                 235                 240

Arg Ala Ser Leu Glu Asp Leu Gly Trp Ala Asp Trp Val Leu Ser Pro
                245                 250                 255

Arg Glu Val Gln Val Thr Met Cys Ile Gly Ala Cys Pro Ser Gln Phe
            260                 265                 270

Arg Ala Ala Asn Met His Ala Gln Ile Lys Thr Ser Leu His Arg Leu
        275                 280                 285

Lys Pro Asp Thr Val Pro Ala Pro Cys Cys Val Pro Ala Ser Tyr Asn
    290                 295                 300

Pro Met Val Leu Ile Gln Lys Thr Asp Thr Gly Val Ser Leu Gln Thr
305                 310                 315                 320

Tyr Asp Asp Leu Leu Ala Lys Asp Cys His Cys Ile
                325                 330
```

<210> SEQ ID NO 53
<211> LENGTH: 327
<212> TYPE: PRT
<213> ORGANISM: Artificial Sequence
<220> FEATURE:
<223> OTHER INFORMATION: Fusion Protein

<400> SEQUENCE: 53

```
Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Ala Arg Gln Gly Asp His Cys Pro Leu
```

```
    210                 215                 220

Gly Pro Gly Arg Cys Cys Arg Leu His Thr Val Arg Ala Ser Leu Glu
225                 230                 235                 240

Asp Leu Gly Trp Ala Asp Trp Val Leu Ser Pro Arg Glu Val Gln Val
                245                 250                 255

Thr Met Cys Ile Gly Ala Cys Pro Ser Gln Phe Arg Ala Ala Asn Met
            260                 265                 270

His Ala Gln Ile Lys Thr Ser Leu His Arg Leu Lys Pro Asp Thr Val
        275                 280                 285

Pro Ala Pro Cys Cys Val Pro Ala Ser Tyr Asn Pro Met Val Leu Ile
    290                 295                 300

Gln Lys Thr Asp Thr Gly Val Ser Leu Gln Thr Tyr Asp Asp Leu Leu
305                 310                 315                 320

Ala Lys Asp Cys His Cys Ile
                325


<210> SEQ ID NO 54
<211> LENGTH: 327
<212> TYPE: PRT
<213> ORGANISM: Artificial Sequence
<220> FEATURE:
<223> OTHER INFORMATION: Fusion Protein

<400> SEQUENCE: 54

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Gly Gly Gly Gly Ser Ala Arg Gln Gly Glu His Cys Pro Leu
    210                 215                 220

Gly Pro Gly Arg Cys Cys Arg Leu His Thr Val Arg Ala Ser Leu Glu
225                 230                 235                 240

Asp Leu Gly Trp Ala Asp Trp Val Leu Ser Pro Arg Glu Val Gln Val
```

```
                245                 250                 255

Thr Met Cys Ile Gly Ala Cys Pro Ser Gln Phe Arg Ala Ala Asn Met
            260                 265                 270

His Ala Gln Ile Lys Thr Ser Leu His Arg Leu Lys Pro Asp Thr Val
        275                 280                 285

Pro Ala Pro Cys Cys Val Pro Ala Ser Tyr Asn Pro Met Val Leu Ile
    290                 295                 300

Gln Lys Thr Asp Thr Gly Val Ser Leu Gln Thr Tyr Asp Asp Leu Leu
305                 310                 315                 320

Ala Lys Asp Cys His Cys Ile
                325


<210> SEQ ID NO 55
<211> LENGTH: 322
<212> TYPE: PRT
<213> ORGANISM: Artificial Sequence
<220> FEATURE:
<223> OTHER INFORMATION: Fusion Protein

<400> SEQUENCE: 55

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Ala Leu Pro Ala Pro Ile
                85                  90                  95

Glu Lys Thr Ile Ser Lys Ala Lys Gly Gln Pro Arg Glu Pro Gln Val
            100                 105                 110

Tyr Thr Leu Pro Pro Ser Arg Glu Glu Met Thr Lys Asn Gln Val Ser
        115                 120                 125

Leu Thr Cys Leu Val Lys Gly Phe Tyr Pro Ser Asp Ile Ala Val Glu
    130                 135                 140

Trp Glu Ser Asn Gly Gln Pro Glu Asn Asn Tyr Asp Thr Thr Pro Pro
145                 150                 155                 160

Val Leu Asp Ser Asp Gly Ser Phe Phe Leu Tyr Ser Asp Leu Thr Val
                165                 170                 175

Asp Lys Ser Arg Trp Gln Gln Gly Asn Val Phe Ser Cys Ser Val Met
            180                 185                 190

His Glu Ala Leu His Asn His Tyr Thr Gln Lys Ser Leu Ser Leu Ser
        195                 200                 205

Pro Gly Ala Arg Gln Gly Asp His Cys Pro Leu Gly Pro Gly Arg Cys
    210                 215                 220

Cys Arg Leu His Thr Val Arg Ala Ser Leu Glu Asp Leu Gly Trp Ala
225                 230                 235                 240

Asp Trp Val Leu Ser Pro Arg Glu Val Gln Val Thr Met Cys Ile Gly
                245                 250                 255

Ala Cys Pro Ser Gln Phe Arg Ala Ala Asn Met His Ala Gln Ile Lys
            260                 265                 270

Thr Ser Leu His Arg Leu Lys Pro Asp Thr Val Pro Ala Pro Cys Cys
```

```
        275                 280                 285

Val Pro Ala Ser Tyr Asn Pro Met Val Leu Ile Gln Lys Thr Asp Thr
    290                 295                 300

Gly Val Ser Leu Gln Thr Tyr Asp Asp Leu Leu Ala Lys Asp Cys His
305                 310                 315                 320

Cys Ile


<210> SEQ ID NO 56
<211> LENGTH: 348
<212> TYPE: PRT
<213> ORGANISM: Artificial Sequence
<220> FEATURE:
<223> OTHER INFORMATION: Fusion Protein

<400> SEQUENCE: 56

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Gly Gln Gly Gly Gly
    210                 215                 220

Gly Gln Gly Gly Gly Gly Gln Gly Gly Gly Gly Gln Ala Arg Gln Gly
225                 230                 235                 240

Asp His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320
```

```
Pro Met Val Leu Ile Gln Lys Thr Asp Thr Gly Val Ser Leu Gln Thr
                325                 330                 335

Tyr Asp Asp Leu Leu Ala Lys Asp Cys His Cys Ile
            340                 345


<210> SEQ ID NO 57
<211> LENGTH: 348
<212> TYPE: PRT
<213> ORGANISM: Artificial Sequence
<220> FEATURE:
<223> OTHER INFORMATION: Fusion Protein

<400> SEQUENCE: 57

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Asp Thr Thr Pro Pro Val Leu Asp Ser Asp Gly Ser Phe Phe Leu
                165                 170                 175

Tyr Ser Asp Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Gly Gly Gly Gly Gln Gly Gly Gly
    210                 215                 220

Gly Gln Gly Gly Gly Gly Gln Gly Gly Gly Gly Gln Ala Arg Gln Gly
225                 230                 235                 240

Glu His Cys Pro Leu Gly Pro Gly Arg Cys Cys Arg Leu His Thr Val
                245                 250                 255

Arg Ala Ser Leu Glu Asp Leu Gly Trp Ala Asp Trp Val Leu Ser Pro
            260                 265                 270

Arg Glu Val Gln Val Thr Met Cys Ile Gly Ala Cys Pro Ser Gln Phe
        275                 280                 285

Arg Ala Ala Asn Met His Ala Gln Ile Lys Thr Ser Leu His Arg Leu
    290                 295                 300

Lys Pro Asp Thr Val Pro Ala Pro Cys Cys Val Pro Ala Ser Tyr Asn
305                 310                 315                 320

Pro Met Val Leu Ile Gln Lys Thr Asp Thr Gly Val Ser Leu Gln Thr
                325                 330                 335
```

```
Tyr Asp Asp Leu Leu Ala Lys Asp Cys His Cys Ile
            340                 345


<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Gly Gly Gly Gly Ala
1               5
```

USE OF GDF15 FOR TREATING CARDIOMETABOLIC SYNDROME AND OTHER CONDITIONS

RELATED APPLICATIONS

This application is a U.S. national stage filing under 35 U.S.C. § 371 of PCT Application No. PCT/US20/53884, filed on Oct. 2, 2020, which claims the benefit of U.S. Provisional Application No. 62/910,661, filed on Oct. 4, 2019, both of which are hereby incorporated by reference in its entirety.

SEQUENCE LISTING

The present application is being filed along with a Sequence Listing in electronic format. The Sequence Listing is provided as a file entitled A-2453-WO-PCT_ST25.txt, created Sep. 30, 2020, which is 109 kb in size. The information in the electronic format of the Sequence Listing is incorporated herein by reference in its entirety.

BACKGROUND

Growth differentiation factor 15 (GDF15), also referred to as macrophage inhibitory cytokine 1 (MIC1) (Bootcov M R, 1997, *Proc Natl Acad Sci* 94:11514-9), placental bone morphogenetic factor (PLAB) (Hromas R 1997, *Biochim Biophys Acta.* 1354:40-4), placental transforming growth factor beta (PTGFB) (Lawton L N 1997, *Gene.* 203:17-26), prostate derived factor (PDF) (Paralkar V M 1998, *J Biol Chem.* 273:13760-7), and nonsteroidal anti-inflammatory drug-activated gene (NAG-1) (Baek S J 2001, *J Biol Chem.* 276: 33384-92), is a secreted protein that circulates in plasma as an ~25 kDa homodimer. GDF15 binds to GDNF family receptor α-like (GFRAL) with high affinity. GDF15-induced cell signaling is believed to require the interaction of GFRAL with the coreceptor RET. GDF15 has been linked to multiple biological activities. Elevated GDF15 has been shown to be correlated with weight loss and administration of GDF15 has been shown to reduce food intake and body weight.

Cardiometabolic syndrome (CMS), a combination of impaired metabolism (insulin resistance, impaired glucose tolerance, dyslipidemia), obesity, hypertension, renal insufficiency and cardiovascular diseases (CVD), is now recognized as a disease entity by the World Health Organization and the American Society of Endocrinology. Comorbidities, such as obesity and diabetes mellitus, are key factors of metabolic risk and are associated with the progressive left ventricular (LV) remodeling and dysfunction observed in heart failure with preserved ejection fraction (HFpEF). The incidence of HFpEF (currently 50% of heart failure) continues to rise, and its prognosis fails to improve partly due to the lack of a specific HFpEF therapy. An important step in the development of novel therapeutic agents against CMS is the establishment of a translational preclinical model, that represents a cluster of cardiometabolic disturbances.

Accordingly, there is a need for a translational preclinical model of CMS, as well as treatment therapies for treating CMS and other conditions, such as heart failure. The present disclosure meets these needs and provide related advantages.

SUMMARY

Provided herein is a method of treating a heart condition in a subject comprising administering a GDF15 molecule. Also provided is a method of treating a cardiac condition or cardiovascular disease. In some embodiments, the heart condition is heart failure. In some embodiments, the heart failure is heart failure with preserved ejection fraction (HFpEF).

Also provided is a method of treating a subject with cardiometabolic syndrome comprising administering a GDF15 molecule. In some embodiments, the subject is obese, has impaired metabolism, pancreatic dysfunction, hypertension, diastolic dysfunction, HFpEF, decreased exercise capacity, or renal dysfunction.

In some embodiments, after treatment with the GDF15 molecule, the subject has a decreased heart weight, improved exercise capacity, or change in the level of adiponectin, sE-selectin, sICAM, Myl3, osteopontin, TIMP1, VEGF, or vWF, after treatment with the GDF15 molecule. In some embodiments, the level of adiponectin is increased. In some embodiments, the level of sE-selectin, sICAM, Myl3, osteopontin, TIMP1, VEGF, vWF, or any combination thereof is decreased. In yet other embodiments, the subject has decreased heart to brain weight ratio, left ventricle (LV) mass, cardiac output, stroke volume, or % ejection fraction echocardiographic, after treatment with the GDF15 molecule.

In some embodiments, the GDF15 molecule is a GDF15-Fc fusion protein. The fusion protein can comprise a GDF15 region joined to an Fc region. In some embodiments, the GDF15 region is joined to the Fc via a linker.

DETAILED DESCRIPTION

Figure 1B:
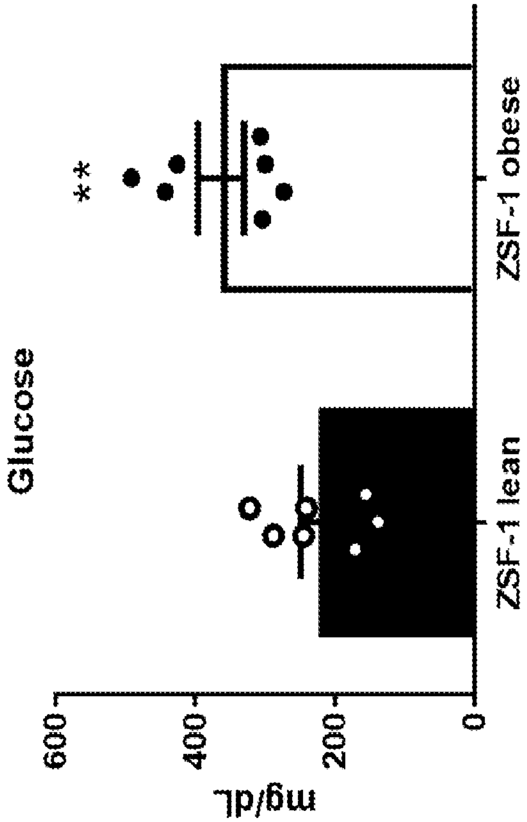
FIG. 1. ZSF1 obese male rats at the age of 20 weeks exhibit impaired metabolism by increased body weight (FIG. 1A), elevated blood glucose (FIG. 1B), insulin (FIG. 1C), cholesterol (FIG. 1D) and triglyceride levels (FIG. 1E), statistically significant decrease in adiponectin (FIG. 1F) and increase in GDF15 levels (FIG. 1G). Stars (*) indicate significance (* p<0.05,  p<0.01, * p<0.001, **** p<0.0001), unpaired two-tailed t-test.
Figure 1A:
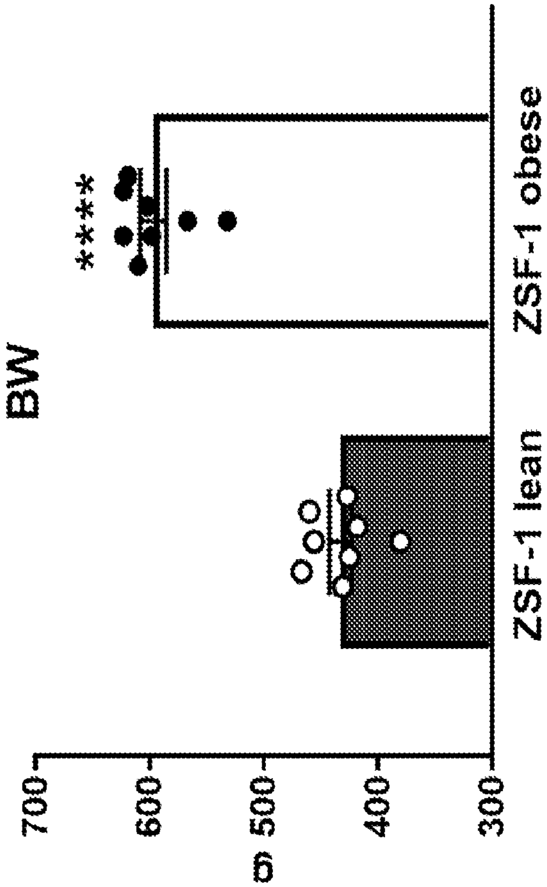
Figure 1C:
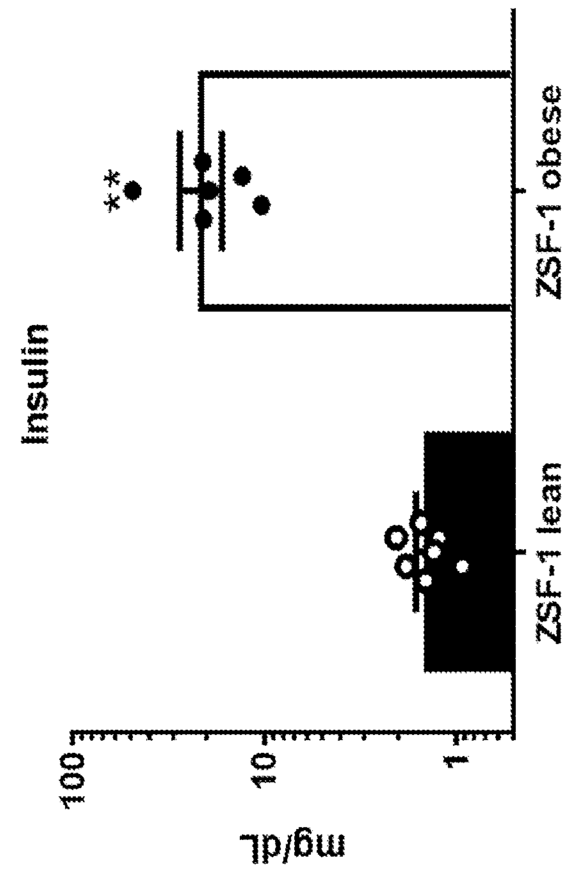
Figure 1D:
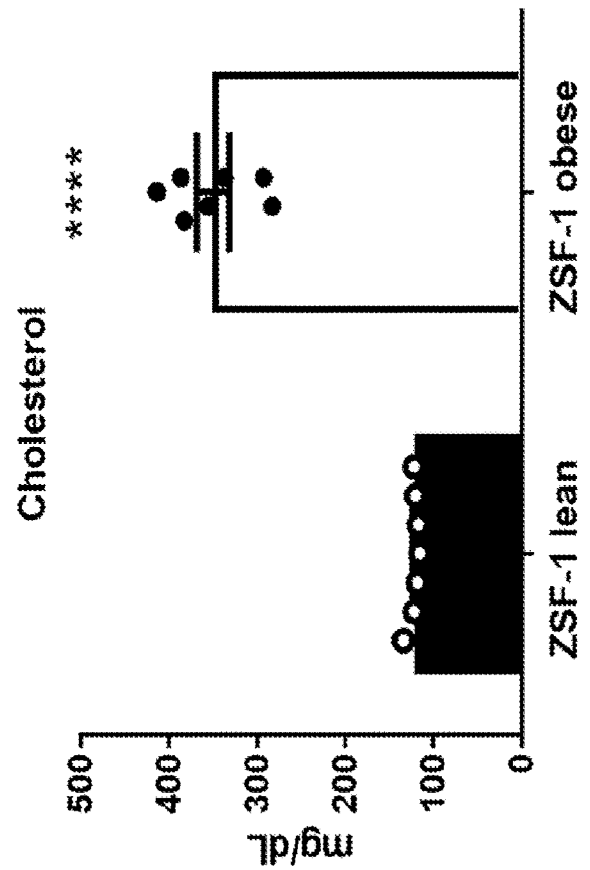
Figure 1E:
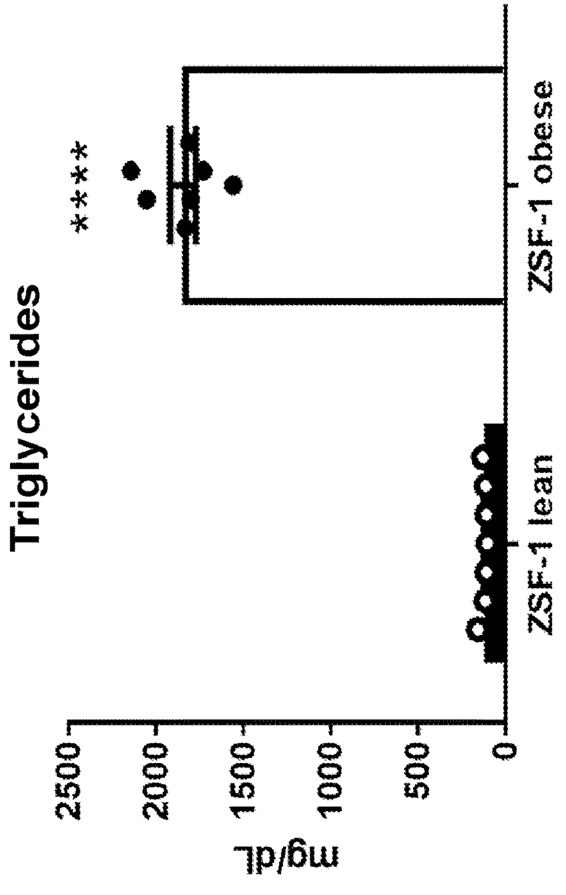
Figure 1F:
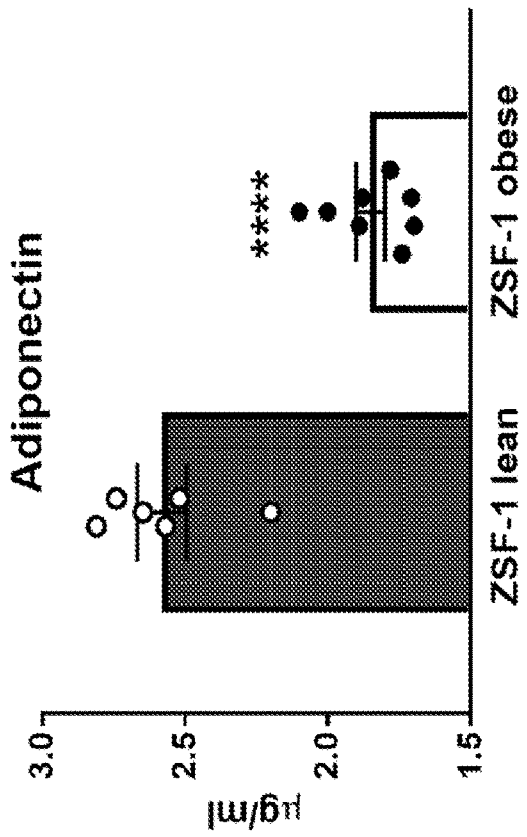
Figure 1G:
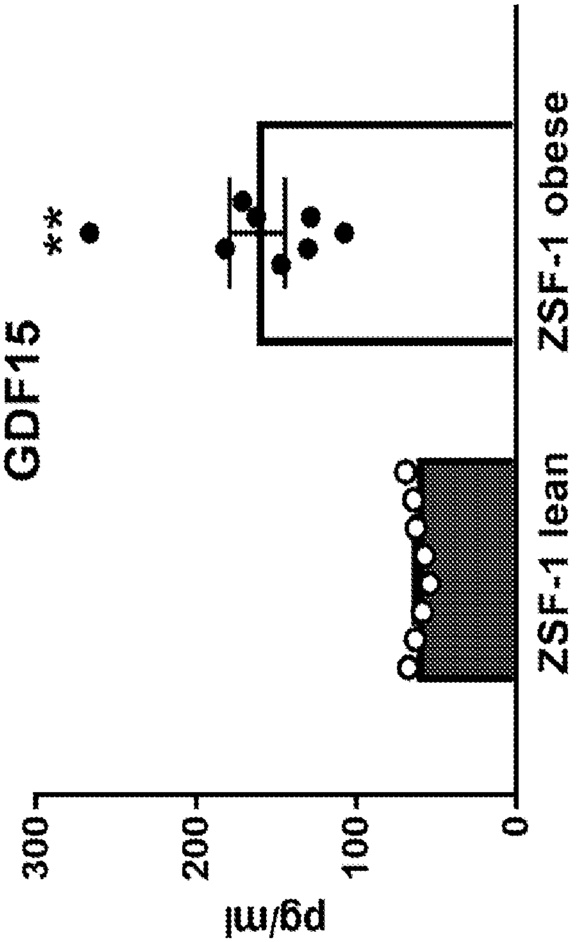

Provided herein is a method of treating a heart condition in a subject comprising administering a GDF15 molecule. Also provided is a method of treating a cardiac condition or cardiovascular disease. In some embodiments, the heart condition is heart failure. In some embodiments, the heart failure is heart failure with preserved ejection fraction (HFpEF).

Also provided is a method of treating a subject with cardiometabolic syndrome comprising administering a GDF15 molecule. In some embodiments, the subject is obese, has impaired metabolism, pancreatic dysfunction, hypertension, diastolic dysfunction, HFpEF, decreased exercise capacity, or renal dysfunction.

In some embodiments, after treatment with the GDF15 molecule, the subject has a decreased heart weight, improved exercise capacity, or change in the level of adiponectin, sE-selectin, sICAM, Myl3, osteopontin, TIMP1, VEGF, or vWF, after treatment with the GDF15 molecule. In some embodiments, the level of adiponectin is increased. In some embodiments, the level of sE-selectin, sICAM, Myl3, osteopontin, TIMP1, VEGF, vWF, or any combination thereof is decreased. In yet other embodiments, the subject has decreased heart to brain weight ratio, left ventricle (LV) mass, cardiac output, stroke volume, or % ejection fraction echocardiographic, after treatment with the GDF15 molecule.

In some embodiments, the GDF15 molecule is a GDF15-Fc fusion protein. The fusion protein can comprise a GDF15 region joined to an Fc region. In some embodiments, the GDF15 region is joined to the Fc via a linker. In some embodiments, the GDF15 region comprises wild type GDF15. Both the human and murine GDF15 have a signal peptide and prodomain. The nucleotide sequence for full length human GDF15 is:

(SEQ ID NO: 1)

```
atgcccgggc aagaactcag gacggtgaat ggctctcaga
tgctcctggt gttgctggtg ctctcgtggc tgccgcatgg
gggcgccctg tctctggccg aggcgagccg cgcaagtttc
ccgggaccct cagagttgca ctccgaagac tccagattcc
gagagttgcg gaaacgctac gaggacctgc taaccaggct
gcgggccaac cagagctggg aagattcgaa caccgacctc
gtcccggccc ctgcagtccg gatactcacg ccagaagtgc
ggctgggatc cggcggccac ctgcacctgc gtatctctcg
ggccgccctt cccgaggggc tccccgaggc ctcccgcctt
caccgggctc tgttccggct gtccccgacg gcgtcaaggt
cgtgggacgt gacacgaccg ctgcggcgtc agctcagcct
tgcaagaccc caggcgcccg cgctgcacct gcgactgtcg
ccgccgccgt cgcagtcgga ccaactgctg gcagaatctt
cgtccgcacg gccccagctg gagttgcact tgcggccgca
agccgccagg gggcgccgca gagcgcgtgc gcgcaacggg
gaccactgtc cgctcgggcc cgggcgttgc tgccgtctgc
acacggtccg cgcgtcgctg gaagacctgg gctgggccga
ttgggtgctg tcgccacggg aggtgcaagt gaccatgtgc
atcggcgcgt gcccgagcca gttccgggcg gcaaacatgc
acgcgcagat caagacgagc ctgcaccgcc tgaagcccga
cacggtgcca gcgccctgct gcgtgcccgc cagctacaat
```

-continued cccatggtgc tcattcaaaa gaccgacacc ggggtgtcgc tccagaccta tgatgacttg ttagccaaag actgccactg catatga The amino acid sequence for full length human GDF15 (308 amino acids) is:

(SEQ ID NO: 2)

MPGQELRTVNGSQMLLVLLVLSWLPHGGALSLAEASRASFPGPSELHSE

DSRFRELRKRYEDLLTRLRANQSWEDSNTDLVPAPAVRILTPEVRLGSG

GHLHLRISRAALPEGLPEASRLHRALFRLSPTASRSWDVTRPLRRQLSL

ARPQAPALHLRLSPPPSQSDQLLAESSSARPQLELHLRPQAARGRRRAR

ARNGDHCPLGPGRCCRLHTVRASLEDLGWADWVLSPREVQVTMCIGACP

SQFRAANMHAQIKTSLHRLKPDTVPAPCCVPASYNPMVLIQKTDTGVSL

QTYDDLLAKDCHCI

The nucleotide sequence for human GDF15 without its signal sequence is:

(SEQ ID NO: 3)

ctgtctctgg ccgaggcgag ccgcgcaagt ttcccgggac cctcagagtt gcactccgaa gactccagat tccgagagtt gcggaaacgc tacgaggacc tgctaaccag gctgcgggcc aaccagagct gggaagattc gaacaccgac ctcgtcccgg cccctgcagt ccggatactc acgccagaag tgcggctggg atccggcggc cacctgcacc tgcgtatctc tcgggccgcc cttcccgagg ggctccccga ggcctcccgc cttcaccggg ctctgttccg gctgtccccg acggcgtcaa ggtcgtggga cgtgacacga ccgctgcggc gtcagctcag ccttgcaaga ccccaggcgc ccgcgctgca cctgcgactg tcgccgccgc cgtcgcagtc ggaccaactg ctggcagaat cttcgtccgc acggccccag ctggagttgc acttgcggcc gcaagccgcc agggggcgcc gcagagcgcg tgcgcgcaac ggggaccact gtccgctcgg gcccgggcgt tgctgccgtc tgcacacggt ccgcgcgtcg ctggaagacc tgggctgggc cgattgggtg ctgtcgccac gggaggtgca agtgaccatg tgcatcggcg cgtgcccgag ccagttccgg gcggcaaaca tgcacgcgca gatcaagacg agcctgcacc gcctgaagcc cgacacggtg ccagcgccct gctgcgtgcc cgccagctac aatcccatgg tgctcattca aaagaccgac accggggtgt cgctccagac ctatgatgac ttgttagcca aagactgcca ctgcatatga The amino acid sequence for human GDF15 without its 29 amino acid signal sequence (279 amino acids) is:

(SEQ ID NO: 4)

LSLAEASRASFPGPSELHSEDSRFRELRKRYEDLL

TRLRANQSWEDSNTDLVPAPAVRILTPEVRLGSGG

HLHLRISRAALPEGLPEASRLHRALFRLSPTASRS

WDVTRPLRRQLSLARPQAPALHLRLSPPPSQSDQL

LAESSSARPQLELHLRPQAARGRRRARARNGDHCP

LGPGRCCRLHTVRASLEDLGWADWVLSPREVQVTM

CIGACPSQFRAANMHAQIKTSLHRLKPDTVPAPCC

VPASYNPMVLIQKTDTGVSLQTYDDLLAKDCHCI

The nucleotide sequence for human GDF15 without its signal peptide or prodomain is:

(SEQ ID NO: 5)

gcgcgcaacggggaccactgtccgctcgggcccgg gcgttgctgccgtctgcacacggtccgcgcgtcgc tggaagacctgggctgggccgattgggtgctgtcg ccacgggaggtgcaagtgaccatgtgcatcggcgc gtgcccgagccagttccgggcggcaaacatgcacg cgcagatcaagacgagcctgcaccgcctgaagccc gacacggtgccagcgccctgctgcgtgcccgccag ctacaatcccatggtgctcattcaaaagaccgaca ccggggtgtcgctccagacctatgatgacttgtta gccaaagactgccactgcatatga The amino acid sequence for human GDF15 without its signal peptide or prodomain (the active domain of GDF15 of 112 amino acids) is:

(SEQ ID NO: 6)

ARNGDHCPLGPGRCCRLHTVRASLEDLGWADWVLS

PREVQVTMCIGACPSQFRAANMHAQIKTSLHRLKP

DTVPAPCCVPASYNPMVLIQKTDTGVSLQTYDDLL

AKDCHCI

The nucleotide sequence for full length murine GDF15 is:

(SEQ ID NO: 7)

atggccccgc ccgcgctcca ggcccagcct ccaggcggct ctcaactgag gttcctgctg ttcctgctgc tgttgctgct gctgctgtca tggccatcgc agggggacgc cctggcaatg cctgaacagc gaccctccgg ccctgagtcc caactcaacg ccgacgagct acggggtcgc ttccaggacc tgctgagccg gctgcatgcc aaccagagcc gagaggactc gaactcagaa ccaagtcctg acccagctgt ccggatactc agtccagagg tgagattggg gtcccacggc cagctgctac -continued

```
tccgcgtcaa ccgggcgtcg ctgagtcagg gtctccccga
agcctaccgc gtgcaccgag cgctgctcct gctgacgccg
acggcccgcc cctgggacat cactaggccc ctgaagcgtg
cgctcagcct ccggggaccc cgtgctcccg cattacgcct
gcgcctgacg ccgcctccgg acctggctat gctgccctct
ggcggcacgc agctggaact gcgcttacgg
gtagccgccg gcagggggcg ccgaagcgcg catgcgcacc
caagagactc gtgcccactg ggtccggggc gctgctgtca
cttggagact gtgcaggcaa ctcttgaaga cttgggctgg
agcgactggg tgctgtcccc gcgccagctg cagctgagca
tgtgcgtggg cgagtgtccc cacctgtatc gctccgcgaa
cacgcatgcg cagatcaaag cacgcctgca tggcctgcag
cctgacaagg tgcctgcccc gtgctgtgtc ccctccagct
acaccccggt ggttcttatg cacaggacag acagtggtgt
gtcactgcag acttatgatg acctggtggc ccggggctgc
cactgcgctt ga
```

The amino acid sequence for full length murine GDF15 (303 amino acids) is:

(SEQ ID NO: 8)

```
MAPPALQAQPPGGSQLRFLLFLLLLLLLLSWPSQG
DALAMPEQRPSGPESQLNADELRGRFQDLLSRLHA
NQSREDSNSEPSPDPAVRILSPEVRLGSHGQLLLR
VNRASLSQGLPEAYRVHRALLLLTPTARPWDITRP
LKRALSLRGPRAPALRLRLTPPPDLAMLPSGGTQL
ELRLRVAAGRGRRSAHAHPRDSCPLGPGRCCHLET
VQATLEDLGWSDWVLSPRQLQLSMCVGECPHLYRS
ANTHAQIKARLHGLQPDKVPAPCCVPSSYTPVVLM
HRTDSGVSLQTYDDLVARGCHCA
```

The nucleotide sequence for murine GDF15 without its signal sequence is:

(SEQ ID NO: 9)

```
tcgcagggggacgccctggcaatgcctgaacagcg
accctccggccctgagtcccaactcaacgccgacg
agctacggggtcgcttccaggacctgctgagccgg
ctgcatgccaaccagagccgagaggactcgaactc
agaaccaagtcctgacccagctgtccggatactca
gtccagaggtgagattggggtcccacggccagctg
ctactccgcgtcaaccgggcgtcgctgagtcaggg
tctccccgaagcctaccgcgtgcaccgagcgctgc
tcctgctgacgccgacggcccgcccctgggacatc
```

-continued

```
actaggcccctgaagcgtgcgctcagcctccgggg
accccgtgctcccgcattacgcctgcgcctgacgc
cgcctccggacctggctatgctgccctctggcggc
acgcagctggaactgcgcttacgggtagccgccgg
cagggggcgccgaagcgcgcatgcgcacccaagag
actcgtgcccactgggtccggggcgctgctgtcac
ttggagactgtgcaggcaactcttgaagacttggg
ctggagcgactgggtgctgtccccgcgccagctgc
agctgagcatgtgcgtgggcgagtgtccccacctg
tatcgctccgcgaacacgcatgcgcagatcaaagc
acgcctgcatggcctgcagcctgacaaggtgcctg
ccccgtgctgtgtcccctccagctacaccccggtg
gttcttatgcacaggacagacagtggtgtgtcact
gcagacttatgatgacctggtggcccggggctgcc
actgcgcttga
```

The amino acid sequence for murine GDF15 without its 32 amino acid signal sequence (271 amino acids) is:

(SEQ ID NO: 10)

```
SQGDALAMPEQRPSGPESQLNADELRGRFQDLLSR
LHANQSREDSNSEPSPDP AVRILSPEVRLGSHGQ
LLLRVNRASLSQGLPEAYRVHRALLLLTPTARPWD
ITRPLKRALSLRGPRAPALRLRLTPPPDLAMLPSG
GTQLELRLRVAAGRGRRSAHAHPRDSCPLGPGRCC
HLETVQATLEDLGWSDWVLSPRQLQLSMCVGECPH
LYRSANTHAQIKARLHGLQPDKVPAPCCVPSSYTP
VVLMHRTDSGVSLQTYDDLVARGCHCA
```

The nucleotide sequence for murine GDF15 without its signal sequence or prodomain is:

(SEQ ID NO: 11)

```
agcgcgcatgcgcacccaagagactcgtgcccact
gggtccggggcgctgctgtcacttggagactgtgc
aggcaactcttgaagacttgggctggagcgactgg
gtgctgtccccgcgccagctgcagctgagcatgtg
cgtgggcgagtgtccccacctgtatcgctccgcga
acacgcatgcgcagatcaaagcacgcctgcatggc
ctgcagcctgacaaggtgcctgccccgtgctgtgt
cccctccagctacaccccggtggttcttatgcaca
ggacagacagtggtgtgtcactgcagacttatgat
gacctggtggcccggggctgccactgcgcttga
```

The amino acid sequence for murine GDF15 without its signal peptide or prodomain (active domain of 115 amino acids) is:

(SEQ ID NO: 12)
SAHAHPRDSCPLGPGRCCHLETVQATLEDLGWSDW

VLSPRQLQLSMCVGECPHLYRSANTHAQIKARLHG

LQPDKVPAPCCVPSSYTPVVLMHRTDSGVSLQTYD

DLVARGCHCA

In some embodiments, the GDF15 molecule comprises a GDF15 region comprising an active domain of GDF15, e.g., GDF15 without its signal peptide or prodomain. In some embodiments, the GDF15 region comprises the amino acid sequence of SEQ ID NO: 6 or 12. In some embodiments, the GDF15 region comprises a GDF15 sequence with one or more mutations, such as at least one mutation in the active domain of GDF15. In particular embodiments, the mutation or mutations do not reduce or eliminate the activity of GDF15. In some embodiments, the GDF15 region comprises a mutation in the active domain of human GDF15. In one embodiment, the mutation is a deletion of the first three amino acids of the active domain, such as "GDF15(Δ3)" which is an active domain of human GDF15 in which the first three amino acids removed (i.e., SEQ ID NO: 13).

In some embodiments, the GDF15 region comprises a mutation of the asparagine at position 3 (N3) of the active domain of human GDF15 (SEQ ID NO: 6). An N3 mutation can refer to the mutation of the asparagine residue at position 3 of SEQ ID NO: 6 or the mutation of an asparagine residue corresponding to the asparagine at position 3 of SEQ ID NO: 6 in a GDF15 amino acid sequence. In some embodiments, the asparagine at position 3 is mutated to glutamine (N3Q) or aspartate (N3D). Accordingly, in some embodiments, the GDF15 molecule comprises a GDF15 region of GDF15 (N3Q), which has the amino acid sequence of SEQ ID NO: 14. In other embodiments, the GDF15 molecule comprises a GDF15 region of GDF15(N3D), which has the amino acid sequence of SEQ ID NO: 15. In some embodiments, the GDF15 region comprises a mutation of the aspartate at position 5 (D5) of the active domain of human GDF15 (SEQ ID NO: 6). A D5 mutation can refer to the mutation of the aspartate residue at position 5 of SEQ ID NO: 6 or the mutation of an aspartate residue corresponding to the aspartate at position 5 of SEQ ID NO: 6 in a GDF15 amino acid sequence. In one embodiment, the aspartate at position 5 is mutated to glutamate (D5E). Accordingly, in some embodiments, the GDF15 molecule comprises a GDF15 region of GDF15(D5E), which has the amino acid sequence of SEQ ID NO: 16.

In yet other embodiments, the GDF15 region comprises a combination of mutations, such as a combination of Δ3 and D5 mutations, e.g., GDF15(Δ3/D5E) (SEQ ID NO: 17) or a combination of N3 and D5 mutations, e.g., GDF15(N3D/D5E) or GDF15(N3Q/D5E). In, the GDF15 region comprises the amino acid sequence of SEQ ID NO: 18.

Table 1 provides examples of GDF15 regions that can be used in the GDF15 molecules.

TABLE 1

GDF15 Regions

| SEQ ID NO: | Designation | Sequence |
|---|---|---|
| 6 | GDF15 | ARNGDHCPLGPGRCCRLHTV<br>RASLEDLVGWADWVLSPREV<br>QTMCIGACPSQFRAANMHAQ<br>IKTSLHRLKPDTVPAPCCVP<br>ASYNPMVLIQKTDTGVSLQT<br>YDDLLAKDCHCI |
| 13 | GDF15(Δ3) | GDHCPLGPGRCCRLHTVRAS<br>LEDLGWADWVLSPREVQVTM<br>CIGACPSQFRAANMHAQIKT<br>SLHRLKPDTVPAPCCVPASY<br>NPMVLIQKTDTGVSLQTYDD<br>LLAKDCHCI |
| 14 | GDF15(N3Q) | ARQGDHCPLGPGRCCRLHTV<br>RASLEDLGWADWVLSPREVQ<br>VTMCIGACPSQFRAANMHAQ<br>IKTSLHRLKPDTVPAPCCVP<br>ASYNPMVLIQKTDTGVSLQT<br>YDDLLAKDCHCI |
| 15 | GDF15(N3D) | ARDGDHCPLGPGRCCRLHTV<br>RASLEDLGWADWVLSPREVQ<br>VTMCIGACPSQFRAANMHAQ<br>IKTSLHRLKPDTVPAPCCVP<br>ASYNPMVLIQKTDTGVSLQT<br>YDDLLAKDCHCI |
| 16 | GDF15(D5E) | ARNGEHCPLGPGRCCRLHTV<br>RASLEDLGWADWVLSPREVQ<br>VTMCIGACPSQFRAANMHAQ<br>IKTSLHRLKPDTVPAPCCVP<br>ASYNPMVLIQKTDTGVSLQT<br>YDDLLAKDCHCI |
| 17 | GDF15<br>(Δ3/D5E) | GEHCPLGPGRCCRLHTVRAS<br>LEDLGWADWVLSPREVQVTM<br>CIGACPSQFRAANMHAQIKT<br>SLHRLKPDTVPAPCCVPASY<br>NPMVLIQKTDTGVSLQTYDD<br>LLAKDCHCI |
| 18 | GDF15<br>(N3Q/D5E) | ARQGEHCPLGPGRCCRLHTV<br>RASLEDLGWADWVLSPREVQ<br>VTMCIGACPSQFRAANMHAQ<br>IKTSLHRLKPDTVPAPCCVP<br>ASYNPMVLIQKTDTGVSLQT<br>YDDLLAKDCHCI |

In some embodiments, the GDF15 molecule is fused to an Fc directly. In other embodiments, the Fc is fused to the GDF15 molecule via a linker. In some embodiments, the linker is a G4S (SEQ ID NO: 19) linker. In other embodiments, the linker is a G4Q (SEQ ID NO: 24) linker. The linker can be a (G4S)n or (G4Q)n linker, wherein n is greater than 0. In some embodiments, the fusion protein has a linker that is a G4A (SEQ ID NO: 58) linker, such as a (G4A)n linker, wherein n is greater than 0. In some embodiments, n is 1 or 2. In some embodiments, n is greater than 2, such as 3, 4, 5, 6, 7, or 8. In some embodiments, the linker comprises the amino acid sequence of SEQ ID NO: 19, 20, 21, 22, 23, 24, 25 or 58, as shown in Table 2.

TABLE 2

| Linkers | | |
|---|---|---|
| SEQ ID NO: | Designation | Sequence |
| 19 | G4S | GGGGS |
| 20 | (G4S)2 | GGGGSGGGGS |
| 21 | (G4S)4 | GGGGSGGGGSGGGGSGGGGS |
| 22 | (G4S)8 | GGGGSGGGGSGGGGSGGGGS GGGGSGGGGSGGGGSGGGGS |
| 23 | G4 | GGGG |
| 24 | G4Q | GGGGQ |
| 25 | (G4Q)4 | GGGGQGGGGQGGGGQGGGGQ |
| 58 | G4A | GGGGA |

In some embodiments, the GDF15 molecule comprises an Fc region. The Fc region can comprise or be derived from the Fc domain of a heavy chain of an antibody. In some embodiments, the Fc region may comprise an Fc domain with a mutation, such as a charged pair mutation, a mutation in a glycosylation site or the inclusion of an unnatural amino acid. The Fc region can be derived from a human IgG constant domain of IgG1, IgG2, IgG3 or IgG4. In some embodiments, the Fc region comprises the constant domain of an IgA, IgD, IgE, and IgM heavy chain.

In some embodiments, the Fc region comprises an Fc domain with a charged pair mutation. By introducing a mutation resulting in a charged Fc region, the GDF15 molecule can dimerize with a corresponding Fc molecule having the opposite charge. For example, an aspartate-to-lysine mutation (E356K, wherein 356 is the position using EU numbering, and corresponds to the positions as noted in Tables 3-5) and a glutamate-to-lysine mutation (D399K wherein 399 is the position using EU numbering, and corresponds to positions as noted in Tables 3-5) can be introduced into the Fc region that is joined to a GDF15 region, optionally via a linker, resulting in a positively charged Fc region for the GDF15 molecule. Lysine-to-aspartate mutations (K392D, K409D; wherein 392 and 409 are the positions using EU numbering and corresponds to the positions as noted in Tables 3-5) can be introduced into an Fc domain of a separate molecule, resulting in a negatively charged Fc molecule. The aspartate residues in the negatively charged Fc molecule can associate with the lysine residues of the positively charged Fc region of the GDF15 molecule through electrostatic force, facilitating formation of Fc heterodimers between the Fc region of the GDF15 molecule and the Fc molecule, while reducing or preventing formation of Fc homodimers between the Fc regions of the GDF15 molecules or between Fc molecules.

In some embodiments, one or more lysine-to-aspartate mutations (K392D, K409D) are introduced into the Fc region that is joined to a GDF15 region, optionally via a linker and an aspartate-to-lysine mutation (E356K) and a glutamate-to-lysine mutation (D399K) is introduced into the Fc domain of another molecule. The aspartate residues in the Fc region of the GDF15 molecule can associate with the lysine residues of the Fc molecule through electrostatic force, facilitating formation of Fc heterodimers between the Fc region of the GDF15 molecule and the Fc molecule, and reducing or preventing formation of Fc homodimers between the Fc regions of the GDF15 molecules or between Fc molecules.

In some embodiments, the GDF15 molecule comprises an Fc region comprising an Fc domain with a mutated hinge region. In some embodiments, the Fc domain comprises a deletion in the hinge. In some embodiments, ten amino acids from the hinge are deleted, e.g., FcΔ10. In other embodiments, sixteen amino acids from the hinge are deleted, e.g., FcΔ16. In some embodiments, the Fc domain comprises a hinge deletion (e.g., FcΔ10 or FcΔ16) and a charged pair mutation, such that the Fc domain is positively or negatively charged. For example, the Fc domain can comprise a ten-amino acid deletion in the hinge and lysine-to-aspartate mutations (K392D, K409D), such as FcΔ10(−). In another embodiment, the Fc domain can comprise a ten-amino acid deletion in the hinge and an aspartate-to-lysine mutation (E356K) and a glutamate-to-lysine mutation (D399K), such as an FcΔ10(+). In another embodiment, the Fc domain can comprise a sixteen-amino acid deletion in the hinge and lysine-to-aspartate mutations (K392D, K409D), such as FcΔ16(−). In another embodiment, the Fc domain can comprise a sixteen-amino acid deletion in the hinge and an aspartate-to-lysine mutation (E356K) and a glutamate-to-lysine mutation (D399K), such as an FcΔ16(+).

In some embodiments, an Fc molecule comprising a hinge deletion and a charged pair mutation heterodimerizes with such a GDF15 molecule. For example, the Fc molecule can have a hinge deletion and charged pair mutation that complements the hinge deletion and charged pair mutation of the Fc region of a GDF15 molecule. For example, an Fc molecule can comprise an Fc domain with a ten-amino acid deletion in the hinge and lysine-to-aspartate mutations (K392D, K409D), such as FcΔ10(−), which can optionally comprise a C-terminal lysine (e.g., FcΔ10(−, K)). The Fc molecule can heterodimerize with a GDF15 molecule that comprises an FcΔ10(+). In another embodiment, the Fc molecule can comprise a ten-amino acid deletion in the hinge and an aspartate-to-lysine mutation (E356K) and a glutamate-to-lysine mutation (D399K), such as an FcΔ10(+), which can optionally comprise a C-terminal lysine (e.g., FcΔ10(+, K)). The Fc molecule can heterodimerize with a GDF15 molecule that comprises an FcΔ10(−). In another embodiment, the Fc molecule can comprise a sixteen-amino acid deletion in the hinge and lysine-to-aspartate mutations (K392D, K409D), such as FcΔ16(−), which can optionally comprise a C-terminal lysine (e.g., FcΔ16(−, K)). The Fc molecule which can heterodimerize with a GDF15 molecule that comprises an FcΔ16(+). In another embodiment, the Fc molecule can comprise a sixteen-amino acid deletion in the hinge and an aspartate-to-lysine mutation (E356K) and a glutamate-to-lysine mutation (D399K), such as an FcΔ16(+), which can optionally comprise a C-terminal lysine (e.g., FcΔ16(−, K)). The Fc molecule can heterodimerize with a GDF15 molecule that comprises an FcΔ16(−).

In some embodiments, the Fc region or Fc molecule comprises an Fc domain with an L234A and/or L235A mutation, wherein 234 and 235 are the positions using EU numbering and corresponds to the positions as noted in Tables 3-5. The Fc domain can comprise an L234A mutation, an L235A mutation, a charged pair mutation, a hinge deletion, or any combination thereof. In some embodiments, the Fc domain comprises both an L234A mutation and an L235A mutation. In some embodiments, the Fc domain comprises a hinge deletion, an L234A mutation, an L235A mutation, and a charged pair mutation, such as FcΔ10(+, L234A/L235A), FcΔ10(−, L234A/L235A), FcΔ16(+, L234A/L235A), or FcΔ16(−, L234A/L235A). In some embodiments, the Fc domain comprises an optional C-terminal lysine, e.g., FcΔ10(+,K,L234A/L235A), FcΔ10(−,K, L234A/L235A), FcΔ16(+,K,L234A/L235A), or FcΔ16(−,K, L234A/L235A).

In some embodiments, the Fc region or Fc molecule comprises an Fc domain with a "cysteine clamp." A cysteine clamp mutation involves the introduction of a cysteine into the Fc domain at a specific location through mutation so that when incubated with another Fc domain that also has a cysteine introduced at a specific location through mutation, a disulfide bond (cysteine clamp) may be formed between the two Fc domains (e.g., between an FcΔ16 (+) domain having a "cysteine clamp" mutation and an FcΔ16(−) domain having a "cysteine clamp" mutation). The cysteine can be introduced into the CH3 domain of an Fc domain. In some embodiments, an Fc domain may contain one or more such cysteine clamp mutations. In one embodiment, a cysteine clamp is provided by introducing a serine to cysteine mutation (S354C, wherein 354 is the position using EU numbering, and corresponds to the position as noted in Tables 3-5) into a first Fc domain and a tyrosine to cysteine mutation (Y349C, wherein 349 is the position using EU numbering, and corresponds to the position as noted in Tables 3-5) into a second Fc domain. In one embodiment, a GDF15 molecule comprises an Fc region comprising an Fc domain with a cysteine clamp, a negatively charged pair mutation and a sixteen-amino acid hinge deletion (e.g., GDF15-FcΔ16(−,CC)), and an Fc molecule comprising an Fc domain comprising a cysteine clamp, a positively charged pair mutation and a sixteen-amino acid hinge deletion, and an optional C-terminal lysine (e.g., FcΔ16(+,K, CC)). The cysteine clamp may augment the heterodimerization of the GDF-Fc molecule with the Fc molecule.

Examples of Fc regions that can be used in a GDF15 molecule are shown in Table 3.

TABLE 3

Fc Regions

| SEQ ID NO: | Designation | Sequence |
|---|---|---|
| 26 | FcΔ10(−) | APELLGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSREEMTKNQVSLTCLVK GFYPSDIAVEWESNGQPENN YDTTPPVLDSDGSFFLYSDL TVDKSRWQQGNVFSCSVMHE ALHNHYTQKSLSLSPG Underlined and bolded residues are K392D and K409D mutations. |
| 27 | FcΔ10(+) | APELLGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSRKEMTKNQVSLTCLVK GFYPSDIAVEWESNGQPENN YKTTPPVLKSDGSFFLYSKL TVDKSRWQQGNVFSCSVMHE ALHNHYTQKSLSLSPG Underlined and bolded residues are E356K and D399K mutations. |

TABLE 3-continued

Fc Regions

| SEQ ID NO: | Designation | Sequence |
|---|---|---|
| 28 | FcΔ10 (−, CC) | APELLGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVCT LPPSREEMTKNQVSLTCLVK GFYPSDIAVEWESNGQPENN YDTTPPVLDSDGSFFLYSDL TVDKSRWQQGNVFSCSVMHE ALHNHYTQKSLSLSPG Underlined and italicized residue is Y349C mutation; underlined and bolded residues are K392D and K409D mutations. |
| 29 | FcΔ16 (−, CC) | GPSVFLFPPKPKDTLMISRT PEVTCVVVDVSHEDPEVKFN WYVDGVEVHNAKTKPREEQY NSTYRVVSVLTVLHQDWLNG KEYKCKVSNKALPAPIEKTI SKAKGQPREPQVCTLPPSRE EMTKNQVSLTCLVKGFYPSD IAVEWESNGQPENNYDTTPP VLDSDGSFFLYSDLTVDKSR WQQGNVFSCSVMHEALHNHY TQKSLSLSPG Underlined and italicized residue is Y349C mutation; underlined and bolded residues are K392D and K409D mutations. |
| 30 | FcΔ16(−) | GPSVFLFPPKPKDTLMISRT PEVTCVVVDVSHEDPEVKFN WYVDGVEVHNAKTKPREEQY NSTYRVVSVLTVLHQDWLNG KEYKCKVSNKALPAPIEKTI SKAKGQPREPQVYTLPPSRE EMTKNQVSLTCLVKGFYPSD IAVEWESNGQPENNYDTTPP VLDSDGSFFLYSDLTVDKSR WQQGNVFSCSVMHEALHNHY TQKSLSLSPG Underlined and bolded residues are K392D and K409D mutations. |
| 31 | FcΔ10 (−, L234A/ L235A) | APEAAGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSREEMTKNQVSLTCLVK GFYPSDIAVEWESNGQPENN YDTTPPVLDSDGSFFLYSDL TVDKSRWQQGNVFSCSVMHE ALHNHYTQKSLSLSPG Underlined and italicized residues are L234A and L235A mutations; underlined and bolded residues are K392D and K409D mutations. |

Examples of Fc molecules are shown in Table 4, in which the C-terminal lysine is optional.

TABLE 4

| SEQ ID NO: | Designation | Sequence |
|---|---|---|
| 32 | FcΔ10(+, K) | APELLGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSRKEMTKNQVSLTCLVK GFYPSDIAVEWESNGQPENN YKTTPPVLKSDGSFFLYSKL TVDKSRWQQGNVFSCSVMHE ALHNHYTQKSLSLSPGK Underlined and bolded residues are E356K and D399K mutations. |
| 33 | FcΔ10(−, K) | APELLGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSREEMTKNQVSLTCLVK GFYPSDIAVEWESNGQPENN YDTTPPVLDSDGSFFLYSDL TVDKSRWQQGNVFSCSVMHE ALHNHYTQKSLSLSPGK Underlined and bolded residues are K392D and K409D mutations. |
| 34 | FcΔ10(+, K, CC) | APELLGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPCRKEMTKNQVSLTCLVK GFYPSDIAVEWESNGQPENN YKTTPPVLKSDGSFFLYSKL TVDKSRWQQGNVFSCSVMHE ALHNHYTQKSLSLSPGK Underlined and italicized residue is S354C mutation; underlined and bolded residues are E356K and D399K mutations. |
| 35 | FcΔ16(+, K, CC) | GPSVFLFPPKPKDTLMISRT PEVTCVVVDVSHEDPEVKFN WYVDGVEVHNAKTKPREEQY NSTYRVVSVLTVLHQDWLNG KEYKCKVSNKALPAPIEKTI SKAKGQPREPQVYTLPPCRK EMTKNQVSLTCLVKGFYPSD IAVEWESNGQPENNYKTTPP VLKSDGSFFLYSKLTVDKSR WQQGNVFSCSVMHEALHNHY TQKSLSLSPGK Underlined and italicized residue is S354C mutation; underlined and bolded residues are E356K and D399K mutations. |

TABLE 4-continued

| SEQ ID NO: | Designation | Sequence |
|---|---|---|
| 36 | FcΔ16(+, K) | GPSVFLFPPKPKDTLMISRT PEVTCVVVDVSHEDPEVKFN WYVDGVEVHNAKTKPREEQY NSTYRVVSVLTVLHQDWLNG KEYKCKVSNKALPAPIEKTI SKAKGQPREPQVYTLPPSRK EMTKNQVSLTCLVKGFYPSD IAVEWESNGQPENNYKTTPP VLKSDGSFFLYSKLTVDKSR WQQGNVFSCSVMHEALHNHY TQKSLSLSPGK Underlined and bolded residues are E356K and D399K mutations. |
| 37 | FcΔ10(+, K, L234A/L235A) | APEAAGGPSVFLFPPKPKDT LMISRTPEVTCVVVDVSHED PEVKFNWYVDGVEVHNAKTK PREEQYNSTYRVVSVLTVLH QDWLNGKEYKCKVSNKALPA PIEKTISKAKGQPREPQVYT LPPSRKEMTKNQVSLTCLVK GFYPSDIAVEWESNGQPENN YKTTPPVLKSDGSFFLYSKL TVDKSRWQQGNVFSCSVMHE ALHNHYTQKSLSLSPGK Underlined and italicized residues are L234A and L235A mutations; underlined and bolded residues are E356K and D399K mutations. |

The Fc molecules can be used to dimerize with a molecule comprising a complementary Fc domain. For example, an Fc molecule of FcΔ10(+,K) can dimerize with a molecule comprising an Fc region comprising a ten-amino acid hinge deletion and a negatively charged pair mutation such as FcΔ10(−) (e.g., a GDF15 molecule comprising an Fc region of FcΔ10(−)). An Fc molecule of FcΔ10(−,K) can dimerize with a molecule comprising an Fc region comprising a ten-amino acid hinge deletion and a negatively charged pair mutation such as FcΔ10(+) (e.g., a GDF15 molecule comprising an Fc region of FcΔ10(+)).

An Fc molecule of FcΔ10(+,K,CC) can dimerize with a molecule comprising an Fc region comprising a ten-amino acid hinge deletion and a negatively charged pair mutation such as FcΔ10(−,CC) (e.g., a GDF15 molecule comprising an Fc region of FcΔ10(−, CC)). An Fc molecule of FcΔ16(+,K,CC) can dimerize with a molecule comprising an Fc region comprising a ten-amino acid hinge deletion and a negatively charged pair mutation such as FcΔ16(−, CC) (e.g., a GDF15 molecule comprising an Fc region of FcΔ16(−, CC)). An Fc molecule of FcΔ16(+,K) can dimerize with a molecule comprising an Fc region comprising a ten-amino acid hinge deletion and a negatively charged pair mutation such as FcΔ16(−) (e.g., a GDF15 molecule comprising an Fc region of FcΔ16(+)). An Fc molecule of FcΔ10(+,K,L234A/L235A) can dimerize with a molecule comprising an Fc region comprising a ten-amino acid hinge deletion and a negatively charged pair mutation such as FcΔ10(−,L234A/L235A) (e.g., a GDF15 molecule comprising an Fc region of FcΔ10(−, L234A/L235A)).

Examples of GDF15 molecules that are GDF15-Fc fusion proteins are shown in Table 5.

TABLE 5

GDF15 Molecules

| GDF15-Fc Fusion Protein | | | GDF15-Fc Fusion Protein Components SEQ ID NOs | | |
|---|---|---|---|---|---|
| SEQ ID NO. | Desig-nation | Sequence | Fe Region | Linker | GDF15 Region |
| 38 | ScFc-GDF15 | GGGERKSSVECPPCPAPPVA<br>GPSVFLFPPKPKDTLMISRT<br>PEVTCVVVDVSHEDPEVQF<br>NWYVDGVEVHNAKTKPRE<br>EQFNSTFRVVSVLTVVHQD<br>WLNGKEYKCKVSNKGLPA<br>PIEKTISKTKGQPREPQVYT<br>LPPSREEMTKNQVSLTCLV<br>KGFYPSDIAVEWESNGQPE<br>NNYKTTPPMLDSDGSFFLY<br>SKLTVDKSRWQQGNVFSCS<br>VMHEALHNHYTQKSLSLSP<br>GGGGGSGGGGSGGGGSGG<br>GGSGGGGSGGGGSGGGGS<br>GGGGSERKSSVECPPCPAPP<br>VAGPSVFLFPPKPKDTLMIS<br>RTPEVTCVVVDVSHEDPEV<br>QFNWYVDGVEVHNAKTKP<br>REEQFNSTFRVVSVLTVVH<br>QDWLNGKEYKCKVSNKGL<br>PAPIEKTISKTKGQPREPQV<br>YTLPPSREEMTKNQVSLTC<br>LVKGFYPSDIAVEWESNGQ<br>PENNYKTTPPMLDSDGSFFL<br>YSKLTVDKSRWQQGNVFS<br>CSVMHEALHNHYTQKSLSL<br>SPGSGGGGSGGGGSGGGGS<br>GGGGSARNGDHCPLGPGRC<br>CRLHTVRASLEDLGWADW<br>VLSPREVQVTMCIGACPSQF<br>RAANMHAQIKTSLHRLKPD<br>TVPAPCCVPASYNPMVLIQ<br>KTDTGVSLQTYDDLLAKDC<br>HCI | — | — | — |
| 39 | FcΔ10(−)-(G4S)4-GDF15 | APELLGGPSVFLFPPKPKDT<br>LMISRTPEVTCVVVDVSHE<br>DPEVKFNWYVDGVEVHNA<br>KTKPREEQYNSTYRVVSVL<br>TVLHQDWLNGKEYKCKVS<br>NKALPAPIEKTISKAKGQPR<br>EPQVYTLPPSREEMTKNQV<br>SLTCLVKGFYPSDIAVEWES<br>NGQPENNY**D**TTPPVLDSDG<br>SFFLYS**D**LTVDKSRWQQGN<br>VFSCSVMHEALHNHYTQKS<br>LSLSPGGGGGSGGGGSGGG<br>GSGGGGSARNGDHCPLGPG<br>RCCRLHTVRASLEDLGWA<br>DWVLSPREVQVTMCIGACP<br>SQFRAANMHAQIKTSLHRL<br>KPDTVPAPCCVPASYNPMV<br>LIQKTDTGVSLQTYDDLLA<br>KDCHCI<br>Underlined and bolded residues are K392D and K409D mutations. | 26 | 21 | 6 |
| 40 | FcΔ10(+)-(G4)-GDF15 | APELLGGPSVFLFPPKPKDT<br>LMISRTPEVTCVVVDVSHE<br>DPEVKFNWYVDGVEVHNA<br>KTKPREEQYNSTYRVVSVL<br>TVLHQDWLNGKEYKCKVS<br>NKALPAPIEKTISKAKGQPR<br>EPQVYTLPPSR**K**EMTKNQV<br>SLTCLVKGFYPSDIAVEWES<br>NGQPENNYKTTPPVL**K**SDG<br>SFFLYSKLTVDKSRWQQGN<br>VFSCSVMHEALHNHYTQKS<br>LSLSPGGGGGARNGDHCPL | 27 | 23 | 6 |

TABLE 5-continued

| GDF15 Molecules | | | | | |
|---|---|---|---|---|---|
| GDF15-Fc Fusion Protein | | | GDF15-Fc Fusion Protein Components SEQ ID NOs | | |
| SEQ ID NO. | Designation | Sequence | Fe Region | Linker | GDF15 Region |
| | | GPGRCCRLHTVRASLEDLG WADWVLSPREVQVTMCIG ACPSQFRAANMHAQIKTSL HRLKPDTVPAPCCVPASYN PMVLIQKTDTGVSLQTYDD LLAKDCHCI Underlined and and bolded residues are E356K and D399K mutations. | | | |
| 41 | FcΔ10(-)-GDF15(Δ3) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNY**D**TTPPVLDSDG SFFLYS**D**LTVDKSRWQQGN VFSCSVMHEALHNHYTQKS LSLSPGGDHCPLGPGRCCRL HTVRASLEDLGWADWVLS PREVQVTMCIGACPSQFRA ANMHAQIKTSLHRLKPDTV PAPCCVPASYNPMVLIQKT DTGVSLQTYDDLLAKDCHC I Underlined and bolded residues are K392D and K409D mutations. | 26 | — | 13 |
| 42 | FcΔ10(-)-GDF15(N3 D) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNY**D**TTPPVLDSDG SFFLYS**D**LTVDKSRWQQGN VFSCSVMHEALHNHYTQKS LSLSPGARDGDHCPLGPGR CCRLHTVRASLEDLGWAD WVLSPREVQVTMCIGACPS QFRAANMHAQIKTSLHRLK PDTVPAPCCVPASYNPMVLI QKTDTGVSLQTYDDLLAKD CHCI Underlined and bolded residues are K392D and K409D mutations. | 26 | — | 15 |
| 43 | FcΔ10 (-, CC)-GDF15(Δ3) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVCTLPPSREEMTKNQV SLTCLVKGFYPSDIAVEWES NGQPENNY**D**TTPPVLDSDG SFFLYS**D**LTVDKSRWQQGN VFSCSVMHEALHNHYTQKS LSLSPGGDHCPLGPGRCCRL HTVRASLEDLGWADWVLS | 28 | — | 13 |

TABLE 5-continued

| GDF15 Molecules | | | | | |
|---|---|---|---|---|---|
| GDF15-Fc Fusion Protein | | | GDF15-Fc Fusion Protein Components SEQ ID NOs | | |
| SEQ ID NO. | Desig-nation | Sequence | Fc Region | Linker | GDF15 Region |
| | | PREVQVTMCIGACPSQFRA ANMHAQIKTSLHRLKPDTV PAPCCVPASYNPMVLIQKT DTGVSLQTYDDLLAKDCHC I Underlined and italicized residue is Y349C mutation; underlined and bolded residues are K392D and K409D mutations. | | | |
| 44 | FcΔ10 (−, CC)-GDF15(N3D) | APELLGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVCTLPPSREEMTKNQV SLTCLVKGFYPSDIAVEWES NGQPENNY**D**TTPPVLDSDG SFFLYS**D**LTVDKSRWQQGN VFSCSVMHEALHNHYTQKS LSLSPGARDGDHCPLGPGR CCRLHTVRASLEDLGWAD WVLSPREVQVTMCIGACPS QFRAANMHAQIKTSLHRLK PDTVPAPCCVPASYNPMVLI QKTDTGVSLQTYDDLLAKD CHCI Underlined and italicized residue is Y349C mutation; underlined and bolded residues are K392D and K409D mutations. | 28 | — | 15 |
| 45 | FcΔ16 (−, CC)-GDF15(Δ3/D5E) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVCT LPPSREEMTKNQVSLTCLV KGFYPSDIAVEWESNGQPE NNY**D**TTPPVLDSDGSFFLYS **D**LTVDKSRWQQGNVFSCS VMHEALHNHYTQKSLSLSP GGEHCPLGPGRCCRLHTVR ASLEDLGWADWVLSPREV QVTMCIGACPSQFRAANMH AQIKTSLHRLKPDTVPAPCC VPASYNPMVLIQKTDTGVS LQTYDDLLAKDCHCI Underlined and italicized residue is Y349C mutation; underlined and bolded residues are K392D and K409D mutations. | 29 | — | 17 |
| 46 | FcΔ16 (−, CC)-GDF15(N3Q/D5E) | GPSVFLFPPKPKDTLMISRT PEVTCVVVDVSHEDPEVKF NWYVDGVEVHNAKTKPRE EQYNSTYRVVSVLTVLHQD WLNGKEYKCKVSNKALPA PIEKTISKAKGQPREPQVCT LPPSREEMTKNQVSLTCLV KGFYPSDIAVEWESNGQPE NNY**D**TTPPVLDSDGSFFLYS **D**LTVDKSRWQQGNVFSCS | 29 | — | 18 |

TABLE 5-continued

| GDF15 Molecules | | | | | |
|---|---|---|---|---|---|
| GDF15-Fc Fusion Protein | | | GDF15-Fc Fusion Protein Components SEQ ID NOs | | |
| SEQ ID NO. | Desig-nation | Sequence | Fe Region | Linker | GDF15 Region |
| | | VMHEALHNHYTQKSLSLSP<br>GARQGEHCPLGPGRCCRLH<br>TVRASLEDLGWADWVLSP<br>REVQVTMCIGACPSQFRAA<br>NMHAQIKTSLHRLKPDTVP<br>APCCVPASYNPMVLIQKTD<br>TGVSLQTYDDLLAKDCHCI<br>Underlined and italicized residue is Y349C mutation; underlined and bolded residues are K392D and K409D mutations. | | | |
| 47 | FcΔ16(−)-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GARQGEHCPLGPGRCCRLH<br>TVRASLEDLGWADWVLSP<br>REVQVTMCIGACPSQFRAA<br>NMHAQIKTSLHRLKPDTVP<br>APCCVPASYNPMVLIQKTD<br>TGVSLQTYDDLLAKDCHCI<br>Underlined and bolded residues are K392D and K409D mutations. | 30 | — | 18 |
| 48 | FcΔ16(−)-(G4Q)4-GDF15 | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGQGGGGQGGGGQG<br>GGGQARNGDHCPLGPGRC<br>CRLHTVRASLEDLGWADW<br>VLSPREVQVTMCIGACPSQF<br>RAANMHAQIKTSLHRLKPD<br>TVPAPCCVPASYNPMVLIQ<br>KTDTGVSLQTYDDLLAKDC<br>HCI<br>Underlined and bolded residues are K392D and K409D mutations. | 30 | 25 | 6 |
| 49 | FcΔ16(−)-(G4Q)4-GDF15(N3Q) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGQGGGGQGGGGQG<br>GGGQARQGDHCPLGPGRC<br>CRLHTVRASLEDLGWADW | 30 | 25 | 14 |

TABLE 5-continued

GDF15 Molecules

| GDF15-Fc Fusion Protein | | | GDF15-Fc Fusion Protein Components SEQ ID NOs | | |
|---|---|---|---|---|---|
| SEQ ID NO. | Desig-nation | Sequence | Fc Region | Linker | GDF15 Region |
| | | VLSPREVQVTMCIGACPSQF<br>RAANMHAQIKTSLHRLKPD<br>TVPAPCCVPASYNPMVLIQ<br>KTDTGVSLQTYDDLLAKDC<br>HCI<br>Underlined and bolded residues are K392D and K409D mutations. | | | |
| 50 | FcΔ16(−)-(G4Q)4-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGQGGGGQGGGGQG<br>GGGQARQGEHCPLGPGRCC<br>RLHTVRASLEDLGWADWV<br>LSPREVQVTMCIGACPSQFR<br>AANMHAQIKTSLHRLKPDT<br>VPAPCCVPASYNPMVLIQK<br>TDTGVSLQTYDDLLAKDCH<br>CI<br>Underlined and bolded residues are K392D and K409D mutations. | 30 | 25 | 18 |
| 51 | FcΔ16(−)-(G4S)2-GDF15(N3Q) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGSGGGGSARQGDHC<br>PLGPGRCCRLHTVRASLED<br>LGWADWVLSPREVQVTMC<br>IGACPSQFRAANMHAQIKT<br>SLHRLKPDTVPAPCCVPAS<br>YNPMVLIQKTDTGVSLQTY<br>DDLLAKDCHCI<br>Underlined and bolded residues are K392D and K409D mutations. | 30 | 20 | 14 |
| 52 | FcΔ16(−)-(G4S)2-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGSGGGGSARQGEHC<br>PLGPGRCCRLHTVRASLED<br>LGWADWVLSPREVQVTMC<br>IGACPSQFRAANMHAQIKT<br>SLHRLKPDTVPAPCCVPAS<br>YNPMVLIQKTDTGVSLQTY | 30 | 20 | 18 |

TABLE 5-continued

| GDF15 Molecules | | | | | |
|---|---|---|---|---|---|
| GDF15-Fc Fusion Protein | | | GDF15-Fc Fusion Protein Components SEQ ID NOs | | |
| SEQ ID NO. | Designation | Sequence | Fe Region | Linker | GDF15 Region |
| | | DDLLAKDCHCI<br>Underlined and bolded residues are K392D and K409D mutations. | | | |
| 53 | FcΔ16(-)-G4S-GDF15(N3Q) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGSARQGDHCPLGPG<br>RCCRLHTVRASLEDLGWA<br>DWVLSPREVQVTMCIGACP<br>SQFRAANMHAQIKTSLHRL<br>KPDTVPAPCCVPASYNPMV<br>LIQKTDTGVSLQTYDDLLA<br>KDCHCI<br>Underlined and bolded residues are K392D and K409D mutations. | 30 | 19 | 14 |
| 54 | FcΔ16(-)-G4S-GDF15(N3Q/D5E) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GGGGGSARQGEHCPLGPGR<br>CCRLHTVRASLEDLGWAD<br>WVLSPREVQVTMCIGACPS<br>QFRAANMHAQIKTSLHRLK<br>PDTVPAPCCVPASYNPMVLI<br>QKTDTGVSLQTYDDLLAKD<br>CHCI<br>Underlined and bolded residues are K392D and K409D mutations. | 30 | 19 | 18 |
| 55 | FcΔ16(-)-GDF15(N3Q) | GPSVFLFPPKPKDTLMISRT<br>PEVTCVVVDVSHEDPEVKF<br>NWYVDGVEVHNAKTKPRE<br>EQYNSTYRVVSVLTVLHQD<br>WLNGKEYKCKVSNKALPA<br>PIEKTISKAKGQPREPQVYT<br>LPPSREEMTKNQVSLTCLV<br>KGFYPSDIAVEWESNGQPE<br>NNY**D**TTPPVLDSDGSFFLYS<br>**D**LTVDKSRWQQGNVFSCS<br>VMHEALHNHYTQKSLSLSP<br>GARQGDHCPLGPGRCCRLH<br>TVRASLEDLGWADWVLSP<br>REVQVTMCIGACPSQFRAA<br>NMHAQIKTSLHRLKPDTVP<br>APCCVPASYNPMVLIQKTD<br>TGVSLQTYDDLLAKDCHCI<br>Underlined and bolded residues are K392D and K409D mutations. | 30 | — | 14 |

TABLE 5-continued

| GDF15 Molecules | | | | | |
|---|---|---|---|---|---|
| GDF15-Fc Fusion Protein | | | GDF15-Fc Fusion Protein Components SEQ ID NOs | | |
| SEQ ID NO. | Desig-nation | Sequence | Fc Region | Linker | GDF15 Region |
| 56 | FcΔ10(-, L234A/L235A)-(G4Q)4-GDF15(N3Q) | APEAAGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNYDTTPPVLDSDG SFFLYSDLTVDKSRWQQGN VFSCSVMHEALHNHYTQKS LSLSPGGGGGQGGGGQGG GGQGGGGQARQGDHCPLG PGRCCRLHTVRASLEDLGW ADWVLSPREVQVTMCIGAC PSQFRAANMHAQIKTSLHR LKPDTVPAPCCVPASYNPM VLIQKTDTGVSLQTYDDLL AKDCHCI Underlined and italicized residues are L234A and L235A mutations; underlined and bolded residues are K392D and K409D mutations. | 31 | 25 | 14 |
| 57 | FcΔ10(-, L234A/L235A)-(G4Q)4-GDF15(N3Q/D5E) | APEAAGGPSVFLFPPKPKDT LMISRTPEVTCVVVDVSHE DPEVKFNWYVDGVEVHNA KTKPREEQYNSTYRVVSVL TVLHQDWLNGKEYKCKVS NKALPAPIEKTISKAKGQPR EPQVYTLPPSREEMTKNQV SLTCLVKGFYPSDIAVEWES NGQPENNYDTTPPVLDSDG SFFLYSDLTVDKSRWQQGN VFSCSVMHEALHNHYTQKS LSLSPGGGGGQGGGGQGG GGQGGGGQARQGEHCPLG PGRCCRLHTVRASLEDLGW ADWVLSPREVQVTMCIGAC PSQFRAANMHAQIKTSLHR LKPDTVPAPCCVPASYNPM VLIQKTDTGVSLQTYDDLL AKDCHCI Underlined and italicized residues are L234A and L235A mutations; underlined and bolded residues are K392D and K409D mutations. | 31 | 25 | 18 |

In some embodiments, the fusion protein is an scFc-GDF15 in which the GDF15 region is joined to two Fc regions. In some embodiments, the fusion protein comprises an amino acid sequence that has at least 85%, 90%, 95% or 99% sequence identity to SEQ ID NO: 38. In some embodiments, the fusion protein comprises an amino acid sequence of SEQ ID NO: 38.

In calculating percent sequence identity, the sequences being compared are aligned in a way that gives the largest match between the sequences. A computer program that can be used to determine percent identity is the GCG program package, which includes GAP (Devereux et al., (1984) Nucl. Acid Res. 12:387; Genetics Computer Group, University of Wisconsin, Madison, Wis.). The computer algorithm GAP can be used to align the two polypeptides or polynucleotides for which the percent sequence identity is to be determined. The sequences are aligned for optimal matching of their respective amino acid or nucleotide (the "matched span", as determined by the algorithm). A gap opening penalty (which is calculated as 3× the average diagonal, wherein the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. In certain embodiments, a standard comparison matrix (see, Dayhoff et al., (1978) Atlas of Protein Sequence and Structure 5:345-352 for the PAM 250 comparison matrix; Henikoff et al., (1992)

Proc. Natl. Acad. Sci. U.S.A. 9:10915-10919 for the BLOSUM 62 comparison matrix) is also used by the algorithm. Parameters that can be used for determining percent identity using the GAP program are the following:

Algorithm: Needleman et al., 1970, J. Mol. Biol. 48:443-453;

Comparison matrix: BLOSUM 62 from Henikoff et al., 1992, supra;

Gap Penalty: 12 (but with no penalty for end gaps)

Gap Length Penalty: 4

Threshold of Similarity: 0

Certain alignment schemes for aligning two amino acid sequences can result in matching of only a short region of the two sequences, and this small aligned region can have very high sequence identity even though there is no significant relationship between the two full-length sequences. Accordingly, the selected alignment method (e.g., the GAP program) can be adjusted if so desired to result in an alignment that spans at least 50 contiguous amino acids of the target polypeptide.

In some embodiments, the GDF15 molecule is FcΔ10(−)-(G4S)4-GDF15, FcΔ10(+)-(G4)-GDF15, FcΔ10(−)-GDF15 (Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16(−)-GDF15 (N3Q/D5E), FcΔ16(−)-(G4Q)4-GDF15, FcΔ16(−)-(G4Q)4-GDF15(N3Q), FcΔ16(−)-(G4Q)4-GDF15(N3Q/D5E), FcΔ16(−)-(G4S)2-GDF15(N3Q), FcΔ16(−)-(G4S)2-GDF15 (N3Q/D5E), FcΔ16(−)-G4S-GDF15(N3Q), FcΔ16(−)-G4S-GDF15(N3Q/D5E), FcΔ16(−)-GDF15(N3Q), FcΔ10(−, L234A/L235A)-(G4Q)4-GDF15(N3Q), or FcΔ10(−,L234A/L235A)-(G4Q)4-GDF15(N3Q/D5E).

In some embodiments, the GDF15 molecule comprises the amino acid sequence of SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 85% sequence identity to SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 90% sequence identity to SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 95% sequence identity to SEQ ID NO: 39, 40, 41, 42, 43, 44, 45, 46, 47, 48, 49, 50, 51, 52, 53, 54, 55, 56, or 57. In some embodiments, the GDF15 molecules comprises an amino acid sequence that has at least 99% sequence identity to SEQ ID NO: 39, 40, 41, 42, 43, 44, 45, 46, 47, 48, 49, 50, 51, 52, 53, 54, 55, 56, or 57.

In some embodiments, the GDF15 molecule is a FcΔ10 (−)-(G4S)4-GDF15, FcΔ10(+)-(G4)-GDF15, FcΔ10(−)-GDF15(Δ3), FcΔ10(−)-GDF15(N3D), FcΔ10(−,CC)-GDF15(Δ3), FcΔ10(−,CC)-GDF15(N3D), FcΔ16(−,CC)-GDF15(Δ3/D5E), FcΔ16(−,CC)-GDF15(N3Q/D5E), FcΔ16 (−)-GDF15(N3Q/D5E), FcΔ16(−)-(G4Q)4-GDF15, FcΔ16 (−)-(G4Q)4-GDF15(N3Q), FcΔ16(−)-(G4Q)4-GDF15 (N3Q/D5E), FcΔ16(−)-(G4S)2-GDF15(N3Q), FcΔ16(−)-(G4S)2-GDF15(N3Q/D5E), FcΔ16(−)-G4S-GDF15(N3Q), FcΔ16(−)-G4S-GDF15(N3Q/D5E), FcΔ16(−)-GDF15 (N3Q), FcΔ10(−,L234A/L235A)-(G4Q)4-GDF15(N3Q), or FcΔ10(−,L234A/L235A)-(G4Q)4-GDF15(N3Q/D5E) molecule that has at least 85%, 90%, 95% or 99% sequence identity to its Fc region and/or GDF15 region. For example, a FcΔ10(−)-(G4S)4-GDF15 molecule with at least 85%, 90%, 95% or 99% sequence identity to its Fc region and/or GDF15 region, includes a GDF15 molecule with an Fc region that has a ten-amino acid deletion of the hinge region and a negatively charged pair mutation, and has at least 85%, 90%, 95% or 99% sequence identity to SEQ ID NO: 26 and/or a GDF15 region that has at least 85%, 90%, 95% or 99% sequence identity to SEQ ID NO: 6. In another example, a FcΔ16(−)-(G4Q)4-GDF15(N3Q/D5E) molecule with at least 85%, 90%, 95% or 99% sequence identity to its Fc region and/or a GDF15 region, includes a GDF15 molecule with an Fc region that has a sixteen-amino acid deletion of the hinge region and a negatively charged pair mutation that has at least 85%, 90%, 95% or 99% sequence identity to SEQ ID NO: 30 and/or a GDF15 region that has at least 85%, 90%, 95% or 99% sequence identity to SEQ ID NO: 18. In yet another example, a FcΔ10(−,L234A/L235A)-(G4Q)4-GDF15(N3Q/D5E) molecule with at least 85%, 90%, 95% or 99% sequence identity to its Fc region and/or a GDF15 region, includes a GDF15 molecule with an Fc region that has a ten-amino acid deletion of the hinge region, a negatively charged pair mutation and leucine to alanine mutations at positions 234 and 235 and has at least 85%, 90%, 95% or 99% sequence identity to SEQ ID NO: 31 and/or a GDF15 region that has at least 85%, 90%, 95% or 99% sequence identity to SEQ ID NO: 18.

Also provided herein are dimers and tetramers comprising a GDF15 molecule provided herein. In one embodiment, the dimer comprises a GDF15-Fc fusion comprising the amino acid sequence of any one of SEQ ID NOs: 39-57. In some embodiments, a GDF15-Fc fusion comprising the amino acid sequence of SEQ ID NO: 39, 40, 41, 42, 43, 44, 45, 46, 47, 48, 49, 50, 51, 52, 53, 54, 55, 56 or 57 dimerizes with an Fc molecule comprising the amino acid sequence of SEQ ID NO: 32, 33, 34, 35, 36, or 37 (in which the C-terminal lysine is optional), such as shown in Table 6. For example, in some embodiments, the dimer is FcΔ10(−)-(G4S)4-GDF15: FcΔ10(+,K). In another embodiment, the dimer is FcΔ10(−,L234A/L235A)-(G4Q)4-GDF15(N3Q): FcΔ10(+, K,L234A/L235A). In yet another embodiment, the dimer is FcΔ10(−,L234A/L235A)-(G4Q)4-GDF15(N3Q):FcΔ10(+, K,L234A/L235A).

TABLE 6

| Dimers | | | |
|---|---|---|---|
| GDF15-Fc Fusion SEQ ID NO. | GDF15-Fc Fusion Designation | Fc Molecule SEQ ID NO. | Corresponding Fc Molecule Designation |
| 39 | FcΔ10(−)-(G4S)4-GDF15 | 32 | FcΔ10(+, K) |
| 40 | FcΔ10(+)-(G4)-GDF15 | 33 | FcΔ10(−, K) |
| 41 | FcΔ10(−)-GDF15(Δ3) | 32 | FcΔ10(+, K) |
| 42 | FcΔ10(−)-GDF15(N3D) | 32 | FcΔ10(+, K) |
| 43 | FcΔ10(−, CC)-GDF15(Δ3) | 34 | FcΔ10(+, K, CC) |

TABLE 6-continued

| Dimers | | | |
|---|---|---|---|
| GDF15-Fc Fusion SEQ ID NO. | GDF15-Fc Fusion Designation | Fc Molecule SEQ ID NO. | Corresponding Fc Molecule Designation |
| 44 | FcΔ10(–, CC)-GDF15(N3D) | 34 | FcΔ10(+, K, CC) |
| 45 | FcΔ16(–, CC)-GDF15(A3/D5E) | 35 | FcΔ16(+, K, CC) |
| 46 | FcΔ16(–, CC)-GDF15(N3Q/D5E) | 35 | FcΔ16(+, K, CC) |
| 47 | FcΔ16(–)-GDF15(N3Q/D5E) | 36 | FcΔ16(+, K) |
| 48 | FcΔ16(–)-(G4Q)4-GDF15 | 36 | FcΔ16(+, K) |
| 49 | FcΔ16(–)-(G4Q)4-GDF15(N3Q) | 36 | FcΔ16(+, K) |
| 50 | FcΔ16(–)-(G4Q)4-GDF15(N3Q/D5E) | 36 | FcΔ16(+, K) |
| 51 | FcΔ16(–)-(G4S)2-GDF15(N3Q) | 36 | FcΔ16(+, K) |
| 52 | FcΔ16(–)-(G4S)2- GDF15(N3Q/D5E) | 36 | FcΔ16(+, K) |
| 53 | FcΔ16(–)-G4S- GDF15(N3Q) | 36 | FcΔ16(+, K) |
| 54 | FcΔ16(–)-G4S-GDF15(N3Q/D5E) | 36 | FcΔ16(+, K) |
| 55 | FcΔ16(–)-GDF15(N3Q) | 36 | FcΔ16(+, K) |
| 56 | FcΔ10(–, L234A/L235A)-(G4Q)4-GDF15(N3Q) | 37 | FcA10(+, K, L234A/L235A) |
| 57 | FcΔ10(–, L234A/L235A)-(G4Q)4-GDF15(N3Q/D5E) | 37 | FcA10(+, K, L234A/L235A) |

In one embodiment, a GDF15-Fc fusion comprising the amino acid sequence of SEQ ID NO: 39 dimerizes with an Fc molecule comprising SEQ ID NO: 32 (C-terminal lysine optional). In another embodiment, a GDF15-Fc fusion comprising the amino acid sequence of SEQ ID NO: 40 dimerizes with an Fc molecule comprising SEQ ID NO: 33 (C-terminal lysine optional). In another embodiment, a GDF15-Fc fusion comprising the amino acid sequence of SEQ ID NO: 41 dimerizes with an Fc molecule comprising SEQ ID NO: 32 (C-terminal lysine optional). In another embodiment, a GDF15-Fc fusion comprising the amino acid sequence of SEQ ID NO: 42 dimerizes with an Fc molecule comprising SEQ ID NO: 32 (C-terminal lysine optional). In another embodiment, a GDF15-Fc fusion comprising the amino acid sequence of SEQ ID NO: 43 dimerizes with an Fc molecule comprising SEQ ID NO: 34 (C-terminal lysine optional). In another embodiment, a GDF15-Fc fusion comprising the amino acid sequence of SEQ ID NO: 44 dimerizes with an Fc molecule comprising SEQ ID NO: 34 (C-terminal lysine optional). In another embodiment, a GDF15-Fc fusion comprising the amino acid sequence of SEQ ID NO: 44 dimerizes with an Fc molecule comprising SEQ ID NO: 34 (C-terminal lysine optional). In another embodiment, a GDF15-Fc fusion comprising the amino acid sequence of SEQ ID NO: 45 dimerizes with an Fc molecule comprising SEQ ID NO: 35 (C-terminal lysine optional). In another embodiment, a GDF15-Fc fusion comprising the amino acid sequence of SEQ ID NO: 46 dimerizes with an Fc molecule comprising SEQ ID NO: 35 (C-terminal lysine optional). In another embodiment, a GDF15-Fc fusion comprising the amino acid sequence of SEQ ID NO: 47 dimerizes with an Fc molecule comprising SEQ ID NO: 36 (C-terminal lysine optional). In another embodiment, a GDF15-Fc fusion comprising the amino acid sequence of SEQ ID NO: 48 dimerizes with an Fc molecule comprising SEQ ID NO: 36 (C-terminal lysine optional). In another embodiment, a GDF15-Fc fusion comprising the amino acid sequence of SEQ ID NO: 49 dimerizes with an Fc molecule comprising SEQ ID NO: 36 (C-terminal lysine optional). In another embodiment, a GDF15-Fc fusion comprising the amino acid sequence of SEQ ID NO: 50 dimerizes with an Fc molecule comprising SEQ ID NO: 36 (C-terminal lysine optional). In another embodiment, a GDF15-Fc fusion comprising the amino acid sequence of SEQ ID NO: 51 dimerizes with an Fc molecule comprising SEQ ID NO: 36 (C-terminal lysine optional). In another embodiment, a GDF15-Fc fusion comprising the amino acid sequence of SEQ ID NO: 52 dimerizes with an Fc molecule comprising SEQ ID NO: 36 (C-terminal lysine optional). In another embodiment, a GDF15-Fc fusion comprising the amino acid sequence of SEQ ID NO: 53 dimerizes with an Fc molecule comprising SEQ ID NO: 36 (C-terminal lysine optional). In another embodiment, a GDF15-Fc fusion comprising the amino acid sequence of SEQ ID NO: 54 dimerizes with an Fc molecule comprising SEQ ID NO: 36 (C-terminal lysine optional). In another embodiment, a GDF15-Fc fusion comprising the amino acid sequence of SEQ ID NO: 55 dimerizes with an Fc molecule comprising SEQ ID NO: 36 (C-terminal lysine optional). In another embodiment, a GDF15-Fc fusion comprising the amino acid sequence of SEQ ID NO: 56 dimerizes with an Fc molecule comprising SEQ ID NO: 37 (C-terminal lysine optional). In another embodiment, a GDF15-Fc fusion comprising the amino acid sequence of SEQ ID NO: 57 dimerizes with an Fc molecule comprising SEQ ID NO: 37 (C-terminal lysine optional).

In some embodiments, the dimers form tetramers. For example, the dimers in Table 6 can form tetramers. In some embodiments, the tetramers are formed form the same dimers. In some embodiments, two dimers of FcΔ10(−)-(G4S)4-GDF15:FcΔ10(+,K); FcΔ10(+)-(G4)-GDF15:FcΔ10(−,K); FcΔ10(−)-GDF15(Δ3):FcΔ10(+,K); FcΔ10(−)-GDF15(N3D):FcΔ10(+,K); FcΔ10(−,CC)-GDF15(Δ3):FcΔ10(+,K,CC); FcΔ10(−,CC)-GDF15(N3D):FcΔ10(+,K,CC); FcΔ16(−,CC)-GDF15(Δ3/D5E):FcΔ16(+,K,CC); FcΔ16(−,CC)-GDF15(N3Q/D5E):FcΔ16(+,K,CC); FcΔ16(−)-GDF15(N3Q/D5E):FcΔ16(+,K); FcΔ16(−)-(G4Q)4-GDF15:FcΔ16(+,K); FcΔ16(−)-(G4Q)4-GDF15(N3Q):FcΔ16(+,K); FcΔ16(−)-(G4Q)4-GDF15(N3Q/D5E):FcΔ16(+,K); FcΔ16(−)-(G4S)2-GDF15(N3Q):FcΔ16(+,K); FcΔ16(−)-(G4S)2-GDF15(N3Q/D5E):FcΔ16(+,K); FcΔ16(−)-G4S-GDF15(N3Q):FcΔ16(+,K); FcΔ16(−)-G4S-GDF15(N3Q/D5E): FcΔ16(+,K); FcΔ16(−)-GDF15(N3Q): FcΔ16(+,K); FcΔ10(−,L234A/L235A)-(G4Q)4-GDF15(N3Q): FcΔ10(+,K,L234A/L235A); or FcΔ10(−,L234A/L235A)-(G4Q)4-GDF15(N3Q/D5E):FcΔ10(+,K,L234A/L235A) form a tetramer, such as through the dimerization of the two GDF15 regions.

In some embodiments, the GDF15 molecule is a GDF15 protein fused to human serum albumin (HSA) or a functional variant thereof, optionally through a linker. In some embodiments, the GDF15 molecule is a GDF15 molecule or compound, such as a mutein and/or fusion protein, or complex or dimer comprising a GDF15 molecule or compound, such as disclosed in PCT publication WO 2014/120619A2, WO 2013/148117 A1, WO 2016/018931 A1, WO 2016/069921 A1, WO 2015/197446 A1, WO 2017/202936 A1, WO 2018/215525 A1, WO 2017/196647 A1, WO 2020/104948 A1, WO 2019/195091 A1, WO 2015/198199 A1, WO 2017/109706 A1, WO 2015/200078 A1, which are incorporated by reference in its entirety.

Also provided herein are host cells comprising the nucleic acids and vectors for producing the GDF15 and Fc molecules disclosed herein. In various embodiments, the vector or nucleic acid is integrated into the host cell genome, which in other embodiments the vector or nucleic acid is extrachromosomal.

Recombinant cells, such as yeast, bacterial (e.g., *E. coli*), and mammalian cells (e.g., immortalized mammalian cells) comprising such a nucleic acid, vector, or combinations of either or both thereof are provided. In various embodiments, cells comprising a non-integrated nucleic acid, such as a plasmid, cosmid, phagemid, or linear expression element, which comprises a sequence coding for expression of a GDF15 molecule and/or an Fc molecule. In some embodiments, the cell comprises a nucleic acid for producing a GDF15 molecule and another cell comprises a nucleic acid for producing an Fc molecule for dimerization with the GDF15 molecule (e.g., a vector for encoding a GDF15 molecule in one cell and a second vector for encoding an Fc molecule in a second cell). In other embodiments, a host cell comprises a nucleic acid for producing a GDF15 molecule and an Fc molecule (e.g., a vector that encodes both molecules). In another embodiment, a host cell comprises a nucleic acid for producing a GDF15 molecule and another nucleic acid for producing an Fc molecule (e.g., two separate vectors, one that encodes a GDF15 molecule and one that encodes an Fc molecule, in a single host cell)

A vector comprising a nucleic acid sequence encoding a GDF15 molecule and/or an Fc molecule can be introduced into a host cell by transformation or by transfection, such as by methods known in the art.

A nucleic acid encoding a GDF15 molecule can be positioned in and/or delivered to a host cell or host animal via a viral vector. A viral vector can comprise any number of viral polynucleotides, alone or in combination with one or more viral proteins, which facilitate delivery, replication, and/or expression of the nucleic acid of the invention in a desired host cell. The viral vector can be a polynucleotide comprising all or part of a viral genome, a viral protein/nucleic acid conjugate, a virus-like particle (VLP), or an intact virus particle comprising viral nucleic acids and a nucleic acid encoding a polypeptide comprising a GDF15 region. A viral particle viral vector can comprise a wild-type viral particle or a modified viral particle. The viral vector can be a vector which requires the presence of another vector or wild-type virus for replication and/or expression (e.g., a viral vector can be a helper-dependent virus), such as an adenoviral vector amplicon. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, flaviviral vectors, alphaviral vectors, herpes viral vectors, pox virus vectors, retroviral vectors, including lentiviral vectors.

A GDF15 molecule can be isolated using standard protein purification methods. A polypeptide comprising a GDF15 region can be isolated from a cell that has been engineered to express a polypeptide comprising a GDF15 region, for example a cell that does not naturally express native GDF15. Protein purification methods known in the art can be employed to isolate GDF15 molecules, as well as associated materials and reagents. Methods of purifying a GDF15 molecule are also provided in the Examples herein. Additional purification methods that may be useful for isolating GDF15 molecules can be found in references such as Bootcov M R, 1997, *Proc. Natl. Acad. Sci. USA* 94:11514-9, Fairlie W D, 2000, *Gene* 254: 67-76.

Pharmaceutical compositions comprising a GDF15 molecule (and optionally, an Fc molecule, such as a dimer or tetramer disclosed herein) are also provided. Such polypeptide pharmaceutical compositions can comprise a therapeutically effective amount of a GDF15 molecule in admixture with a pharmaceutically or physiologically acceptable formulation agent or carrier selected for suitability with the mode of administration. The pharmaceutically or physiologically acceptable formulation agent can be one or more formulation agents suitable for accomplishing or enhancing the delivery of a GDF15 molecule into the body of a human or non-human subject. Pharmaceutically acceptable substances such as wetting or emulsifying agents, preservatives or buffers, which enhance the shelf life or effectiveness of the GDF15 molecule can also act as, or form a component of, a formulation carrier. Acceptable pharmaceutically acceptable carriers are preferably nontoxic to recipients at the dosages and concentrations employed. The pharmaceutical composition can contain formulation agent(s) for modifying, maintaining, or preserving, for example, the pH, osmolarity, viscosity, clarity, color, isotonicity, odor, sterility, stability, rate of dissolution or release, adsorption, or penetration of the composition.

The effective amount of pharmaceutical composition comprising a GDF15 molecule which is to be employed therapeutically will depend, for example, upon the therapeutic context and objectives. One skilled in the art will appreciate that the appropriate dosage levels for treatment will thus vary depending, in part, upon the molecule delivered, the indication for which a GDF15 molecule is being used, the route of administration, and the size (body weight, body surface, or organ size) and condition (the age and general health) of the subject. The frequency of dosing will depend upon the pharmacokinetic parameters of the GDF15 molecule in the formulation being used.

The route of administration of the pharmaceutical composition can be orally; through injection by intravenous, intraperitoneal, intracerebral (intraparenchymal), intracerebroventricular, intramuscular, intraocular, intraarterial, intraportal, or intralesional routes; by sustained release systems (which may also be injected); or by implantation devices. Where desired, the compositions can be administered by bolus injection or continuously by infusion, or by an implantation device. The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

A GDF15 molecule can be used to treat, diagnose or ameliorate, a heart condition, a cardiac condition or cardiovascular disease (CVD) in a subject. In some embodiments, the heart condition is heart failure. In some embodiments, the heart failure is heart failure with preserved ejection fraction (HFpEF).

Also provided is a method of treating a subject with cardiometabolic syndrome (CMS) comprising administering a GDF15 molecule. In some embodiments, a subject with CMS is obese. In some embodiments, a subject with CMS has impaired metabolism, pancreatic dysfunction, hypertension, diastolic dysfunction (DD), HFpEF, decreased exercise capacity, or renal dysfunction. For example, the subject may have an increase in body weight or heart weight, or decreased adiponectin, as compared to a non-obese subject. A subject may have an increase in glucose, triglycerides, cholesterol, or insulin levels as compared to a subject without impaired metabolism. A subject may have levels of c-peptide, proinsulin, amylin or glucagon that differs from a subject without pancreatic dysfunction. A subject with hypertension, DD, or HFpEF may have increased levels of aldosterone, FABP3, IL-16, or ST2, as compared to a subject without hypertension, DD, or HFpEF. In some embodiments, a subject with hypertension, DD, or HFpEF has a decreased heart rate, increased Tau level, increased E/E' ratio (abnormal LV filling pressure may be estimated non-invasively by E/E' >15), or increased isovolumic relaxation time (IVRT), as compared to a subject without hypertension, DD, or HFpEF. In some embodiments, the subject with hypertension, DD, or HFpEF has the same left ventricular ejection fraction (LVEF) percentage as a subject without hypertension, DD, or HFpEF. A subject with decreased exercise capacity may have a decrease in running distance, time (e.g., time to exhaustion), or peak VO2 as compared to a subject without decreased exercise capacity. In some embodiments, a subject with renal dysfunction has an increase in NGAL, KIM-1, or clusterin levels as compared to a subject without renal dysfunction.

In some subjects with CMS, after treatment with a GDF15 molecule, the subject has reduced CMS. For example, the subject may have improved metabolism, pancreatic function, hypertension, diastolic function, exercise capacity, or renal function. For example, the subject may have a decrease in body weight or heart weight, or increased adiponectin, as compared to prior to treatment with a GDF15 molecule. A subject may have a decrease in glucose, triglycerides, cholesterol, or insulin levels as compared to prior to treatment with a GDF15 molecule. A subject treated with a GDF15 molecule may have levels of c-peptide, proinsulin, amylin or glucagon that is similar to that of a subject without pancreatic dysfunction. The subject may have decreased levels of aldosterone, FABP3, IL-16, or ST2, as compared to prior to treatment with a GDF15 molecule. In some embodiments, a subject has an increase in heart rate, decrease in Tau level, decrease in E/E' ratio, or decrease in IVRT, as compared to prior to treatment with a GDF15 molecule. In some embodiments, a subject has an increase in running distance, time (e.g., time to exhaustion), or peak VO2 as compared to a prior to treatment with a GDF15 molecule. In some embodiments, the subject has a decrease in NGAL, KIM-1, or clusterin levels as compared to prior to GDF15 treatment.

In some embodiments, after treatment with the GDF15 molecule, the subject has a decreased heart weight, improved exercise capacity, or change in the level of adiponectin, sE-selectin, sICAM, Myl3, osteopontin, TIMP1, VEGF, or vWF, after treatment with the GDF15 molecule. In some embodiments, the level of adiponectin is increased. In some embodiments, the level of sE-selectin, sICAM, Myl3, osteopontin, TIMP1, VEGF, vWF, or any combination thereof is decreased. In yet other embodiments, the subject has decreased heart to brain weight ratio, left ventricle (LV) mass, cardiac output, stroke volume, or % ejection fraction echocardiographic, after treatment with the GDF15 molecule.

The administration can be performed such as by IV injection, intraperitoneal (IP) injection, subcutaneous injection, intramuscular injection, or orally in the form of a tablet or liquid formation. A therapeutically effective dose of a GDF15 molecule will depend upon the administration schedule, the unit dose of agent administered, whether the GDF15 molecule is administered in combination with other therapeutic agents, the immune status and the health of the recipient. A therapeutically effective dose is an amount of a GDF15 molecule that elicits a biological or medicinal response in a tissue system, animal, or human being sought by a researcher, medical doctor, or other clinician, which includes alleviation or amelioration of the symptoms of the disease or disorder being treated, i.e., an amount of a GDF15 molecule that supports an observable level of one or more desired biological or medicinal response, such as decrease in body weight or heart weight; increase in adiponectin; decrease in glucose, triglycerides, cholesterol, or insulin levels; changes in levels of c-peptide, proinsulin, amylin or glucagon; decrease in level of aldosterone, FABP3, IL-16, or ST2; increase in heart rate; decrease in Tau level; decrease in E/E' ratio; decrease in IVRT; increase in running distance, time (e.g., time to exhaustion), or peak VO2; decrease in NGAL, KIM-1, or clusterin level; decrease in level of sE-selectin, sICAM, Myl3, osteopontin, TIMP1, VEGF, or vWF; decrease in heart to brain weight ratio; decrease in left ventricle (LV) mass; decrease in cardiac output; decrease in stroke volume, or decrease in % ejection fraction. A therapeutically effective dose of a GDF15 molecule can also vary with the desired result.

Also provided herein is a method comprising measuring a baseline level of one or more of body weight; heart weight; adiponectin level; decrease in glucose, triglycerides, cholesterol, or insulin levels; c-peptide, proinsulin, amylin or glucagon level; aldosterone, FABP3, IL-16, or ST2 level; heart rate; Tau level; E/E' ratio; IVRT; running distance, time (e.g., time to exhaustion) or peak VO2; NGAL, KIM-1, or clusterin level; sE-selectin, sICAM, Myl3, osteopontin, TIMP1, VEGF, or vWF level; heart to brain weight ratio; left ventricle (LV) mass; cardiac output; stroke volume; and % ejection fraction; in a subject, administering a pharmaceutical composition comprising a GDF15 molecule to the subject, and after a desired period of time, measuring the level of one or more of body weight; heart weight; adiponectin level; decrease in glucose, triglycerides, cholesterol, or insulin levels; c-peptide, proinsulin, amylin or glucagon level; aldosterone, FABP3, IL-16, or ST2 level; heart rate; Tau level; E/E' ratio; IVRT; running distance, time (e.g., time to exhaustion) or peak VO2; NGAL, KIM-1, or clusterin level; sE-selectin, sICAM, Myl3, osteopontin, TIMP1, VEGF, or vWF level; heart to brain weight ratio; left ventricle (LV) mass; cardiac output; stroke volume; and % ejection fraction; in the subject. The two levels can then be compared to determine the relative change in the subject. Depending on the outcome of that comparison another dose of the pharmaceutical composition can be administered to achieve a desired level of one or more metabolically-relevant compound.

A GDF15 molecule (and optionally, its corresponding Fc molecule) can be administered in combination with another therapeutic agent, such as an agent that decrease in body weight or heart weight; increase in adiponectin; decrease in glucose, triglycerides, cholesterol, or insulin levels; changes in levels of c-peptide, proinsulin, amylin or glucagon; decrease in level of aldosterone, FABP3, IL-16, or ST2; increase in heart rate; decrease in Tau level; decrease in E/E' ratio; decrease in IVRT; increase in running distance, time (e.g., time to exhaustion), or peak VO2; decrease in NGAL, KIM-1, or clusterin level; decrease in level of sE-selectin, sICAM, Myl3, osteopontin, TIMP1, VEGF, or vWF; decrease in heart to brain weight ratio; decrease in left ventricle (LV) mass; decrease in cardiac output; decrease in stroke volume, or decrease in % ejection fraction.

The detailed description and following examples illustrate the present invention and are not to be construed as limiting the present invention thereto. Various changes and modifications can be made by those skilled in the art on the basis of the description of the invention, and such changes and modifications are also included in the present invention.

EXAMPLES

The following examples, including the experiments conducted and results achieved, are provided for illustrative purposes only and are not to be construed as limiting the present invention.

Example 1: In Vivo Study Design for Characterization of ZSF1 Obese Rat as Preclinical Model of Human Cardiometabolic Syndrome Eighteen-week-old ZSF1 male Lean (strain 379, n=14) and ZSF1 Obese (strain 378, n=14) rats were purchased from Charles Rivers Laboratories (Kingston, N.Y., USA) and single-housed at an accredited facility. After 2 weeks of acclimation both groups (n=8 per group) were subjected to the blood collection via tail vein, echocardiography, hemodynamic assessment and to evaluation of exercise endurance (time and distance) using a treadmill regimen. The separate cohort from the same batch of acclimated ZSF1 obese (n=6) and lean (n=6) rats was subjected to the heart isolation, RNA extraction and expression analysis of RNAseq results.

Example 2: In Vivo Study Design for the Evaluation of GDF15 Treatment Effect on Cardiometabolic Syndrome Specific Biomarkers in ZSF1 Obese Rats Twenty-week-old ZSF1 obese male rats (strain 378, n=30) were purchased from (Charles Rivers Laboratories Kingston, N.Y., USA) single-housed at an accredited facility and acclimated for 2 weeks. At 22 weeks of age, the baseline blood collection (for metabolic biomarkers evaluation) and body weight assessment were performed for all the animals. Twenty-four hours later rats were randomized into two groups and injected subcutaneously once a week for 12 weeks with either A5.2Su buffer (Vehicle group, n=15) or 1.5 mg/kg of FcΔ10(−)-(G4S)4-GDF15 (SEQ ID NO: 39, see PCT Application No. PCT/US19/26369, which is incorporated by reference in its entirety) and FcΔ10(+,K) (SEQ ID NO: 32) (FC-GDF15 group, n=15). For the duration of a study all the rats were subjected to the weekly: (1) blood collection, (2) food intake and (3) bodyweight assessments. At the end of the study rats from both treatment groups were subjected to echocardiography, hemodynamic assessment and to evaluation of exercise endurance (time and distance) using a treadmill regimen.

Example 3: Evaluation of Cardiovascular, Kidney Injury and Metabolic Biomarkers in Serum/Plasma Prior to the blood collection animals were fasted for 4 hours. The first 0.5 ml aliquot of whole blood was collected from the tail vein into a serum separator tubes (Microtainer; Becton Dickinson; Franklin Lakes, N.J., USA) and the second 0.5 ml aliquot of whole blood was in EDTA plasma separation tube (Microtainer; Becton Dickinson; Franklin Lakes, N.J., USA). Separated serum/plasma was aliquoted and stored at −80° C. Blood glucose levels were measured using AlphaTrak 2 glucose strip (Abbott Laboratories, Lake Bluff, Ill., USA). Blood insulin was evaluated by rat insulin ELISA kit (Alpco, Salem, N.H., USA). Serum triglyceride and cholesterol levels were measured weekly by triglyceride quantitation kits (Fisher Diagnostics, Middletown, Va., USA). Systemic levels of GDF15 (R&D Systems, Minneapolis, Minn., US) and proinsulin (Mercodia, Uppsala, Sweden) in serum/plasma of 20-week-old ZSF1 male rats were evaluated by commercial ELISAs. The limited array of metabolic hormones in circulation (Amylin (active), C-Peptide 2, Ghrelin (active), GIP (total), GLP-1 (active), Glucagon, IL-6, Leptin, PP, PYY) was assessed in serum/plasma collected from ZSF1 obese and lean cohorts at the age of 20 weeks by rat-specific MILLIplex kit (Millipore; Billerica, Mass., USA). Kidney injury markers KIM-1 and NGAL were evaluated in serum from 20-week-old ZSF1 obese and lean cohorts by multiplex MILLIplex kits (Millipore; Billerica, Mass., USA). Serum NT-proBNP and rat cardiac injury markers (FABP3, Myl3) were measured by using rat-specific single-plex or multi-plex commercial assays from Meso Scale Diagnostics (Rockville, Md., USA). Systemic levels of vascular markers were evaluated at the end of FC-GDF15 or Vehicle treatment of ZSF1 obese rats by using multiplex MILLIplex kits (Millipore; Billerica, Mass., USA): Rat Vascular injury panels included VEGF, MCP1, TIMP1, TNFa, vWF, Adiponectin, sE-Selectin and sICAM1. Systemic aldosterone was measured by enzyme immunoassay (m/r/h Aldosterone ELISA, Enzo Life Sciences, Farmingdale, N.Y., USA) and serum ostepontin—by rat Single plex kit (Rat Millipore; Billerica, Mass., USA). All the assays were performed in accordance with manufacturer protocols.

Example 4: RNA Isolation and Sequencing Analysis of Left Heart

At scheduled necropsy, left atria and left ventricle of the heart were washed briefly in RNase-free saline, placed in cryo-tubes, snap-frozen in liquid nitrogen, and stored at −80° C. Samples were subjected to dry pulverization before being homogenized in buffer (350 μL of Qiagen RLT buffer with 10% BME; Qiagen [Germantown, Md., USA]). The homogenate was transferred to an RNase-free 1.5 mL centrifuge tube, after which 95 μL RNase-free water and 5 μL of a 20 mg/mL Proteinase K solution were added. Samples were incubated at 55° C. for 10 minutes, centrifuged and the supernatant collected. RNA was then extracted using RNeasy Micro Kit (Qiagen) with on-column DNase treatment (Qiagen) according to manufacturer's instructions. RNA concentration and integrity were assessed using a Bioanalyzer (Agilent [Santa Clara, Calif., USA]). Samples with ≥80 ng total RNA that had RNA integrity numbers≥7 were used for sequencing (Supplemental Table IV). Principal component analysis was performed on log 2 (Fragments per Kilobase per Million Quantile normalized [FPKQ])

values for each time point using OmicSoft's Array Studio software (www.omicsoft.com/array-studio.php; Oshell.exe v10.0).

Example 5: Differential Expression and Pathway Analysis

RSEM was used to calculate gene expression levels and DESEQ2 was used to identify differentially expressed genes (DEGs) by BH adjusted p value less than 0.05 and fold change more than 1.5. The analysis of the genes that have human homologue and are abundant in human heart was based on GTEX data. All the DEGs and heart abundant DEGs were further annotated by ingenuity pathway analysis (IPA). Metabolic and cardiac signaling pathway enrichment was done on the significantly differentially expressed genes by adjust p-value cutoff of 0.05 through the use of IPA (QIAGEN, Redwood City, Calif., US). Gene expression enrichment in cardiac diseases was analyzed by using Medical Subject Headings (MeSH) terms with meshes R package (Yu G. Using meshes for MeSH term enrichment and semantic analyses. *Bioinformatics,* 2018, 34(21), 3766-3767). Dotplots were generated with enrichplot R package (Yu G. Enrichplot: Visualization of Functional Enrichment Result. R package version 1.4.0. https://github.com/GuangchuangYu/enrichplot, 2019)

Example 6: Echocardiography

Non-invasive echocardiograms were obtained on anesthetized rats (isoflurane, 3% induction, 1.5% maintenance) using a Vevo 2100 imaging system. Animals were shaved, placed on a stage, and a thermo-couple probe was used to assess body temperature and to adjust the temperature of the platform to maintain normothermia. Sonography gel was applied on the thorax. Two-dimensional targeted B-mode and M-mode imaging was obtained from the long-axis and short-axis view at the level of the papillary muscle. Coronary flow was measured by Pulsed-Wave (PW) Doppler and movement of the LV wall measured by Tissue Doppler by placing the probe to the chest and focusing image on region of the ventricular wall to achieve an apical four chamber view Animals were subsequently wiped clean of sonography gel, allowed to achieve consciousness, and returned to their home cage.

Example 7: Invasive Hemodynamic Assessment

Animals underwent general anesthesia using ketamine/diazepam (IP) injection (80 to 100 mg/kg ketamine; 5 to 10 mg/kg diazepam) followed by a ketamine boost (10 to 20 mg/kg) as necessary to maintain anesthesia plane. Anesthetized animals had the surgical sites shaved with a small animal shear Animals were then placed on a heated surgical platform, and body temperature was monitored and maintained throughout the study via a rectal probe. Arterial pressure was measured via femoral artery catheterization (SPR-839, Millar). An incision in the medial aspect of the leg was made and the fat overlaying the femoral vessels and femoral nerve in the area between the abdominal wall and the upper leg was gently teased apart using forceps or Q-tips. The fascia overlying the artery, nerve and vein was removed. The artery was isolated and ligated by a distal suture and a loose tie was held in place using a hemostat. A microvessel clip or suture was placed on the artery near the abdominal wall and a small incision was made into the vessel using Vannas micro-scissors or a 25-gauge needle. The clip was released by one hand, and the Millar catheter was advanced quickly into the femoral artery, followed by the tightening of the proximal suture to prevent blood loss. Pressure was then recorded. Left ventricular pressure and volume were measured via carotid artery catheterization (SPR-838, Millar). The right carotid artery was isolated, and a suture was tied around the vessel approximately 0.25 cm below the skull base to disrupt blood flow. A suture was placed around the artery near the rib cage and held in place using a hemostat. A small incision was made into the vessel using Vannas micro-scissors or a 25-gauge needle. The clip was released by one hand, and the Millar catheter was advanced quickly into the carotid artery, followed by the tightening of the proximal suture to prevent blood loss. The catheter was advanced until it entered the left ventricle for pressure-volume loop measurement Animals were euthanized under anesthesia after completion of the data acquisition.

Example 8: Treadmill Assessment

Rats were subjected to evaluation of exercise endurance (time and distance) using a treadmill regimen. Endurance exercise performance were estimated using two parameters: run duration (min.) and distance (m). Oxygen consumption, an indicator of exercise capacity, was measured by monitoring the O2 concentration of expired air. Peak chamber oxygen decrement, which usually occurs just prior to exhaustion, was used to calculate and define the animal's peak VO2. The contribution of anaerobic metabolism to overall energy production during exercise was estimated by calculating the respiratory exchange ratio (RER), the ratio of VO2 to VCO2 (the amount of CO2 within the chamber just prior to exhaustion). Rats were initially familiarized to the motorized rodent treadmill (Columbus Instruments, Columbus, Ohio) for 5 days before completing the exercise performance test. Rats were placed on the treadmill and allowed to adapt to the surroundings for 2-5 minutes before starting. Familiarization runs consisted of 10 minutes of running on an incline of 10 degrees at a speed of 12 m/min. For the treadmill challenge, rats were placed on the treadmill and allowed to adapt to the surroundings for 2-5 minutes before starting. The treadmill was initiated at a speed of 8.5/min with a zero-degree incline. After 3 minutes, the speed and incline were raised up to 10 m/min. The incline was subsequently increased progressively by 2.5 m/min every 3 min. The incline was progressively increased by 5 degrees every 9 min. to a maximum of up to 30 degrees. Exercise continued until exhaustion, which is defined as the inability to maintain running speed despite repeated contact with the electric grid (3 shocks in less than 15 seconds).

Example 9: Statistical Analysis

Results for serum protein biomarkers are expressed as mean±SEM. Differences between the two groups were examined between ZSF1 Lean and ZSF1 OB rats of the same age or at the end of the hGDF15 treatment (wk12) between Vehicle-treated and hGDF15-treated ZSF1 OB rats. Unpaired Student's t test was performed to evaluate the statistical significance between the groups. A value of $p<0.05$ was used to determine statistical significance.

The RNAseq data set from each cohort was analyzed separately, genes with FPKQ≥1 in ≥5 samples in the pairwise group comparison were selected for further statistical testing. Differential expression analysis was performed using DESeq2 version 1.10.1 for group comparison (Love, M. I., et al. (2014). "Moderated estimation of fold change and dispersion for RNA-seq data with DESeq2." *Genome Biol* 15(12): 550). For a given comparison, raw reads counts for genes were compared between the 2 conditions using DESeq2 following a negative binomial distribution, and gene expression fold changes were calculated using normalized counts. Genes with Benjamini-Hochberg corrected p-value<0.05 and fold change between the two conditions≥1.5 or ≤0.5 were selected as significantly differentially expressed genes. Stars (*) indicate significance: * p<0.05,  p<0.01, * p<0.001, **** p<0.0001.

Example 10: Gene Models Used for Alignment and Quantification

RNA-Seq alignment and quantification utilized slightly modified versions of the gene model, genome build 38 using GENCODE v24 annotation, curated by OmicSoft (Cary, N.C., USA). The modifications to the gene models imposed a more stringent definition of the term "gene", requiring that all of the gene's transcripts reside on the same chromosome and strand, and that the distance between a gene's transcripts not span more than 10 kilobases that is not covered by any (un-spliced) transcript. Genes that violated this definition were split into multiple genes to comply with these criteria, and the gene names were appended with a suffix indicating the strand, chromosome name, and transcript bundle number.

Example 11: Read Filtering and Trimming

All read files were pre-processed to remove poor quality reads and to trim poor quality 3' bases. First, any read pair containing a read that failed the Illumina quality filter was removed. Next, all reads were trimmed from the 3' terminus until either (1) the read length was reduced to 40 bp, or (2) less than 2 of the bases in the 5 base window at the 3' terminus of the read had a quality scores value below 3. This trimming included a final polishing step in which the base at the 3' terminus was trimmed if the read length exceeded 40 bp and the quality score of the base was below 3.

Example 12: Alignment and Quantification

The filtered and trimmed reads were aligned and quantified using OmicSoft's Array Studio software (www.omicsoft.com/array-studio.php; Oshell.exe v10.0). This software compared favorably to other commonly used tools (eg Tophat/Cufflinks, MMSEQ) in internal benchmark comparisons. The alignment algorithm is documented in an OmicSoft whitepaper (www.omicsoft.com/downloads/whitepaper/OmicsoftAligner.pdf), and the gene/transcript quantification module is an OmicSoft implementation of the RSEM algorithm (Li, B. and C. N. Dewey (2011). "RSEM: accurate transcript quantification from RNA-Seq data with or without a reference genome." *BMC Bioinformatics* 12: 323).

Example 13: Differential Expression Analysis

Genes with critical issues on gene models, including duplicated regions, high GC content and overlapping transcripts were removed from statistical analysis. RNA-Seq data set from each time point was analyzed separately. For each time point, genes expressed at FPKQ>=1 in at least 5 samples were selected for further statistical test. Differential Expression Analysis was performed using DESeq2 version 1.18.1 (Love, M. I., et al. (2014)). Raw read counts from the selected genes were compared using R Bioconductor package DESeq2 following Negative Binomial distribution. Gene expression Fold Changes were calculated using normalized counts. Genes with BH corrected p value<0.05 and Fold Change>=1.5 or <=⅔ were selected as significantly differentially expressed genes.

Example 14: Expression Normalization

The gene- and transcript-level expression of each RNA-Seq sample was reported by Oshell as an FPKM (Fragments per Kilobase per Million sequenced) value. FPKM is an expression measurement based on the count of library fragments that map to a given feature (gene or transcript) normalized for feature length and the number of fragments sequenced. These values were adjusted on a per-sample basis using $70^{th}$ percentile normalization, yielding a final expression metric which is referred to as "FPKQ".

Example 15: ZSF1 Obese Rats Exhibit Obesity and Impaired Metabolism

ZSF1 obese male rats at the age of 20 weeks exhibited impaired markers of metabolism as shown in Table 7 and FIG. 1.

TABLE 7

Metabolic and renal biomarkers in serum/plasma^ of 20-week-old ZSF1 Lean and ZSF1 QB male rats

| | Serum concentration (Mean ± SEM) | | |
|---|---|---|---|
| Biomarker | ZSF1 Lean | ZSF1 OB | P value |
| Cholesterol (mg/dl) | 64.6 ± 2.0 | 271.1 ± 13.4 | <0.0001 |
| Triglycerides (mg/dl) | 118.5 ± 7.6 | 3239 ± 163 | <0.0001 |
| BUN (mg/dl) | 20.5 ± 0.5 | 23.5 ± 1.0 | 0.0178 |
| LDL (mg/dl) | 11.2 ± 0.3 | 12.0 ± 0.6 | 0.2749 |
| Glucose (mg/dl) | 110.0 ± 3.6 | 350.6 ± 29.4 | <0.0001 |
| Insulin^ (ng/ml) | 2.9 ± 0.6 | 11.1 ± 2.9 | 0.0164 |
| Pro-insulin^ (pmol/L) | 27.8 ± 3.9 | 1337 ± 130 | <0.0001 |
| C-Peptide^ (ng/ml) | 2.4 ± 0.2 | 6.4 ± 0.4 | <0.0001 |
| Amylin^ (active, pg/ml) | 45.6 ± 8.1 | 288.6 ± 25.6 | <0.0001 |
| Leptin^ (ng/ml) | 6.8 ± 0.9 | 41.0 ± 6.3 | <0.0001 |
| GIP^ (pg/ml) | 223.1 ± 20.0 | 218.6 ± 51.3 | 0.9372 |
| Glucagon^ (pg/ml) | 25.8 ± 2.5 | 37.8 ± 4.6 | 0.0388 |
| PP^ (pg/ml) | 26.1 ± 3.9 | 34.6 ± 8.0 | 0.3599 |
| PYY^ (pg/ml) | 32.8 ± 3.0 | 106.3 ± 13.8 | <0.0001 |
| Adiponectin^ (μg/ml) | 2.58 ± 0.09 | 1.85 ± 0.05 | <0.0001 |
| Clusterin (μg/ml) | 8.6 ± 0.2 | 12.0 ± 0.4 | <0.0001 |
| KIM-1 (pg/ml) | 294.0 ± 7.0 | 641.8 ± 94 | 0.0024 |
| NGAL (ng/ml) | 43.7 ± 2.4 | 66.1 ± 4.3 | 0.0005 |
| MCP1 (ng/ml) | 1.19 ± 0.09 | 1.28 ± 0.12 | 0.1497 |
| TNFa (pg/ml) | 29.4 ± 3.4 | 12.6 ± 2.9 | 0.0022 |
| IL-1b (pg/ml) | 39.1 ± 6.6 | 121.4 ± 26.7 | 0.0098 |
| TGFb (ng/ml) | 75.1 ± 1.5 | 70.0 ± 3.4 | 0.1934 |
| TIMP1 (ng/ml) | 3.33 ± 0.47 | 4.21 ± 0.34 | 0.1524 |

ZSF1 obese male rats at the age of 20 weeks exhibited dramatically elevated body weight (38% increase vs. lean group, p<0.0001), significantly increased blood glucose (1.6 fold, p=0.0060), serum insulin (14.7 fold, p=0.0019), cholesterol (2.9 fold, p<0.0001) and triglyceride (15 fold, p<0.0001) levels relative to ZSF-1 lean littermate controls (FIGS. 1A-1E, respectively). Significant decrease in serum adiponectin from 2.6±0.09 μg/ml in ZSF1-lean serum to 1.9±0.05 μg/ml in ZSF1-obese serum (p<0.0001) (FIG. 1F) indicated deposition of newly formed visceral fat and served as a reliable obesity biomarker.

Example 16: ZSF1 Obese Rats Demonstrate Pancreatic and Renal Disfunction

Figure 2B:
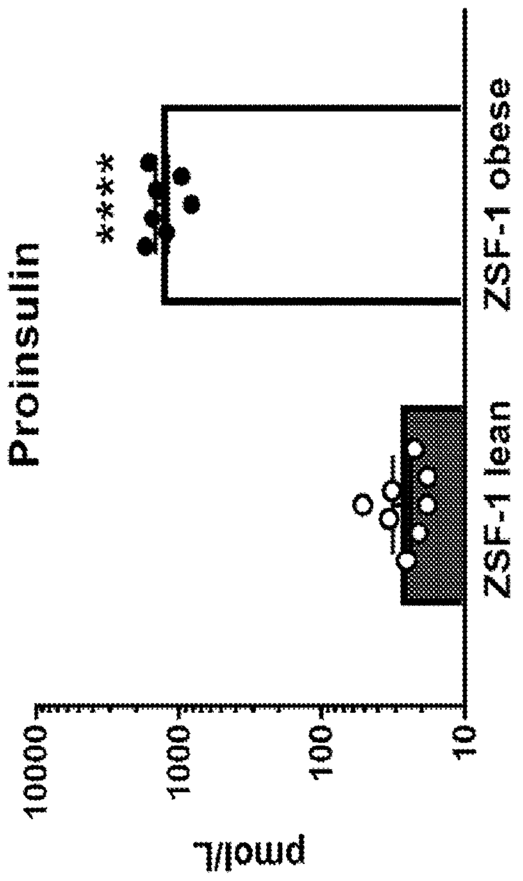
FIG. 2. ZSF1 obese rats demonstrate pancreatic disfunction as demonstrated with significant increase of C-peptide (FIG. 2A), proinsulin (FIG. 2B) active amylin (FIG. 2C) and glucagon (FIG. 2D). ZSF1 obese rats exhibit impaired renal function by increased serum levels of kidney injury markers NGAL (FIG. 2E), KIM-1 (FIG. 2F) and clusterin (FIG. 2G). Stars (*) indicate significance (* p<0.05,  p<0.01, * p<0.001, **** p <0.0001), unpaired two-tailed t-test.
Figure 2A:
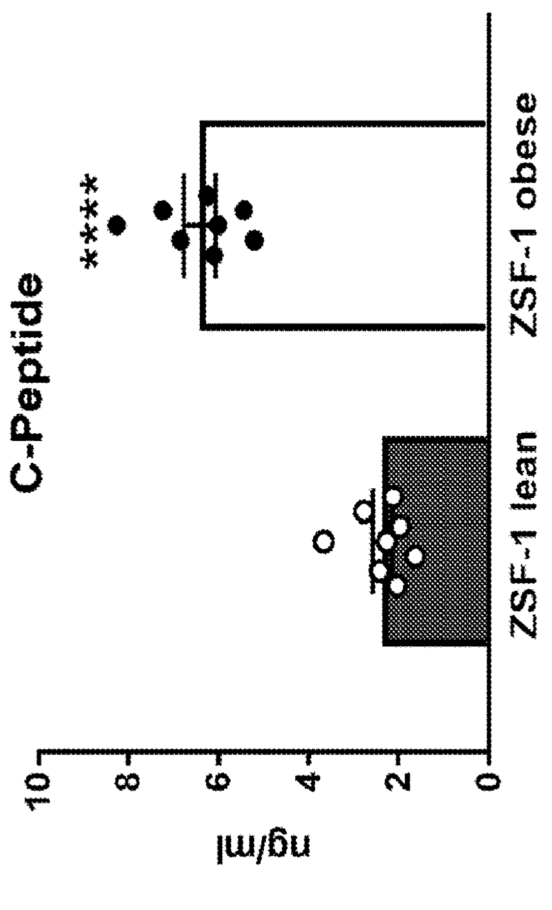
Figure 2C:
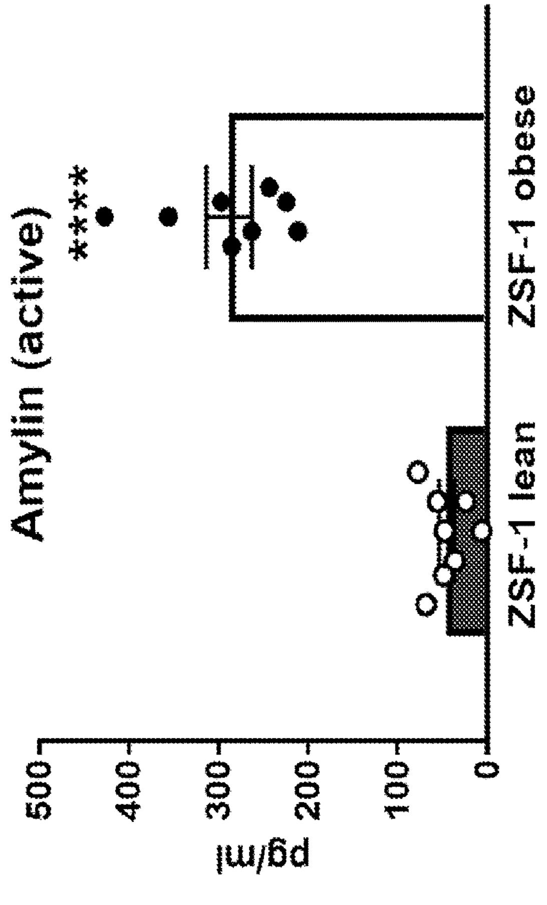
Figure 2D:
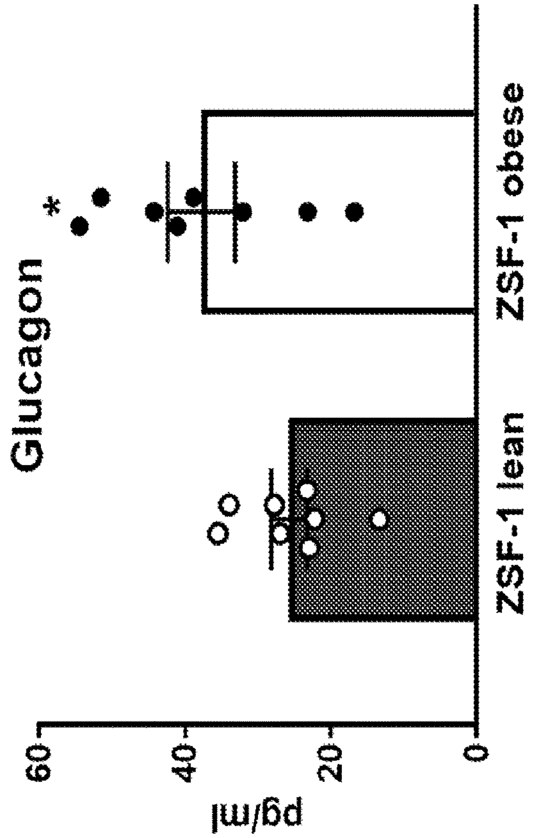
Figure 2E:
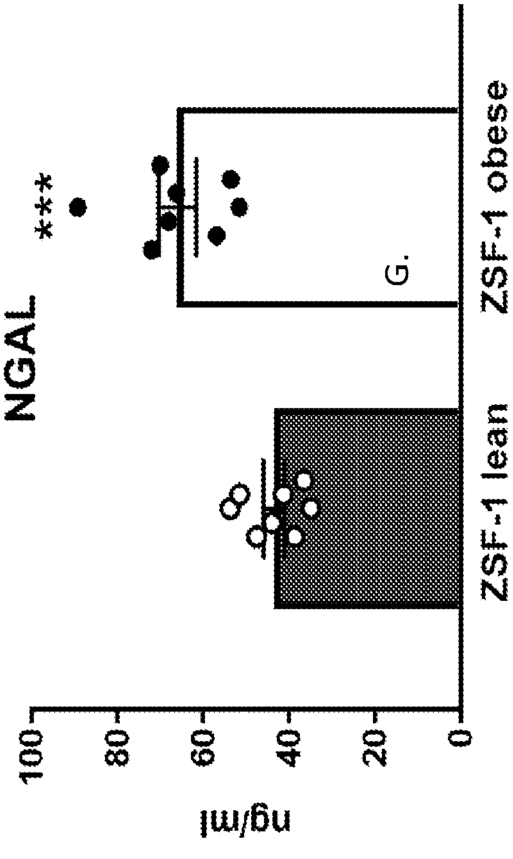
Figure 2F:
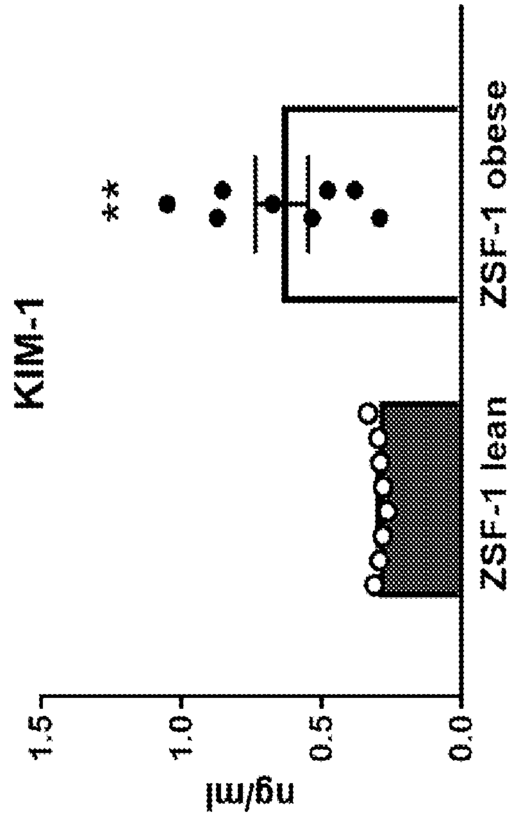
Figure 2G:
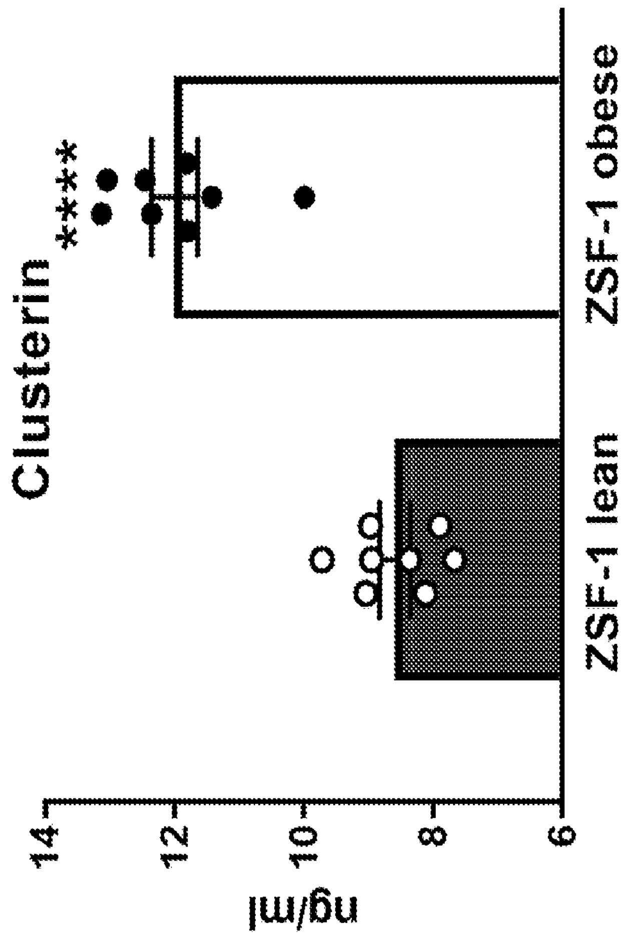

Since the array of biomarker changes relevant to the progression and establishment of cardiomatabolic syndrome in humans includes type 2 diabetes and renal impairment, the systemic levels of major pancreatic and kidney injury biomarkers in ZSH1-obese rats were evaluated and compared with their lean littermates (Table 7). ZSF1 obese male rats at the age of 20 weeks demonstrated pancreatic disfunction significantly as shown by 2.7 folds elevated systemic C-peptide (FIG. 2A), 47 folds increased proinsulin (FIG. 2B), 6.3 folds raised serum active amylin (FIG. 2C) and moderately, but significantly elevated glucagon (37.8±4.6 in ZFF1 obese vs 25.8±2.5 pg/ml in ZSF1 lean littermates, p=0.0388; FIG. 2D). Impaired renal function in the ZSF1 obese cohort was characterized by significantly increased serum kidney injury markers, NGAL (1.5 folds vs ZSF1 lean, FIG. 2E), KIM-1 (2.2 folds vs ZSF1 lean, FIG. 2F) and clusterin (1.4 folds vs ZSF1 lean, FIG. 2G).

Example 17: ZSF1 Obese Rats Exhibit Diastolic Dysfunction and Reduced Exercise Capacity The complete results of invasive hemodynamic assessment, echocardiography and exercise capacity of 20-21-week-old ZSF1 obese and lean male rats are presented in Table 8.

TABLE 8

Invasive hemodynamic assessment, echocardiography and exercise capacity of 20-21-week-old ZSF1 obese and lean male rats

| | Physical parameters (Mean ± SEM) | | |
|---|---|---|---|
| Biomarker | ZSF1 Lean | ZSF1 OB | P value |
| Heart/Brain Weight (ratio) | 0.68 ± 0.03 | 0.81 ± 0.01 | 0.0070 |
| Heart Rate (bpm) | 371.2 ± 9.5 | 292.8 ± 4.1 | <0.0001 |
| Diameter (s) (mm) | 3.59 ± 0.18 | 4.37 ± 0.34 | 0.053 |
| Diameter (d) (mm) | 8.0 ± 0.13 | 9.21 ± 0.28 | 0.0011 |
| Volume (s) (μl) | 56.07 ± 6.29 | 91.23 ± 14.71 | 0.0383 |
| Volume (d) (μl) | 345.8 ± 11.94 | 474.8 ± 29.16 | 0.0009 |
| Stroke Volume (μl) | 289.7 ± 10.0 | 383.5 ± 18.65 | 0.0005 |

TABLE 8-continued

Invasive hemodynamic assessment, echocardiography and exercise capacity of 20-21-week-old ZSF1 obese and lean male rats

| | Physical parameters (Mean ± SEM) | | |
|---|---|---|---|
| Biomarker | ZSF1 Lean | ZSF1 OB | P value |
| Ejection Fraction (%) | 83.93 ± 1.6 | 81.45 ± 2.32 | 0.3839 |
| Fractional Shortening (%) | 50.03 ± 1.97 | 52.89 ± 2.56 | 0.4919 |
| Cardiac Output (ml/min) | 107.4 ± 4.3 | 112 ± 5.1 | 0.4990 |
| LV Mass (mg) | 1274 ± 124.2 | 1445 ± 41.1 | 0.2384 |
| LV Mass Cor (mg) | 1019 ± 99.4 | 1156 ± 32.9 | 0.2384 |
| IVRT (ms) | 20.12 ± 0.55 | 24.89 ± 0.67 | <0.0001 |
| EDP (mmHg) | 1.808 ± 1.116 | 3.445 ± 1.342 | 0.3669 |
| Tau (ms) | 6.83 ± 0.33 | 9.53 ± 46 | 0.0004 |
| E/E' (Ratio) | 16.25 ± 1.07 | 25.07 ± 2.65 | 0.0064 |
| Distance (m) | 394.9 ± 27.9 | 194.0 ± 6.5 | <0.0001 |
| Time to Exhaustion (min) | 27.13 ± 1.34 | 17.75 ± 0.53 | <0.0001 |
| Peak VO2 (mg · kg-1 · hr-1) | 3541 ± 130 | 2927 ± 33.4 | 0.0004 |
| Respiratory Exchange (Ratio) | 0.993 ± 0.017 | 0.9583 ± 0.015 | 0.1452 |

Figure 3A:
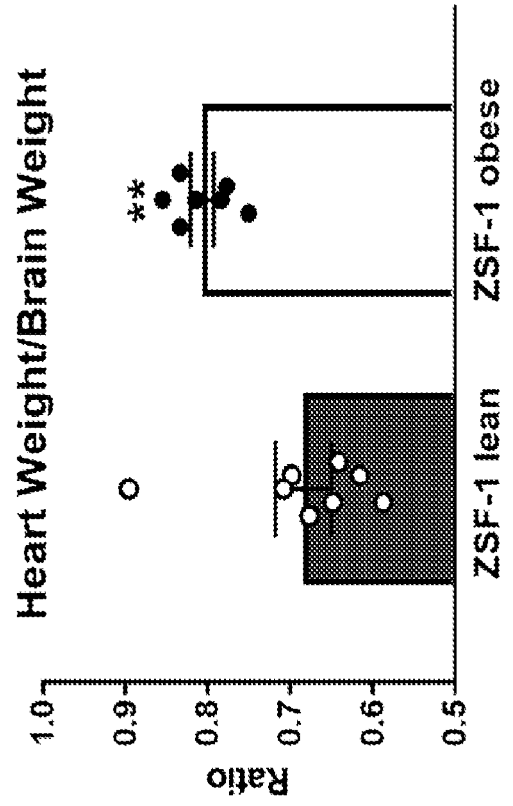
FIG. 3. ZSF1 obese rats exhibit diastolic dysfunction and decreased exercise capacity. The heart to brain weight ratio (by echocardiography) was significantly higher in ZSF1 obese rats (FIG. 3A), invasive hemodynamic assessment provides evidence of diastolic dysfunction by increased Tau (FIG. 3B) when compared to ZSF-1 lean rats. Echocardiography reveals that ZSF1 obese rats exhibit a decrease in heart rate (FIG. 3C) and diastolic dysfunction by increase in the E/E' ratio (FIG. 3D) and IVRT (FIG. 3E), while % EF is not different from ZSF1 lean (FIG. 3F) cohort. ZSF1 obese rats exhibit decreased exercise capacity as measure by distance (FIG. 3G), time (FIG. 3H), and peak VO2 (FIG. 3I). Stars (*) indicate significance (* p<0.05,  p<0.01, * p<0.001, **** p <0.0001), unpaired two-tailed t-test.
Figure 3B:
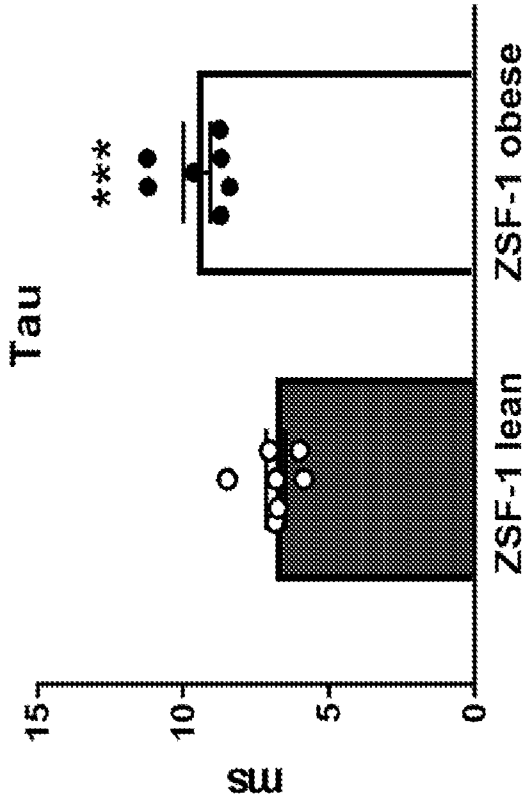
Figure 3D:
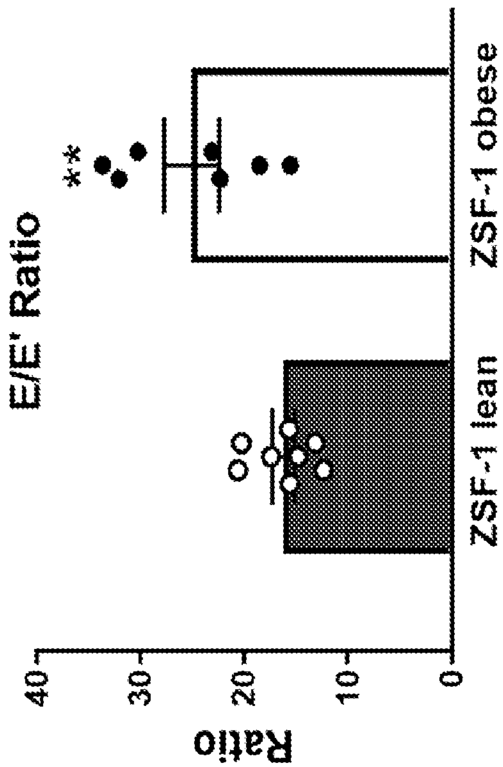
Figure 3C:
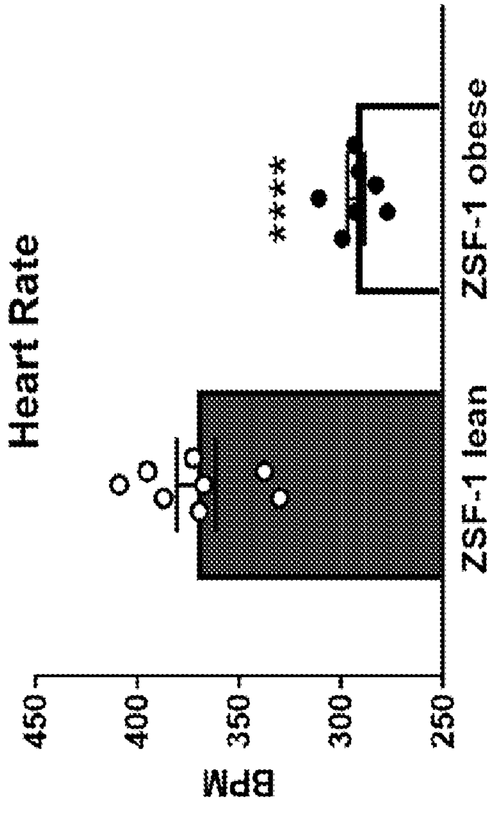
Figure 3F:
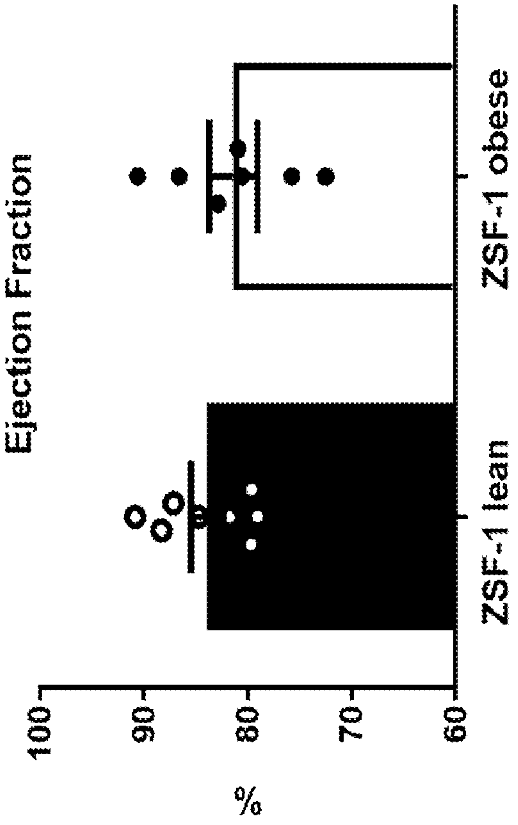
Figure 3E:
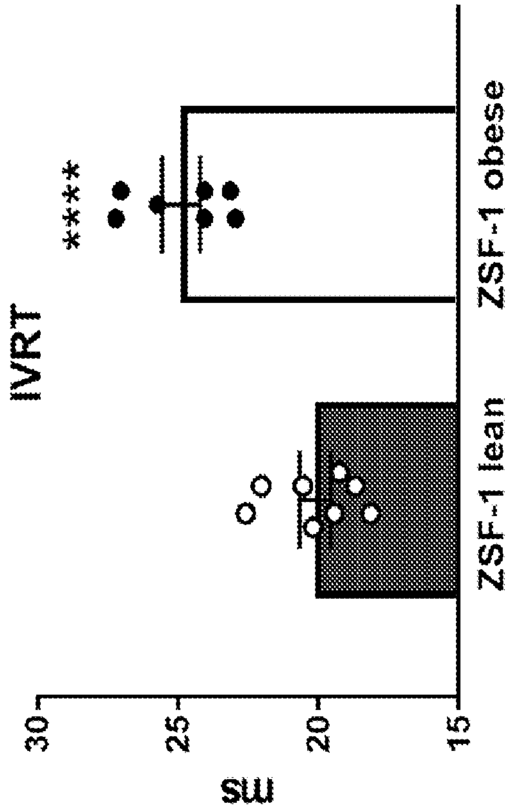
Figure 3H:
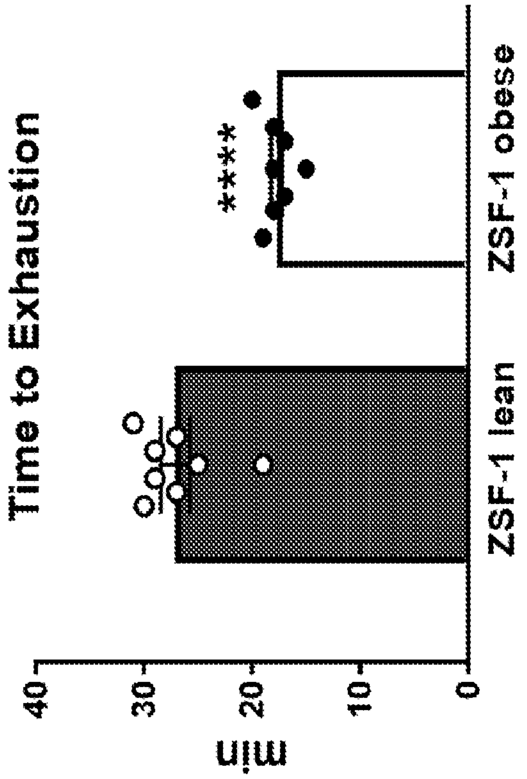
Figure 3G:
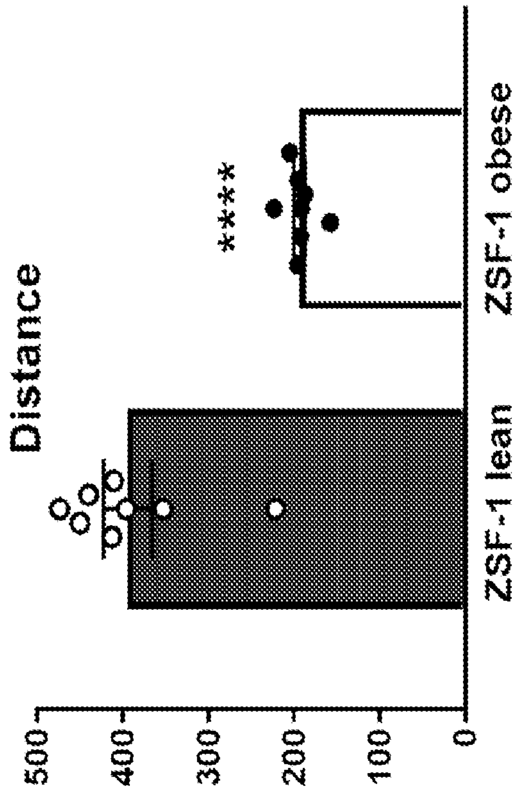
Figure 3I:
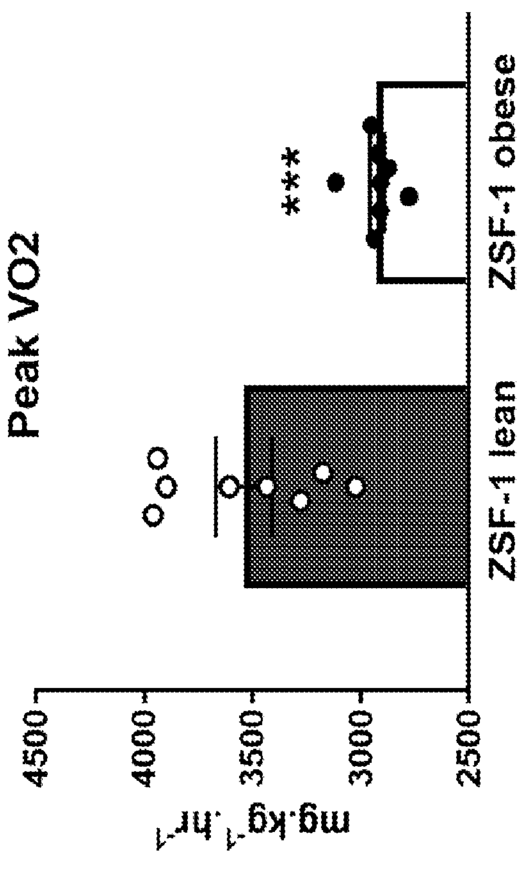

The heart to brain weight ratio was significantly higher in ZSF1 obese rats compared to ZSF1 lean (FIG. 3A). Invasive hemodynamic assessment at 21 weeks under ketamine/diazepam anesthesia revealed an increased relaxation constant tau (FIG. 3B). Echocardiography at 20 weeks under isoflurane anesthesia revealed that ZSF1 obese rats exhibit a significant increase in heart rate (FIG. 3C), E/E' (FIG. 3D) and IVRT (FIG. 3E) while maintaining a normal ejection fraction (FIG. 3F). It was further demonstrated that ZSF-1 obese rats exhibit a limited exercise capacity with significantly shorter distance (FIG. 3G), shorter times to exhaustion (FIG. 3H), and lower peak VO2 (FIG. 3I) following treadmill challenge.

Example 18: ZSF1 Obese Rats Exhibit Changes in Biomarkers of Cardiovascular Function To evaluate the translational value of ZSF1 obese rat model for human cardiometabolic syndrome, the major systemic cardiovascular diseases biomarkers were profiled (Table 9, FIGS. 4A-4F) and compared to the results with the gene expression of the same markers in the left heart of 20-week-old ZSF1 obese and lean male rats.

TABLE 9

Cardiovascular biomarkers in circulation of 20-week-old male ZSF1 obese and lean rats

| | Serum/plasma^ concentration (Mean ± SEM) | | |
|---|---|---|---|
| Biomarker | ZSF1 Lean | ZSF1 OB | P value |
| Follistatin-like 1 (ng/ml) | 8.11 ± 0.18 | 6.92 ± 0.17 | 0.0002 |
| Osteopontin (ng/ml) | 0.96 ± 0.02 | 0.96 ± 0.03 | 0.9845 |
| GDF15^ | 62.0 ± 1.8 | 161.9 ± 17.3 | <0.0001 |
| BNP^ (pg/ml) | 27.1 ± 3.4 | 34.7 ± 5.4 | 0.2512 |
| sE-Selectin^ (ng/ml) | 98.6 ± 5.4 | 93.8 ± 3.4 | 0.4497 |
| FABP3 (pg/ml) | 64.8 ± 6.15 | 185.9 ± 32.36 | 0.0025 |
| FABP4 (ng/ml) | 42.41 ± 7.34 | 56.54 ± 7.63 | 0.2030 |
| FABP5 (ng/ml) | 11.28 ± 0.52 | 18.84 ± 1.16 | <0.0001 |
| Aldosterone (ng/ml) | 0.708 ± 0.081 | 1.658 ± 0.223 | 0.0010 |

TABLE 9-continued

Cardiovascular biomarkers in circulation of 20-week-old male ZSF1 obese and lean rats

| Biomarker | Serum/plasma^ concentration (Mean ± SEM) | | |
|---|---|---|---|
| | ZSF1 Lean | ZSF1 OB | P value |
| NT-proANP (ng/ml) | 9.67 ± 0.75 | 9.17 ± 0.92 | 0.6768 |
| NT-proBNP (pg/ml) | 99.18 ± 12.55 | 34.91 ± 3.39 | 0.0002 |
| MYBPC3 | 15.32 ± 2.85 | 9.12 ± 1.79 | 0.0864 |
| IL-16 (pg/ml) | 55.4 ± 2.26 | 418.3 ± 50.3 | <0.0001 |
| ST2 (pg/ml) | 435.9 ± 18.8 | 711.7 ± 29.4 | <0.0001 |
| Endothelin-1 (ET1) (pg/ml) | 1.48 ± 0.09 | 1.9 ± 0.19 | 0.0686 |
| FLT1/VEGFR1 (pg/ml) | 16.9 ± 1.22 | 19.32 ± 2.15 | 0.3447 |

Figure 4B:
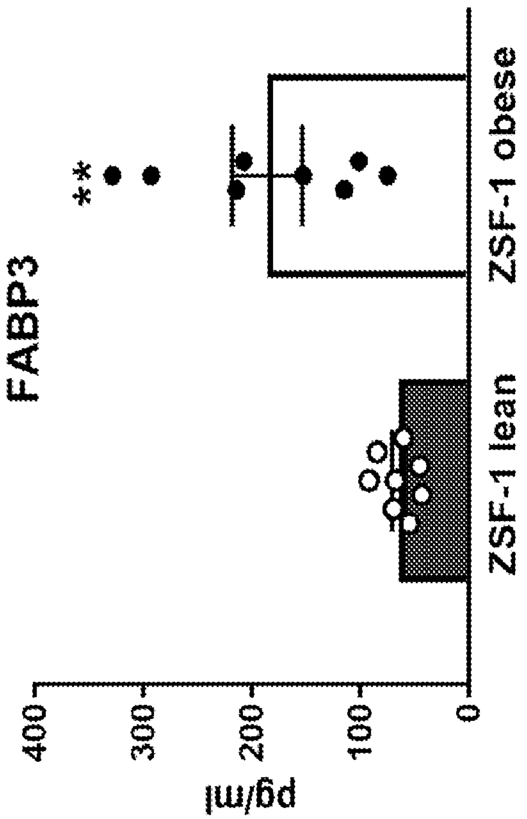
FIG. 4. Twenty-week-old ZSF1 obese male rats exhibit cardiovascular disfunction by increased blood levels of aldosterone (FIG. 4A), FABP3 (FIG. 4B), IL-16 (FIG. 4C) and ST2 (FIG. 4D). In ZSF1 obese rats, systemic concentration of NT-proBNP (FIG. 4E) is significantly lower compared to the lean rats and osteopontin (FIG. 4F) levels in circulation are not different between two groups of rats. The gene expression of NPPB (NT-proBNP protein, FIG. 4G) in left heart was not different between ZSF1 obese and lean rats, whereas the local SPP1 (osteopontin) (FIG. 4H) (expression in left atria and left ventricle was significantly elevated in ZSF1 obese rats. Stars (*) indicate significance (* p <0.05,  p<0.01, * p<0.001, **** p<0.0001), unpaired two-tailed t-test.
Figure 4A:
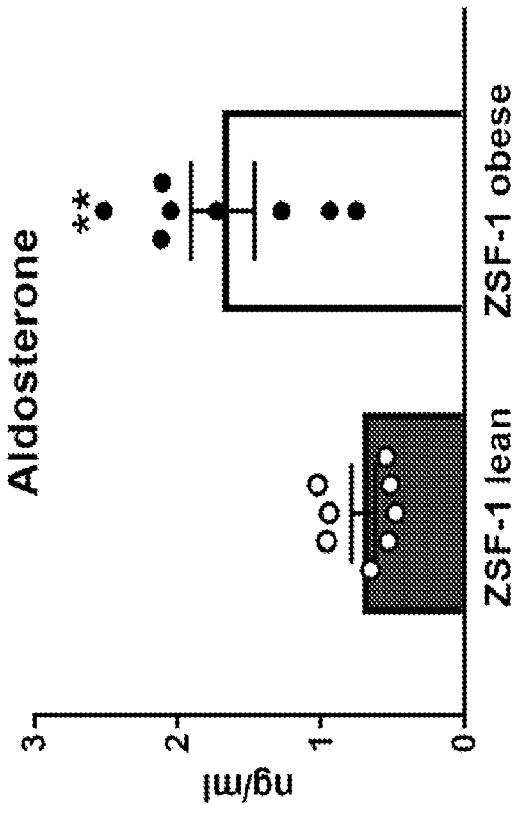
Figure 4D:
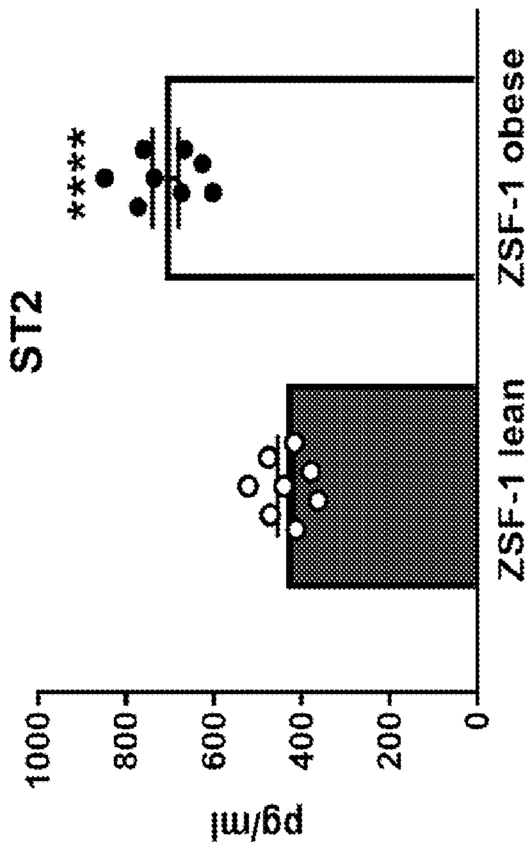
Figure 4C:
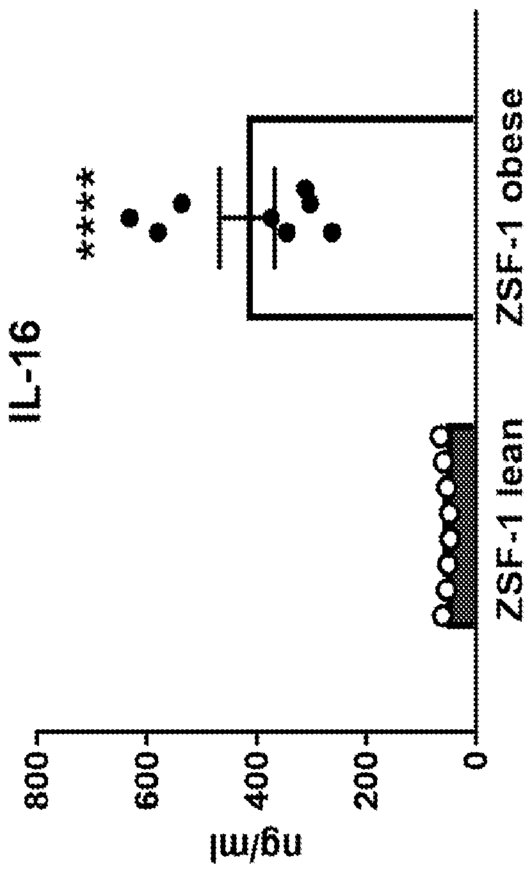
Figure 4E:
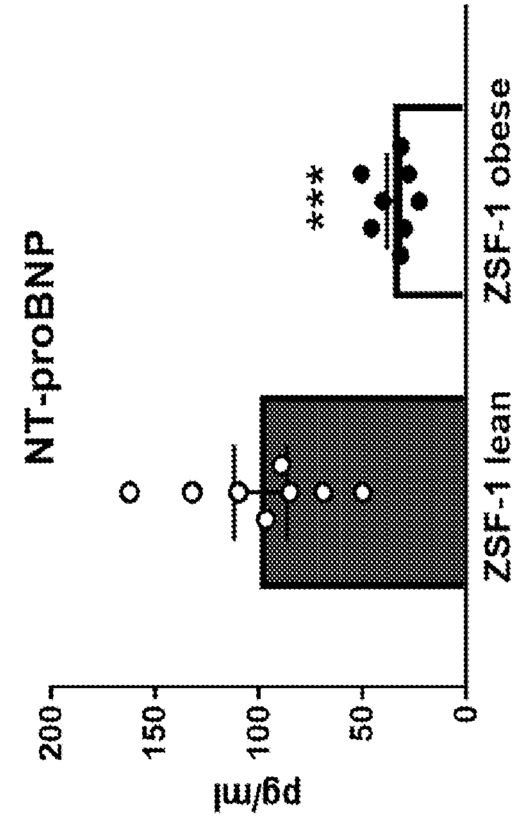
Figure 4F:
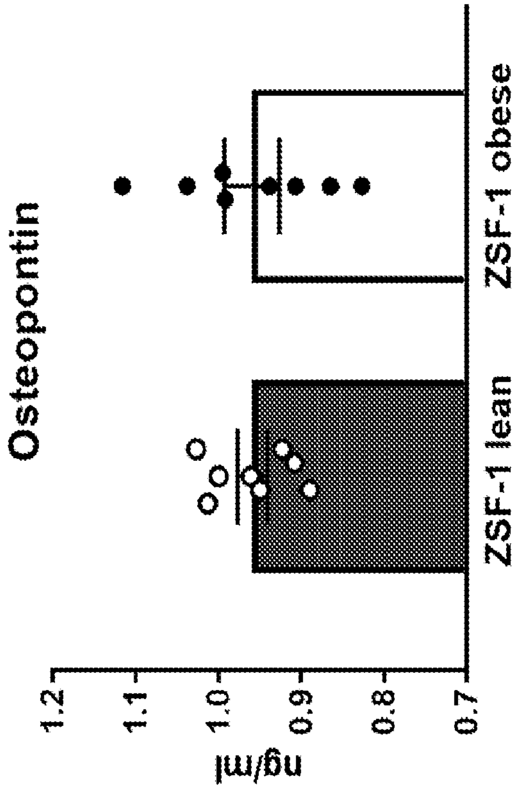
Figure 4G:
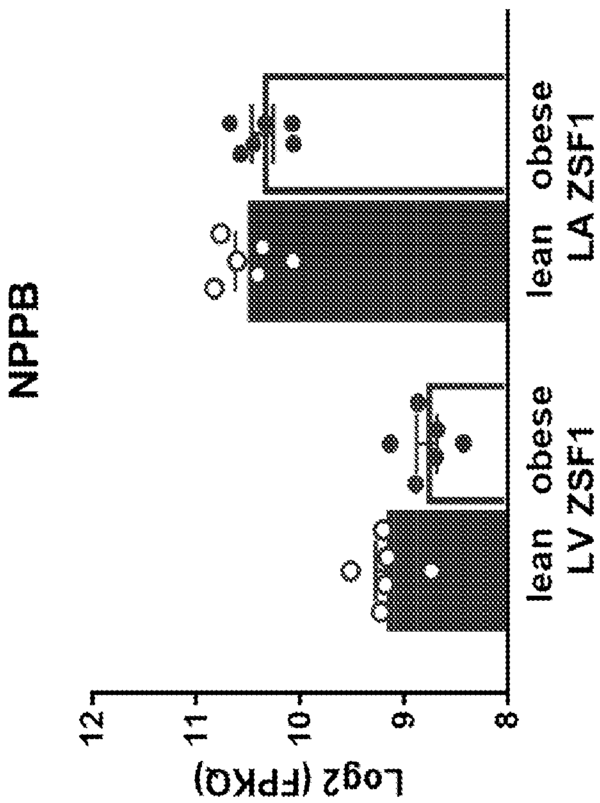
Figure 4H:
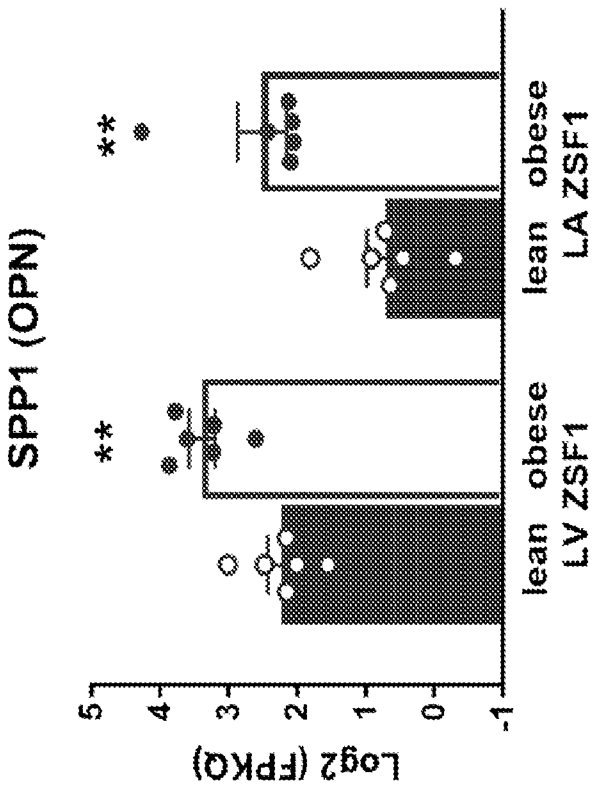

The array of systemic changes in CVD-related biomarkers included increased blood levels of the hypertension marker aldosterone (FIG. 4A), elevated levels of the biomarker of heart pathology FABP3 (FIG. 4B), and significantly increased vascular markers IL-16 (FIG. 4C) and ST2 (FIG. 4D) in serum. Systemic concentration of NT-proBNP (NPPB) (FIG. 4E) in ZSF1 obese rat was significantly lower vs. lean cohort, and osteopontin (OPN) (FIG. 4F) levels in circulation were not different between obese and lean ZSF1. The gene expression of above markers in left heart was not different between obese and lean ZSF1 for FABP3, IL-16, IL-1RL1 (data not shown) and NPPB (FIG. 4G), whereas the local SPP1 mRNA expression (osteopontin gene) in both left atria (LA) and left ventricle (LV) was significantly elevated in ZSF1 obese rats (FIG. 4H).

Example 19: Obesity-Related Gene Expression Changes in the Left Heart of ZSF1 Rats To characterize the transcriptional effects of obesity and metabolic disfunction on expression of heart tissue specific/abundant genes in left heart, RNA-seq was performed on left ventricle (LV) isolated from 20-week-old male ZSF1 obese and lean males. Comparison of heart abundant protein coding gene expression levels in left ventricle biopsies (LV) from ZSF1 lean and obese donors revealed a relatively small number of genotype-driven gene expression changes in heart-abundant protein coding genes: 56 genes demonstrated significantly increased (FC>1.5, p<0.05, Table 10) expression and the expression of 48 genes was significantly decreased (FC<0.67, p<0.05, Table 11) in obese cohort vs lean.

TABLE 10

Heart abundant tissue gene expression increase in LV of ZSF1 obese vs lean group

| Gene | Log2 FC Increase | BH P value |
|---|---|---|
| Acaa2 | 0.925244 | 8.74E−44 |
| Acadm | 0.623386 | 2.23E−21 |
| Acot2 | 1.407497 | 5.41E−60 |
| Acox1 | 0.612524 | 2.40E−38 |
| Adrala | 0.71756 | 0.000101 |
| Alpk2 | 0.626377 | 3.55E−16 |
| Alpk3 | 0.621277 | 9.72E−26 |
| Ankrd23 | 1.166162 | 2.51E−13 |
| Aqp7 | 0.812687 | 1.77E−18 |

TABLE 10-continued

Heart abundant tissue gene expression increase in LV of ZSF1 obese vs lean group

| Gene | Log2 FC Increase | BH P value |
|---|---|---|
| Cadps | 0.710136 | 2.33E−09 |
| Corin | 0.716298 | 1.73E−20 |
| Cptla | 0.744796 | 8.84E−18 |
| Csdc2 | 0.616815 | 5.22E−10 |
| Decr1 | 1.04417 | 2.83E−47 |
| Dusp26 | 0.762459 | 9.69E−05 |
| Ech1 | 0.836496 | 2.03E−37 |
| Eci1 | 0.776771 | 3.66E−19 |
| Ehhadh | 0.614765 | 1.37E−10 |
| Eya4 | 0.645467 | 7.92E−05 |
| Fhl1 | 0.746967 | 0.000126 |
| Fkbp5 | 1.020574 | 5.82E−10 |
| Gatsl2 | 0.990934 | 1.12E−11 |
| Grip2 | 0.813704 | 1.81E−06 |
| Hadha | 0.597629 | 6.57E−22 |
| Hadhb | 0.588585 | 7.77E−28 |
| Hcn4 | 1.787693 | 6.89E−11 |
| Hipk2 | 1.018523 | 0.000114 |
| Kcna4 | 0.819119 | 1.56E−08 |
| Lpar3 | 1.088838 | 1.58E−21 |
| Lrp4 | 0.746815 | 5.26E−21 |
| Myh7 | 1.387513 | 3.22E−14 |
| Ncam1 | 1.067203 | 7.08E−11 |
| Nppa | 0.713072 | 0.0066 |
| Nrap | 0.713035 | 2.75E−35 |
| Ntn1 | 0.67961 | 1.05E−14 |
| Pank1 | 0.585723 | 3.36E−20 |
| Pcdh20 | 0.680139 | 0.012131 |
| Pcyox1 | 0.601507 | 4.81E−19 |
| Pde3a | 0.746655 | 2.87E−08 |
| Pde7b | 0.618594 | 1.51E−05 |
| Pdk4 | 2.056103 | 2.27E−19 |
| Pdzd2 | 0.664067 | 2.16E−06 |
| Plekha5 | 0.989596 | 5.11E−15 |
| Postn | 1.02457 | 0.000134 |
| Ppcs | 0.590606 | 3.78E−13 |
| Ryr2 | 0.586292 | 1.69E−05 |
| Sema6c | 0.940007 | 2.26E−13 |
| Slc16a1 | 0.599788 | 8.36E−21 |
| Sorbs1 | 0.61142 | 2.33E−06 |
| Sorbs2 | 0.691732 | 3.48E−18 |
| Sphkap | 0.948305 | 1.25E−13 |
| Synpo | 0.682884 | 5.58E−23 |
| Sypl2 | 1.574139 | 3.43E−11 |
| Vwa8 | 0.854878 | 9.36E−12 |
| Xirp2 | 0.95803 | 3.01E−14 |
| Zbtb25 | 0.64347 | 5.25E−05 |

TABLE 11

Heart abundant tissue gene expression decrease in LV of ZSF1 obese vs lean group

| Gene | Log2 FC Decrease | BH P value | Gene | Log2 FC Decrease | BH P value |
|---|---|---|---|---|---|
| Ace2 | −0.65349 | 1.51E−07 | Mrpl33 | −6.523 | 1.93E−09 |
| Alkbh7 | −0.66233 | 1.11E−07 | Myctl | −0.65596 | 1.04E−06 |
| Apin | −0.98546 | 1.93E−17 | Myh6 | −0.83876 | 5.9E−08 |
| Apold1 | −1.29498 | 2.45E−08 | Myl2 | −3.4613 | 1.48E−35 |
| Atpla2 | −0.6179 | 1.36E−17 | Myo16 | −0.91175 | 5.52E−05 |
| Atp5i | −1.03852 | 0.000927 | Myoz1 | −0.73592 | 0.003804 |
| Aurka | −0.62431 | 0.000256 | Ndufa3 | −1.21741 | 0.000483 |
| Btg2 | −1.15314 | 4.11E−08 | Nes | −1.04319 | 2.61E−30 |
| C7 | −0.60483 | 0.000167 | Ngf | −0.58577 | 0.001143 |
| Cdca71 | −0.66148 | 0.000639 | Nr4a2 | −1.2504 | 3.21E−10 |
| Cdh5 | −0.72207 | 3.41E−20 | Nrep | −0.94786 | 2.08E−10 |
| Cenpn | −0.6516 | 0.001388 | Omd | −0.59348 | 6.99E−05 |
| Cox7a2 | −0.60752 | 1.33E−06 | Pcdh12 | −0.9382 | 1.31E−15 |
| Csgalnact1 | −0.60155 | 2.97E−06 | Pet100 | −0.59974 | 0.000045 |
| Cxcl1 | −0.97868 | 0.022871 | Pfkfb2 | −0.74672 | 5.18E−11 |
| Egr2 | −2.0947 | 2.13E−15 | Pomp | −1.989 | 0.000193 |
| Gcat | −0.62848 | 3.12E−05 | Slc39a8 | −1.00884 | 5.57E−14 |
| Gimap8 | −0.7251 | 1.45E−12 | Slirp | −0.61681 | 1.13E−05 |
| Hspe1 | −0.82115 | 0.024196 | Tcfl5 | −1.00965 | 1.49E−12 |
| Lgals3bp | −0.62544 | 1.84E−14 | Tmem88 | −0.80065 | 1.14E−12 |
| Lin9 | −0.62486 | 0.000165 | Tomm7 | −0.79847 | 2.86E−07 |
| Ltc4s | −1.10115 | 0.00606 | Usmg5 | −1.49256 | 0.010782 |
| Magohb | −0.61692 | 0.000599 | Vin | −0.64253 | 4.85E−22 |
| Maob | −0.76571 | 2.23E−11 | Mlf1 | −0.72835 | 5.41E−18 |
| Mlf1 | −0.72835 | 5.41E−18 | Mrpl33 | −6.523 | 1.93E−09 |

Figure 5A:
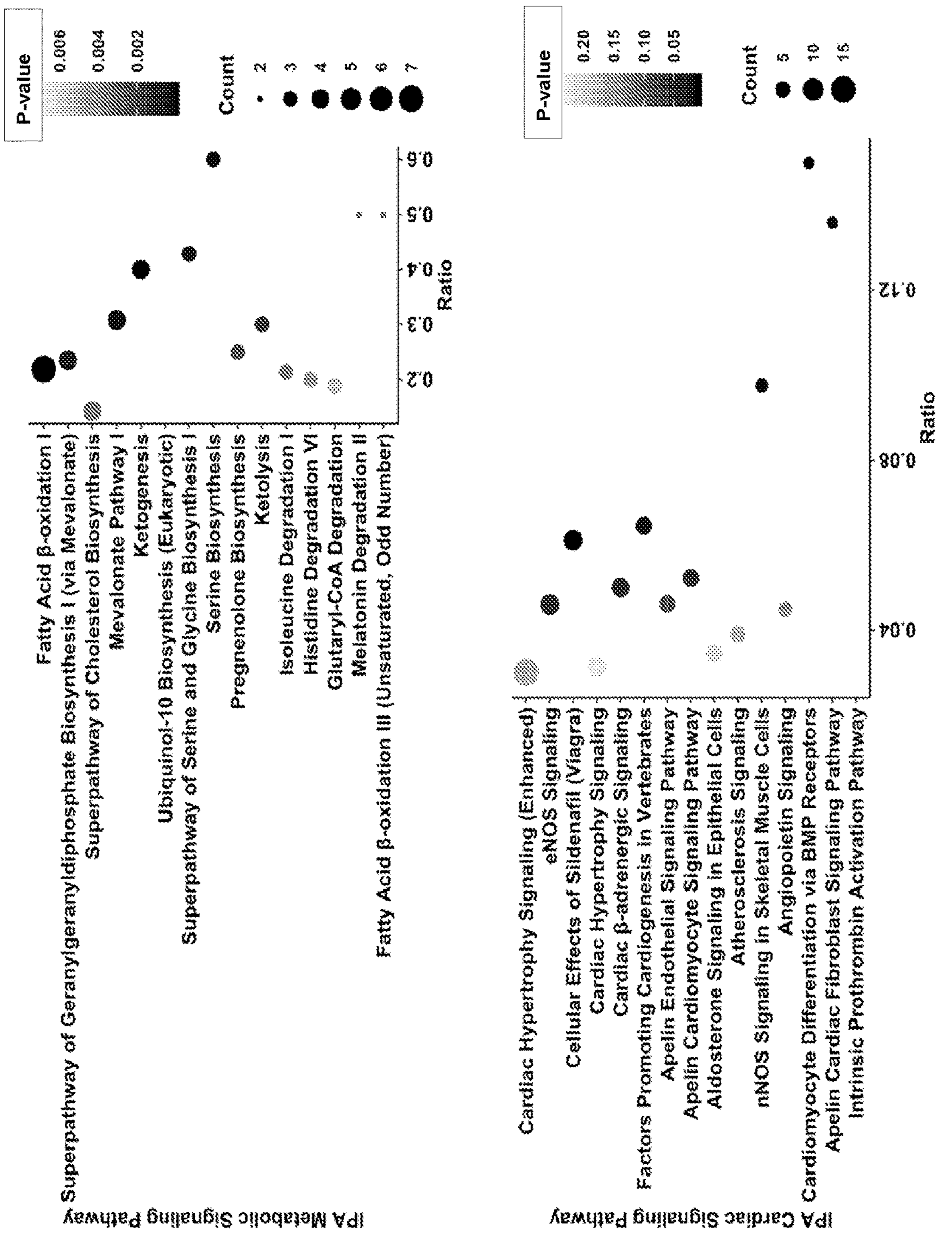
FIG. 5. The gene expression analysis of RNA extracted from left ventricle (LV) of twenty-week-old ZSF1 obese and lean male rats: the obesity-related gene expression changes in left ventricle included 267 significantly increased (FC>1.5, p<0.05) and 431 significantly decreased genes (FC<0.67, p<0.05),), of which 56 increased genes and 48 decreased genes are heart abundant. Ingenuity pathway analysis (IPA) and MeSH term cardiac disease enrichment analysis revealed enriched metabolic and cardiac signaling pathways (FIG. 5A) and overlapping genes in related pathways such as fatty acid metabolism, amino acid metabolism, or left ventricle (LV) hypertrophy, dilated cardiomyopathy, and heart failure (FIG. 5B).
Figure 5B:
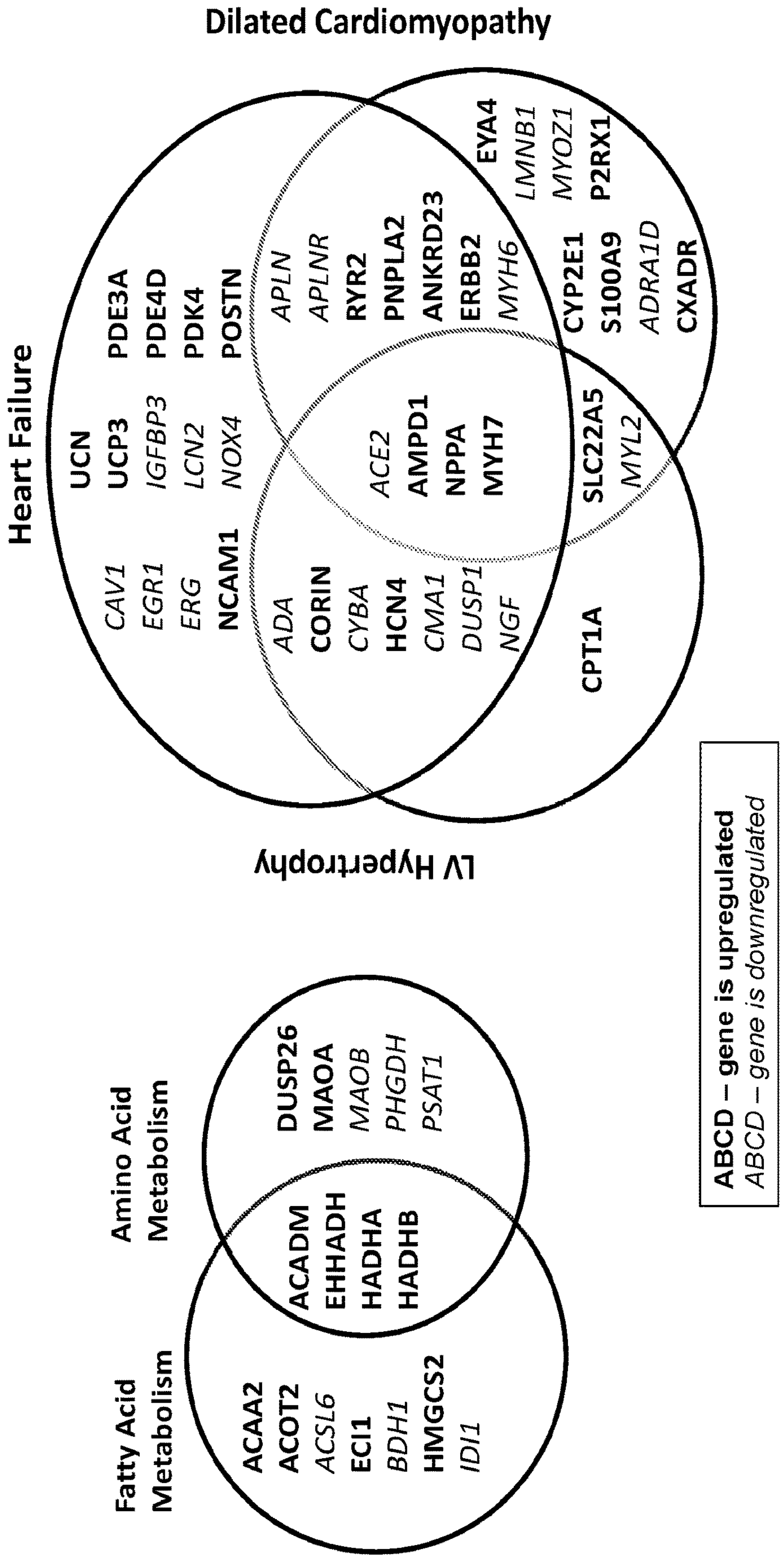

Notably, the IPA pathway enrichment analysis revealed (FIG. 5A) that most of the gene expression changes in LV of ZSF1-obese rats belong to fatty acid and branching amino acid metabolism pathways or to the cardiac signaling pathways (FIG. 5A). The increase in ACADM, EHHADH, HADHA and HADHB gene expression was shared by both fatty acid and branching amino acid metabolism pathways. Altered ACAA2, ACOT2, ACSL6, ECI1, BDH1, IDI1 and HMGCS2 gene expression was fatty acid metabolism specific and altered expression of MAOA, MAOB, DUSP26, PHGDH and PSAT1 in LV was signatorial for the branching amino acid metabolism pathway (FIG. 5B). The MYL2 and MYH6 gene expression decrease together with increased RYR2, HCN4, CORIN, NPPA, ERBB2 and MYH7 were the gene expression changes affecting hypertrophic and/or dilated cardiomyopathy.

Together, Examples 15-19 provide a compelling case that ZSF-1 obese rats exhibit multiple features of human cardiometabolic syndrome: pathological changes in renal, metabolic and CVD circulating biomarkers, obesity-driven changes in expression of heart abundant genes, cardiovascular disfunction with preserved ejection fraction (by hemodynamic assessment and echocardiography), and decreased exercise capacity.

The systemic levels of pancreas-related biomarkers in ZSF1-obese rats demonstrated pancreatic beta-cells disfunction as significantly increased serum C-peptide, proinsulin, glucagon and amylin (FIGS. 2A-2D) were observed. Renal disfunction is a part of CMD, and significantly increased systemic renal injury biomarkers KIM1, NGAL and clasterin (FIGS. 2E-2G) confirmed the presence of diabetic nephropathy and kidney damage in 20-week-old ZSF1-obese male rats.

Biomarkers are a powerful diagnostic and/or prognostic tool for a variety of CVD in humans. The milieu of systemic protein and local molecular cardiovascular biomarker changes (left ventricle of the heart) triggered by the development of CMD in ZSF1-obese rats was studied and the translational value of the observations evaluated. Notably, among the array of systemic changes there was a significant increase of aldosterone (FIG. 4A) together with significant abrogation of heart abundant cardiomyocyte secreted protein NT-proBNP (FIG. 4E) in circulation. There is a strong association of aldosterone increase with hypertension, obesity, chronic kidney disease, metabolic syndrome, high triglycerides, concentric left ventricular hypertrophy, atrial fibrillation and reverse correlation between aldosterone and NT-proBNP. During the last decade several scientific reports from human populational studies demonstrated that serum NT-proBNP concentrations were relatively lower in overweight and obese patients, suggesting a link between the heart and adipose tissue distribution mediated through natriuretic peptides. The observation that human subcutaneous adipose tissue from obese subjects with T2D exhibits markedly increased NP receptors expression leading to the higher clearance of NT-proBNP from the circulation could be a reasonable explanation of significantly decreased serum NT-proBNP without NPPB mRNA expression changes in left heart of ZSF1-obese rats (FIG. 4).

The FABP3 (fatty-acid-binding protein 3) is abundantly expressed in cardiomyocyte cytoplasm, its circulation levels are positively correlated with left ventricle mass index and is proposed to be an early biomarker of myocardial injury in humans. The ST2, circulating protein marker of cardiomyocyte stress and fibrosis, that increases in patients across a wide spectrum of cardiovascular diseases, is now recommended by American College of Cardiology Foundation and American Heart Association joint guidelines for additive risk stratification in patients with heart failure. Chronic inflammation contributes to cardiac fibrosis, and systemic interleukin-16 (IL-16) levels are specifically elevated in HFpEF patients (compared with HFrEF and controls) with a significant association between serum IL-16 and indices (LAVI, E/E' and DWS) of LV diastolic dysfunction. In concert with the published results from human studies serum FABP3, ST2 and IL-16 protein concentrations were significantly elevated in 20-week-old ZSF1-obese male rats (FIGS. 4B-4D) and supported translational value of this preclinical model of human CMS.

The Examples also demonstrate that physical parameters of heart failure with preserved ejection fraction (HFpEF)-specific heart disfunction coincided with pathological changes in CVD circulating biomarkers. Among the biomarkers of HF progression is osteopontin (OPN, abundant kidney protein majorly synthesized in the loop of Henle) that is expressed at medium level in heart tissue by endothelial cells, cardiomyocytes and fibroblasts.

Based on the transcriptome analysis (https://www.proteinatlas.org/humanproteome/tissue/heart) approximately 60% (n=12224 out of 19613) of protein coding genes are expressed in the heart tissue. Two hundred of these genes show an elevated expression in heart compared to other tissue types, and most of the corresponding proteins (localized in the cytoplasm and in the sarcomeres) are involved in muscle contraction, ion transport and ATPase activity. The comparative RNAseq analysis (ZSF1-obese vs lean) of rat LV heart abundant genes described here revealed the dramatic changes in cardiomyocyte, fibroblast and vascular cells gene expression, i.e. significant increase in expression of 59 genes (Table 10) and significant decrease in expression of 48 genes (Table 11) in 20-week-old ZSF1-obese males.

In ZSF1 rat CMS model the obesity and impaired metabolism have also greatly increased CVD pathology by altering two major metabolic pathways in heart tissue (FIG. 5B)—fatty acid (FADS) metabolism and branched-chain amino acid (BCAA) metabolism.

In general, cardiac metabolic homeostasis of fatty acid, glucose, ketone bodies and branched-amino acids are well-established through an intertwined regulatory network. Thus, gene expression of ACADM, EHHADH, HADHA and HADHB, that are essential enzymes involved in both fatty acid metabolism and BCAA catabolism, is greatly increased in ZSF1-obese LV heart tissue. It has been reported that acyl-CoA deficiency in human failing heart disrupts cardiac energy production and leads to cardiac lipotoxicity that in return impairs Heart's ability to function and pump properly and ACAA2, ACADM, ACSL6, ACOT2, EHHADH, HADHA and HADHB are enzymes functionally involved in acyl-CoA metabolism. By human GWAS database analysis the mutations in HADHA and HADHB are associated with familial hypertrophic cardiomyopathy and mutations in ACADM, ACAA2 genes are associated with mitochondrial fatty acid β-oxidation. Several enzymes (ACADM, ACSL6, EHHADH and HMGCS2) are regulated by proliferator activated receptors (PPARs), that manipulate the fuel supply and substrate and modulate the heart failure progression. IPA and MeSH based cardiac signaling and disease analysis demonstrated that significant changes in handful of cardiomyocyte genes (decreased MYL2 and MYH6 and increased RYR2, HCN4, CORIN, NPPA, ERBB2 and MYH7)) were strongly associated with dilated cardiomyopathy, LV hypertrophy and heart failure, and are similar to those observed in human genetic studies aimed to elucidate the genetic basis of cardiomyopathy and heart failure. Hence, the novel RNAseq results in the Examples here demonstrated the array of expression changes in LV heart-abundant genes in ZSF1-obese rats, mainly those involved in fatty acid metabolism, branching amino acid metabolism, hypertrophy, cardiomyopathy and heart failure.

Figure 6A:
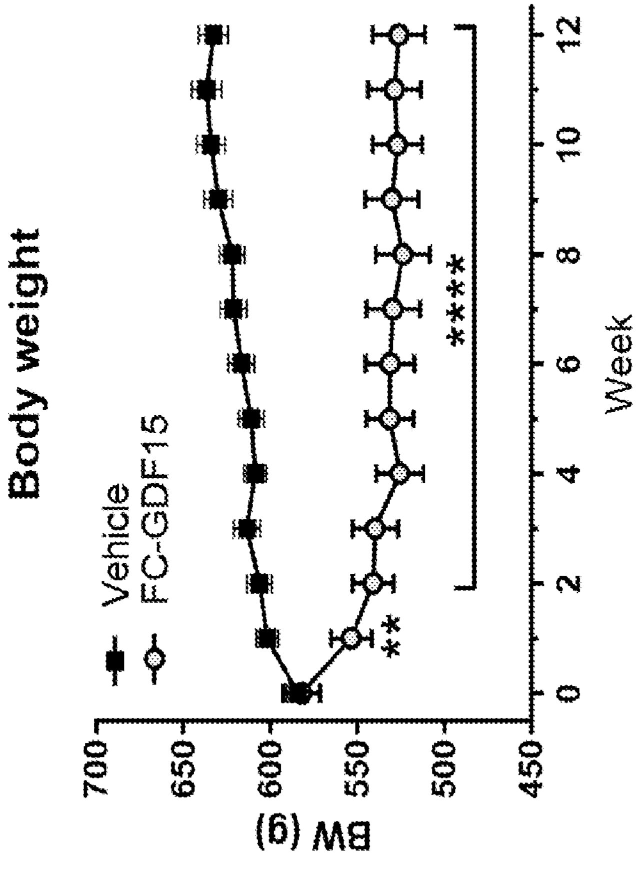
FIG. 6. Treatment of ZSF1 obese rat with FC-GDF15 resulted in statistically significant decrease in body weight (FIG. 6A), food intake (FIG. 6B), blood triglyceride (FIG. 6C) and glucose levels (FIG. 6D), and trend to decrease total cholesterol (FIG. 6E). Blood insulin was significantly increased at week 9 and 12 in rats treated with GDF15 compared to vehicle treated rats (FIG. 6F). Twelve weeks of FC-GDF15 treatment resulted in statistically significant increase in blood adiponectin (FIG. 6G) and had no effect on endogenous rat GDF15 (FIG. 611) Stars (*) indicate significance (* p<0.05,  p<0.01, * p<0.001, **** p<0.0001), unpaired two-tailed t-test.
Figure 6B:
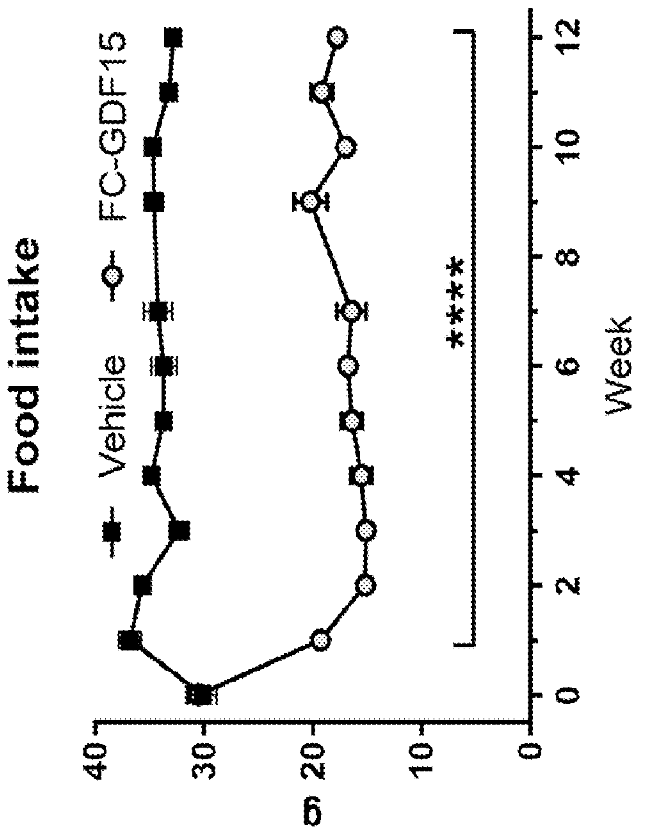
Figure 6D:
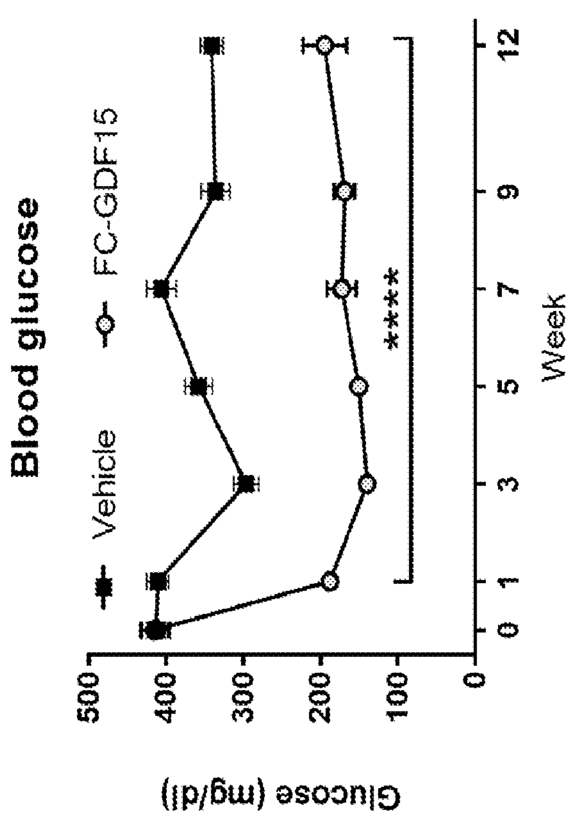
Figure 6C:
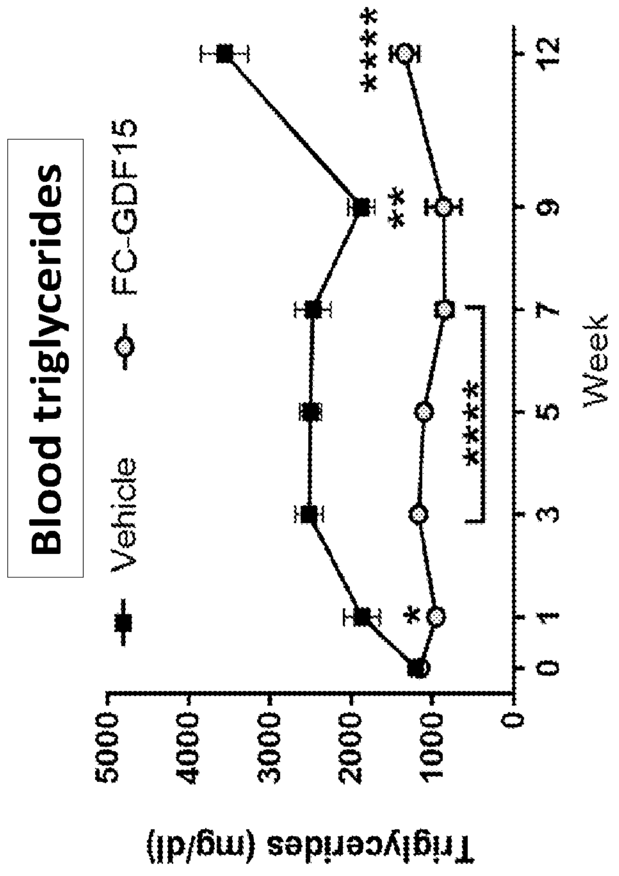
Figure 6E:
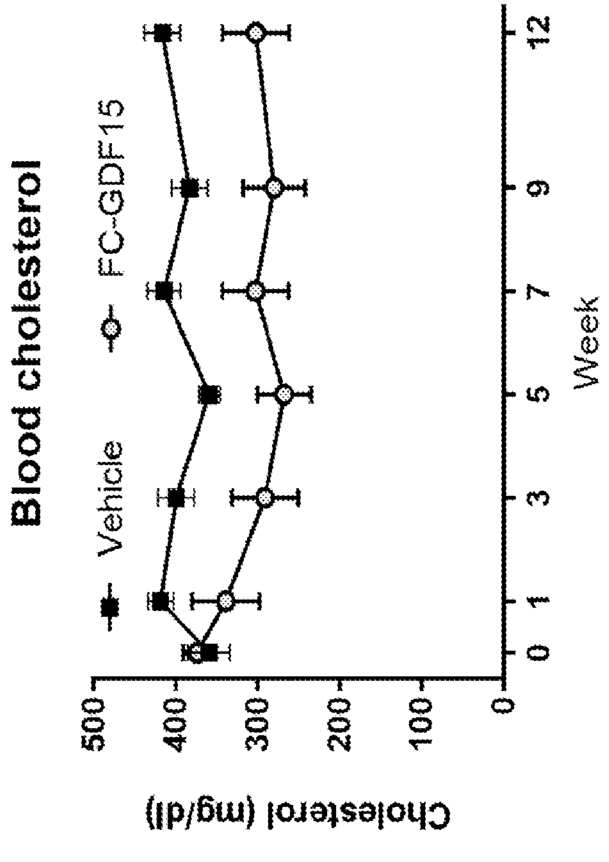
Figure 6F:
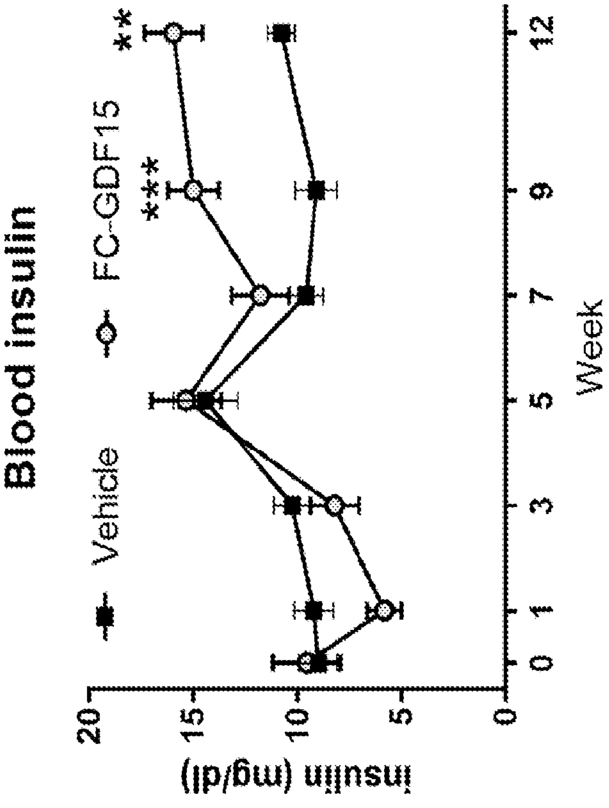
Figure 6G:
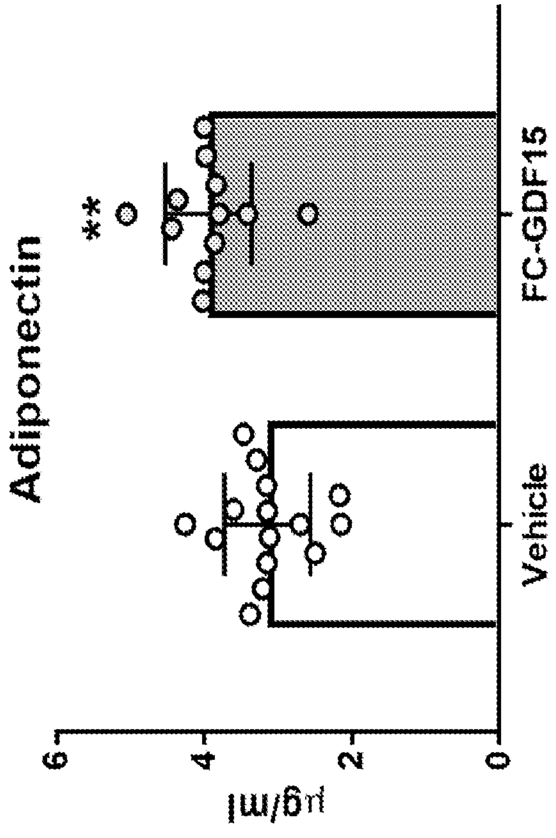
Figure 6H:
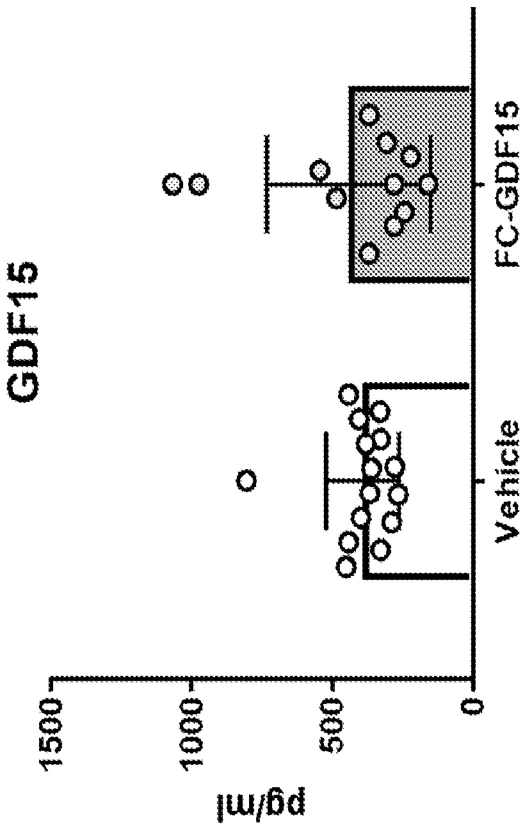

Example 20: ZSF1 Obese Rats Treated with GDF15 Exhibit Metabolism Improvement by Changes in Systemic Parameters and Biomarkers of Obesity and Metabolism Impairment For the duration of FC-GDF15 or Vehicle treatment (see Example 2) both cohorts of ZSF1 obese rat were monitored weekly for the food intake and body weight and bi-weekly for blood levels of cholesterol, triglycerides, insulin and glucose (FIG. 6). Within first two weeks of the FC-GDF15 treatment, significant and sustained decrease (to the end of the study) in body weight (FIG. 6A), food intake (FIG. 6B), blood triglycerides (FIG. 6C) and blood glucose (FIG. 6D) was observed and documented. Blood cholesterol was 20-30% lower in FC-GDF15 treated cohort of ZSF1 obese rats (vs Vehicle group) from week 1 to week 12 of the treatment, but such decrease did not achieve significance at any tested time point of the study (FIG. 6E). At the same time blood insulin levels significantly increased at weeks 9 and 12 of FC-hGDF15 treatment (FIG. 6F) compared to the vehicle group. At the end of 12-week-long FC-GDF15 treatment circulating adiponectin concentration was significantly increased (FIG. 6G). At the same time the endogenous rat GDF15 level in serum of FC-hGDF15 treated and Vehicle treated ZSF1 obese rats remained similar (FIG. 6H).

Example 21: GDF15 Treatment of ZSF1 Obese Rats LED to the Significant Positive Changes in Systemic Levels of Cardiovascular Biomarkers The systemic levels of cardiovascular biomarkers in ZSF1 obese rats were evaluated at the end of the study and are presented in Table 12.

TABLE 12

Effect of GDF15 treatment on systemic levels of cardiovascular markers

| Biomarker | Serum concentration at wk 12 of FC-GDF15 treatment (Mean ± SEM) Vehicle group | hGDF15 group | P value |
|---|---|---|---|
| Adiponectin (μg/ml) | 3.15 ± 0.15 | 3.95 ± 0.17 | 0.0015 |
| Aldosterone (pg/ml) | 261.5 ± 45.3 | 237.1 ± 45.8 | 0.7118 |
| BNP (pg/ml) | 4.14 ± 1.16 | 4.67 ± 1.66 | 0.8204 |
| sE-Selectin (ng/ml) | 245.6 ± 12.6 | 146.0 ± 12.0 | <0.0001 |
| FABP3 (ng/ml) | 7.52 ± 1.53 | 5.93 ± 2.28 | 0.5549 |
| sICAM (ng/ml) | 29.97 ± 2.01 | 15.72 ± 2.04 | <0.0001 |
| MCP1 (ng/ml) | 4.16 ± 0.24 | 3.52 ± 0.22 | 0.0683 |
| Myl3 (pg/ml) | 154.1 ± 14.41 | 99.9 ± 22.6 | 0.0458 |
| NT-proANP (ng/ml) | 20.44 ± 1.30 | 18.08 ± 1.54 | 0.2490 |
| NT-proBNP (ng/ml) | 12.65 ± 1.98 | 15.90 ± 2.53 | 0.3148 |
| Osteopontin (ng/ml) | 2.09 ± 0.14 | 1.70 ± 0.12 | 0.0494 |
| TIMP1 (ng/ml) | 21.04 ± 2.14 | 12.91 ± 2.08 | 0.01129 |
| VEGF (pg/ml) | 72.87 ± 6.76 | 25.0 ± 10.63 | 0.0006 |
| vWF (ng/ml) | 186.9 ± 9.83 | 125.1 ± 15.2 | 0.0016 |
| GDF15 (pg/ml) | 392.6 ± 33.3 | 443.2 ± 84.2 | 0.5512 |

Figure 7B:
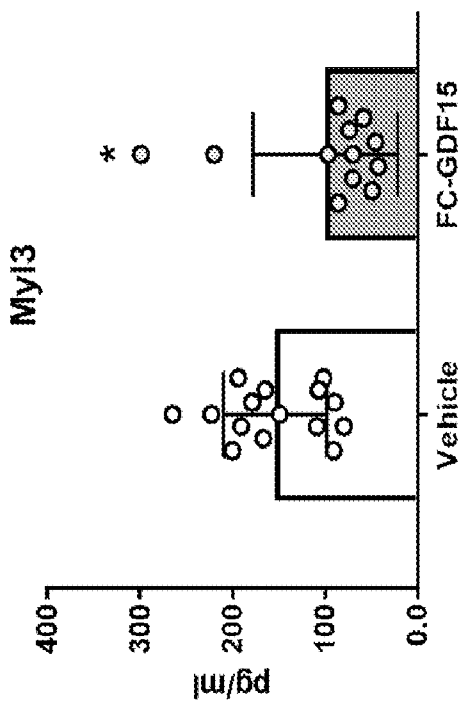
FIG. 7. ZSF1 obese rats treated with FC-GDF15 for 12 weeks exhibit statistically significant decrease in systemic levels of CVD-related biomarkers vWF (FIG. 7A), Myl3 (FIG. 7B), osteopontin (FIG. 7C), E-Selectin (FIG. 7D), sICAM (FIG. 7E), VEGF (FIG. 7F) and TIMP-1 (FIG. 7G) at the end of the study. Significance (* p<0.05) determined using an unpaired two-tailed t-test. N=11 for Vehicle, N=8 for GDF15-Fc treated groups, respectively.
Figure 7A:
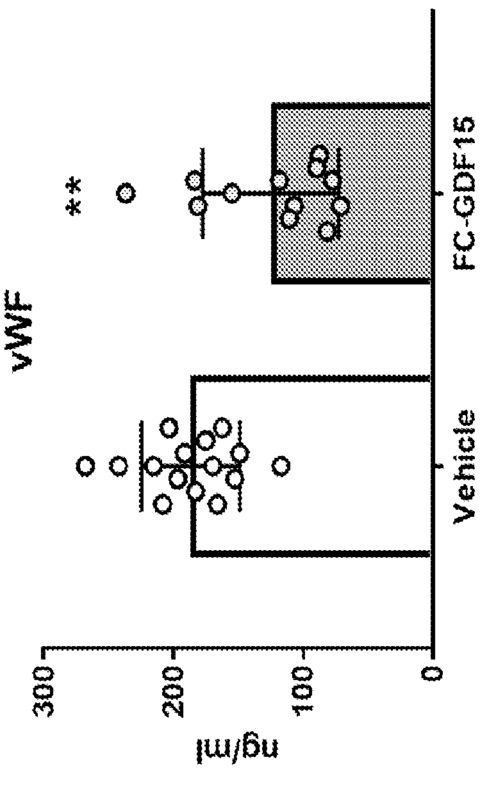
Figure 7C:
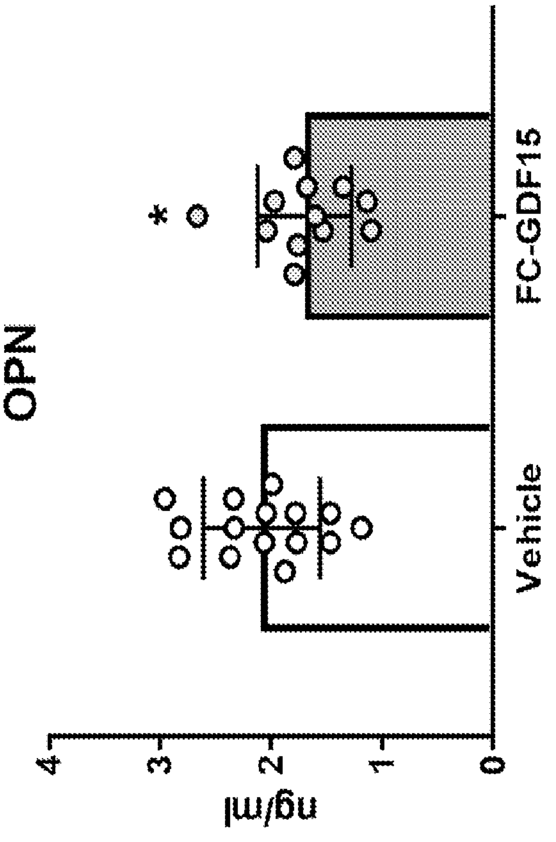
Figure 7D:
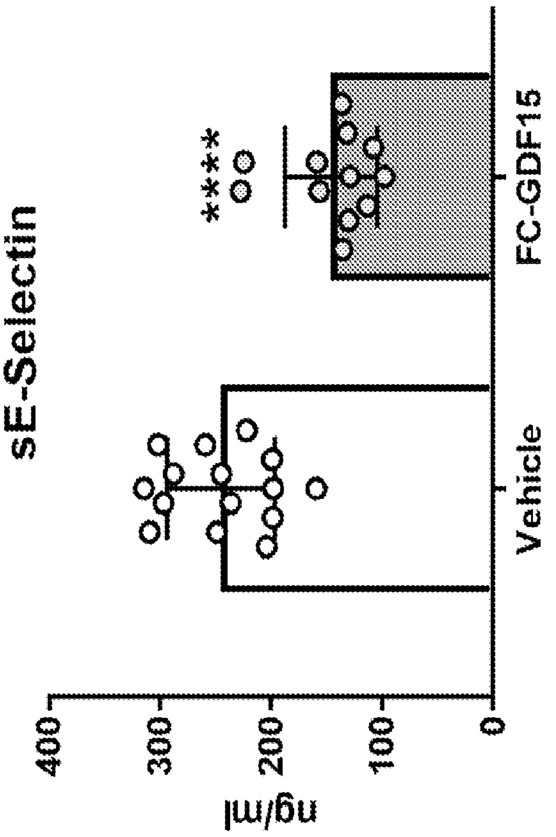
Figure 7E:
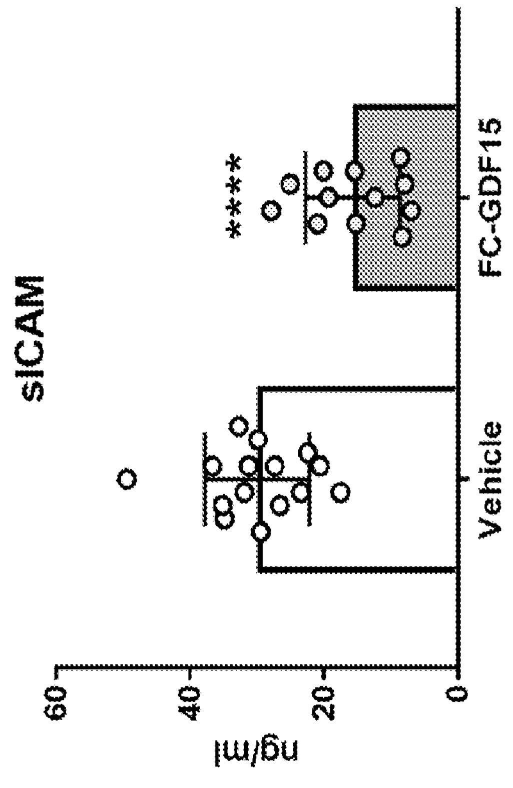
Figure 7F:
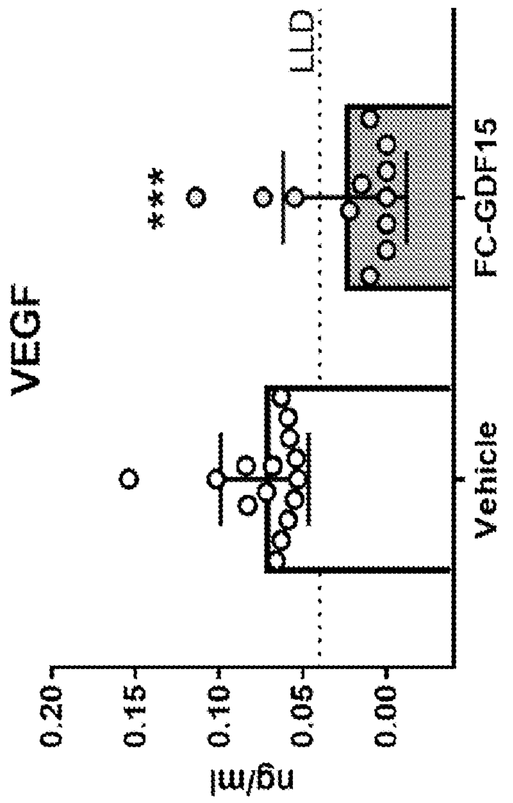
Figure 7G:
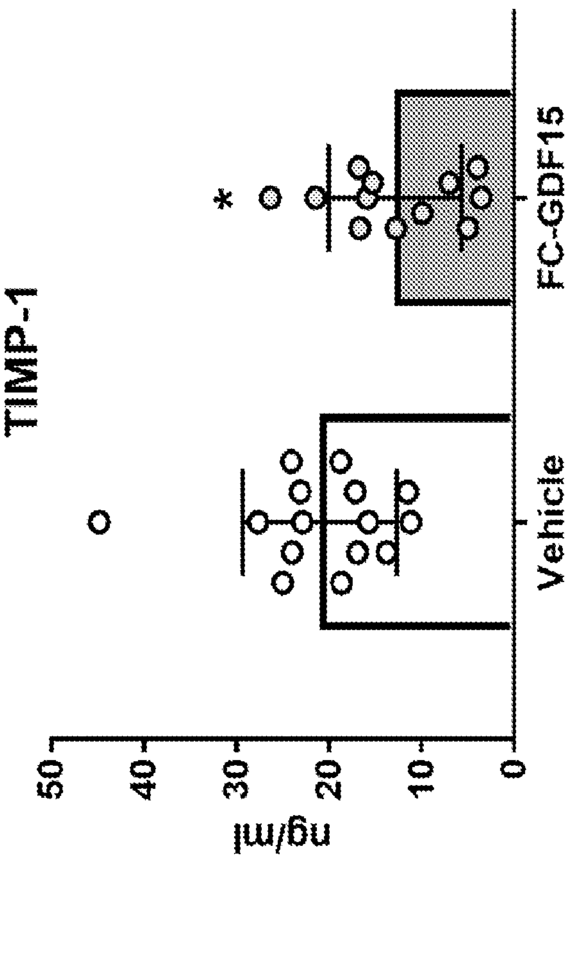

Following 12 weeks of FC-hGDF15 administration significant positive changes in the array of cardiovascular biomarkers in circulation was observed. Thus, systemic markers of cardiac injury vWF (FIG. 7A) and Myl3 (FIG. 7B) were 30-50% lower ($p<0.05$) in FC-hGDF15 treated group. Heart failure associated osteopontin (FIG. 7C), markers of vascular injury E-Selectin (FIG. 7D), sICAM (FIG. 7E), and VEGF (FIG. 7F) and marker of cardiovascular fibrosis TIMP-1 (FIG. 7G) were significantly lower in serum/plasma of GDF15-treated vs. Vehicle-treated ZSF1 obese rats (($p<0.05$). At the same time the other systemic biomarkers of CVD, such as NT-proBNP, NT-proANP, BNP, FABP3, MCP1 and aldosterone were not systemically changed by 12-week-long FC-hGDF15 treatment (Table 12).

Figure 8B:
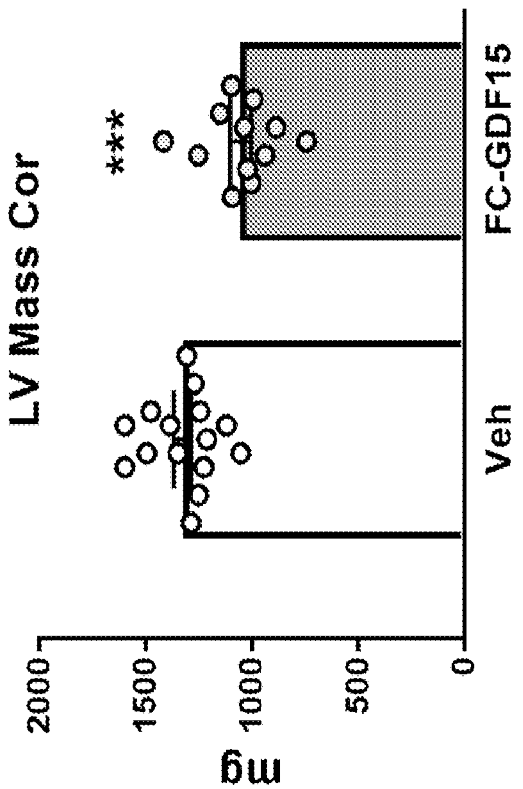
FIG. 8. Twelve weeks of FC-GDF15 treatment resulted in statistically significant decrease in heart weight and improved exercise capacity during treadmill challenge by the increase in running distance and the length of time to exhaustion. FC-GDF15 treatment resulted in significant decrease in heart to brain weight ratio (FIG. 8A), LV mass (FIG. 8B), cardiac output (FIG. 8C), stroke volume (FIG. 8D) and % ejection fraction echocardiographic parameters (FIG. 8E), when compared to ZSF1 obese rats treated with Vehicle (FIG. 7A-E). GDF15 treatment had no effect on heart rate (FIG. 8F). After the twelve weeks of treatment, when exposed to a treadmill challenge, the FC-hGDF15 group demonstrated improved exercise capacity by exhibiting significantly longer running time (FIG. 8G) and running distance (FIG. 8H) vs. Vehicle group. Stars (*) indicate significance (* p<0.05,  p<0.01, * p<0.001, **** p<0.0001), unpaired two-tailed t-test).
Figure 8A:
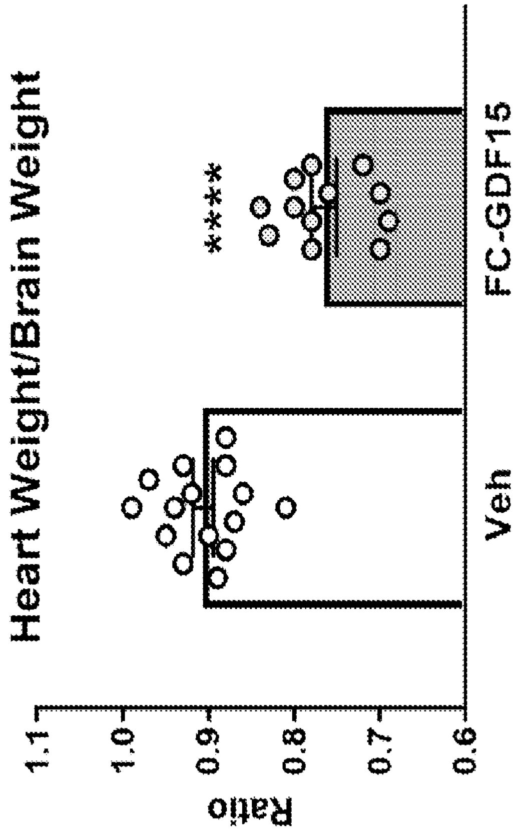
Figure 8D:
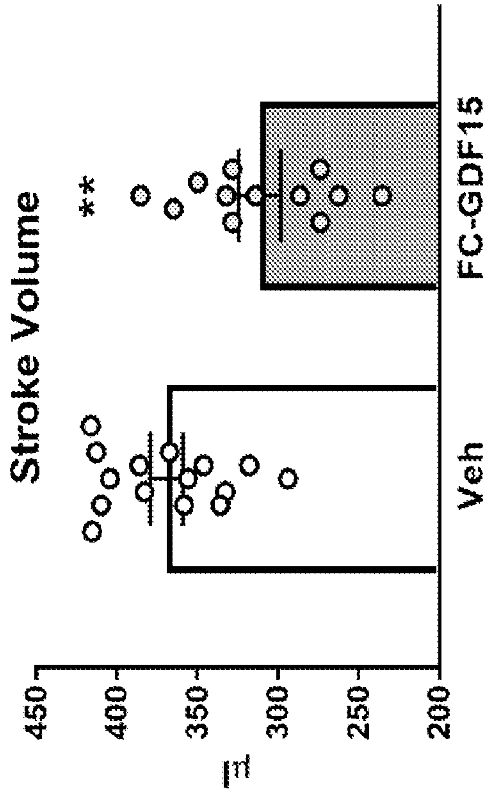
Figure 8C:
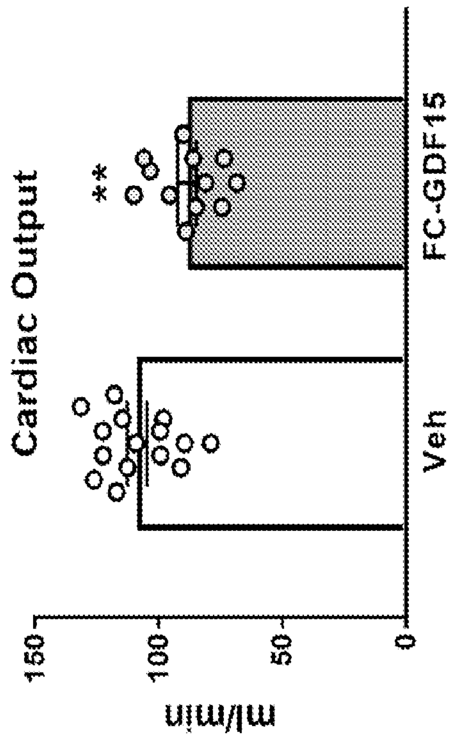
Figure 8F:
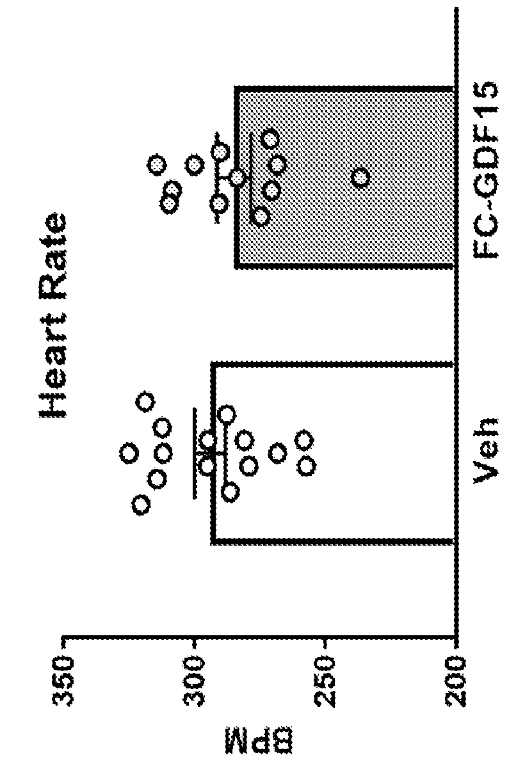
Figure 8E:
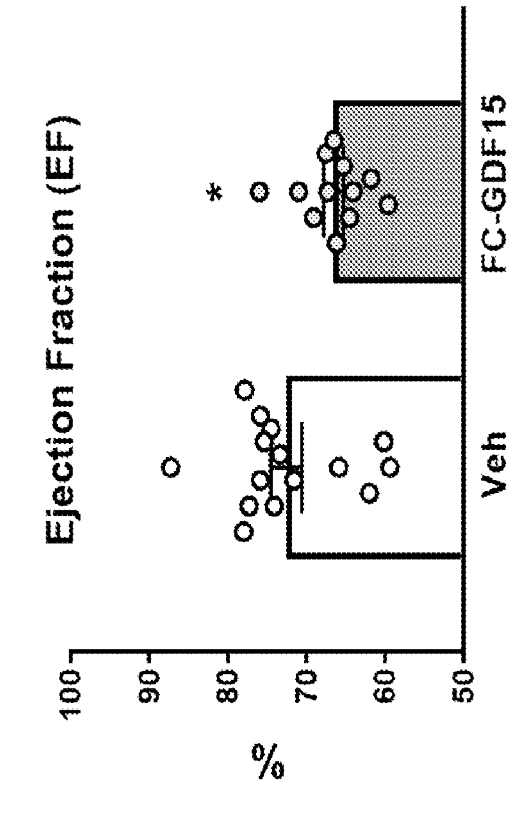
Figure 8G:
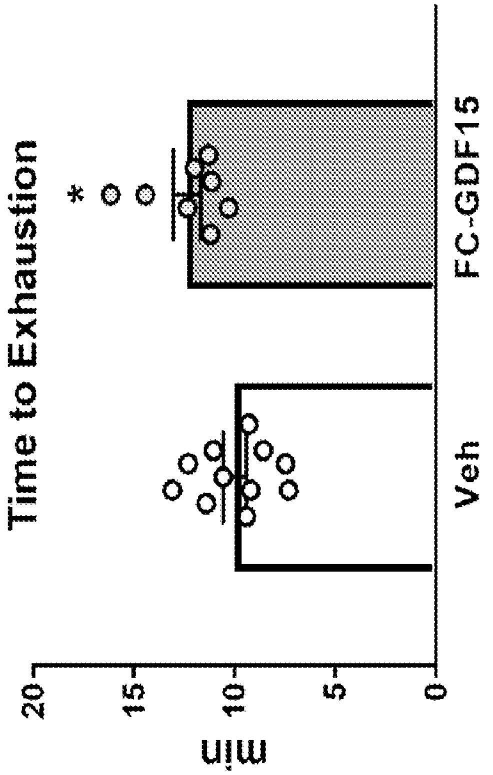
Figure 8H:
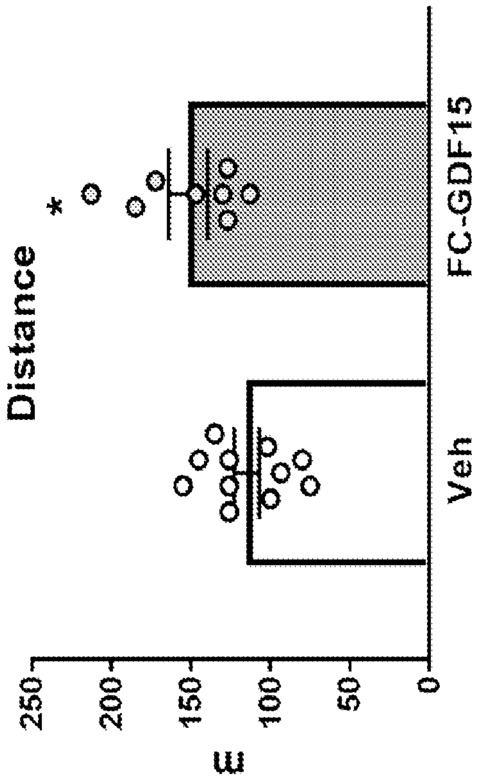

Example 22: GDF15 Therapeutic Approach Effected Echography Parameters of Left Heart Function and Improved Exercise Capacity in ZSF1 Obese Rats When the ZSF1 obese rats were characterized, it was demonstrated that at the age of 20 weeks males exhibit diastolic dysfunction and decreased exercise capacity. Twelve weeks of FC-hGDF15 treatment of ZSF1 obese males resulted in significantly decreased heart to brain weight ratio (by echocardiography, Table 13, FIG. 8), LV mass, cardiac output, stroke volume and % ejection fraction echocardiographic parameters, when compared to ZSF1 obese rats treated with Vehicle (FIGS. 8A-8E). GDF15 treatment had no effect on heart rate (FIG. 8F).

TABLE 13

Effect of 12 week-long hGDF15 treatment on parameters of invasive hemodynamic assessment, echocardiography and exercise capacity of ZSF1 obese male rats

| Biomarker | Physical parameters (Mean ± SEM) Vehicle group | FC-GDF15 group | P value |
|---|---|---|---|
| Heart/Brain Weight (ratio) | 0.907 ± 0.01 | 0.765 ± 0.01 | <0.0001 |
| Heart Rate (bpm) | 294.0 ± 5.8 | 284.9 ± 6.4 | 0.3024 |
| Diameter (s) (mm) | 5.35 ± 0.23 | 5.63 ± 0.13 | 0.3458 |
| Diameter (d) (mm) | 9.56 ± 0.15 | 9.15 ± 0.16 | 0.0711 |
| Volume (s) (μl) | 143.7 ± 14.06 | 156.4 ± 8.42 | 0.4722 |

TABLE 13-continued

Effect of 12 week-long hGDF15 treatment on parameters of invasive hemodynamic assessment, echocardiography and exercise capacity of ZSF1 obese male rats

| | Physical parameters (Mean ± SEM) | | |
|---|---|---|---|
| Biomarker | Vehicle group | FC-GDF15 group | P value |
| Volume (d) (μl) | 512.8 ± 17.93 | 467.8 ± 17.87 | 0.0914 |
| Stroke Volume (μl) | 369.1 ± 10.04 | 311.4 ± 13.02 | 0.0015 |
| Ejection Fraction (%) | 72.59 ± 1.98 | 66.58 ± 1.23 | 0.0225 |
| Fractional Shortening (%) | 44.17 ± 1.75 | 38.63 ± 1.01 | 0.0167 |
| Cardiac Output (ml/min) | 108.7 ± 3.95 | 88.49 ± 3.84 | 0.0013 |
| LV Mass (mg) | 1657 ± 51.83 | 1317 ± 62.41 | 0.0003 |
| LV Mass Cor (mg) | 1326 ± 41.46 | 1054 ± 49.93 | 0.0003 |
| IVRT (ms) | 25.72 ± 0.65 | 28.52 ± 1.19 | 0.0399 |
| EDP (mmHg) | 15.94 ± 0.63 | 16.27 ± 1.02 | 0.7733 |
| Tau (ms) | 13.79 ± 0.57 | 13.86 ± 0.87 | 0.9414 |
| E/E' (Ratio) | 18.49 ± 0.75 | 16.98 ± 0.73 | 0.1697 |
| Distance (m) | 114.9 ± 7.95 | 151.8 ± 12.32 | 0.0173 |
| Time to Exhaustion (min) | 9.98 ± 0.57 | 12.37 ± 0.7 | 0.0160 |
| Peak VO2 (mg · kg-1 · hr-1) | 3093 ± 74.3 | 3122 ± 123.2 | 0.8331 |
| Respiratory Exchange (Ratio) | 1.008 ± 0.018 | 0.9949 ± 0.015 | 0.5998 |

After the twelve weeks of treatment, when exposed to a treadmill challenge, the FC-hGDF15 group demonstrated improved exercise capacity (Table 13) by exhibiting significantly longer running time (FIG. 8G) and running distance (FIG. 811) vs. Vehicle group. However, peak VO2 (a measure of aerobic fitness) and the respiratory exchange ratio (RER, a fatigue measure) were not significantly different between groups (Table 13) suggesting that both groups were run to the same level of exhaustion.

In Examples 20-22, ZSF1-obese rats were treated with a pharmacological dose of Fc-GDF15 for 12 weeks and compared the outcome with the ZSF1-obese cohort treated with Vehicle. Twelve-week-long GDF15 treatment resulted in significantly decreased body weight and food intake, confirming its capacity to mediate aversive dietary response. Fc fusion GDF15 molecule improved metabolic parameters (decreased blood glucose and triglycerides) in ZSF1-obese rats (FIG. 6A-6F). Serum adiponectin in GDF15-treated ZSF1-obese cohort was significantly increased. Adiponectin is secreted majorly by adipocytes, but also by skeletal and cardiac myocytes and endothelial cells. Its reduction plays a central role in CMS, since adiponectin is positively associated with insulin sensitivity, anti-atherogenic, and anti-inflammatory properties, and according to the numerous epidemiological studies hypoadiponectinemia (adiponectin deficiency) is additionally associated with such cardiovascular diseases as hypertension, CAD and left ventricular hypertrophy. While circulating adiponectin was decreased by 30% in ZSF1-obese vs lean (FIG. 1F), the GDF15 treatment led to its significant systemic increase (29%, FIG. 6G) vs. ZSF1-obese cohort treated with Vehicle. Even though, GDF15 treatment did not lead to the systemic changes in aldosterone, NT-proBNP and FABP3 in ZSF1-obese rats, the novel and exploratory systemic protein markers of cardiac injury vWF and Myl3, HF-associated osteopontin, markers of vascular injury E-Selectin, sICAM, and VEGF and cardiovascular fibrosis marker TIMP-1 were significantly lower in GDF15-treated obese rats vs. Vehicle cohort (FIG. 7). In addition to the positive changes in the array of systemic cardiometabolic biomarkers, 12-week-long Fc-GDF15 therapy led to the considerably decreased heart weight together with improved parameters of LV function (decreased LV mass, cardiac output and stroke volume, FIG. 8) and exercise capacity (time to exhaustion and distance, FIG. 8), when compared to Vehicle-treated ZSF1-obese littermates. In summary, ZSF1-obese rat males represent translational preclinical model of human CMS with established HFpEF. Furthermore, GDF15 treatment of ZSF1-obese rats demonstrated its cardioprotective therapeutic effect.

While the present invention has been described in terms of various embodiments, it is understood that variations and modifications will occur to those skilled in the art. Therefore, it is intended that the appended claims cover all such equivalent variations that come within the scope of the invention as claimed. In addition, the section headings used herein are for organizational purposes only and are not to be construed as limiting the subject matter described.

All references cited in this application are expressly incorporated by reference herein for any purpose.

What is claimed is:

1. A method of decreasing heart weight, improving exercise capacity, or changing the level of adiponectin, sE-selectin, soluble ICAM (sICAM), myosin light chain 3 (My13), osteopontin, tissue inhibitor of metalloproteinases 1 (TIMP1), vascular endothelial growth factor (VEGF), or von Willebrand factor (vWF), in a subject with cardiometabolic syndrome and heart failure with preserved ejection fraction (HFpEF) comprising administering a growth differentiation factor 15 (GDF15) molecule to the subject, wherein the GDF15 molecule is a fusion protein comprising a GDF15 region joined to an Fc region, wherein the GDF15 region comprises an amino acid sequence selected from SEQ ID NOs: 6 and 13-18 and the Fc region comprises an amino acid sequence selected from SEQ ID NOs: 26-31.

2. The method of claim 1, wherein the level of adiponectin is increased.

3. The method of claim 1, wherein the level of sE-selectin, sICAM, My13, osteopontin, TIMP1, VEGF, vWF, or any combination thereof is decreased.

4. The method of claim 1, wherein the subject has decreased heart to brain weight ratio, left ventricle (LV) mass, cardiac output, stroke volume, or % ejection fraction echocardiographic, after treatment with the GDF15 molecule.

5. The method of claim 1, wherein the GDF15 region is joined to the Fc region via a linker.

6. The method of claim 5, wherein the linker comprises an amino acid sequence selected from SEQ ID NOs: 19-25 and 58.

7. The method of claim 5, wherein the linker comprises the amino acid sequence of SEQ ID NO: 25.

8. The method of claim 1, wherein the Fc region comprises the amino acid sequence of SEQ ID NO: 30.

9. The method of claim 1, wherein the GDF15 molecule comprises the amino acid sequence of SEQ ID NO: 50.

10. The method of claim 1, wherein the GDF15 region comprises the amino acid sequence of SEQ ID NO: 18.

* * * * *